US012105872B2

(12) United States Patent
Khaderi et al.

(10) Patent No.: US 12,105,872 B2
(45) Date of Patent: *Oct. 1, 2024

(54) METHODS AND SYSTEMS FOR OBTAINING, AGGREGATING, AND ANALYZING VISION DATA TO ASSESS A PERSON'S VISION PERFORMANCE

(71) Applicant: Sphairos, Inc., Venice, CA (US)

(72) Inventors: Syed Khizer Rahim Khaderi, Venice, CA (US); Mohan Komalla Reddy, Fremont, CA (US); Kyle Christopher McDermott, Playa Vista, CA (US)

(73) Assignee: Sphairos, Inc., Venice, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/066,401

(22) Filed: Dec. 15, 2022

(65) Prior Publication Data

US 2023/0195222 A1 Jun. 22, 2023

Related U.S. Application Data

(63) Continuation of application No. 16/232,712, filed on Dec. 26, 2018, now Pat. No. 11,561,614, which is a
(Continued)

(51) Int. Cl.
*G06F 3/01* (2006.01)
*A61B 3/00* (2006.01)
(Continued)

(52) U.S. Cl.
CPC ............ *G06F 3/013* (2013.01); *A61B 3/0091* (2013.01); *A61B 3/024* (2013.01); *A61B 3/028* (2013.01);
(Continued)

(58) Field of Classification Search
CPC ........ G06F 3/013; G06F 3/0346; G06F 3/147; A61B 3/0091; A61B 3/024; A61B 3/028;
(Continued)

(56) References Cited

U.S. PATENT DOCUMENTS 5,422,690 A 6/1995 Rothberg
5,920,375 A 7/1999 Fahle
(Continued)

FOREIGN PATENT DOCUMENTS

WO 2008043027 A2 4/2008
WO 2008043029 A2 4/2008
(Continued)

OTHER PUBLICATIONS

Beatty, Jackson; Lucero-Wagoner, Brennis; Chapter Six: "The Pupillary System", Handbook of Psychophysiology, 2nd Ed., Cambridge University Press, 2000, pp. 142-162.
(Continued)

*Primary Examiner* — Mohammed A Hasan
(74) *Attorney, Agent, or Firm* — Novel IP

(57) ABSTRACT

The present specification describes methods and systems for modifying a media, such as Virtual Reality, Augmented Reality, or Mixed Reality (VR/AR/MxR) media based on a vision profile and a target application. In embodiments of the specification, a Sensory Data Exchange (SDE) is created that enables identification of various vision profiles for users and user groups. The SDE may be utilized to modify one or more media in accordance with each type of user and/or user group.

11 Claims, 74 Drawing Sheets

Related U.S. Application Data continuation of application No. 15/482,560, filed on Apr. 7, 2017, now Pat. No. 10,209,773.

(60) Provisional application No. 62/425,736, filed on Nov. 23, 2016, provisional application No. 62/381,784, filed on Aug. 31, 2016, provisional application No. 62/363,074, filed on Jul. 15, 2016, provisional application No. 62/359,796, filed on Jul. 8, 2016, provisional application No. 62/322,741, filed on Apr. 14, 2016, provisional application No. 62/319,825, filed on Apr. 8, 2016.

(51) Int. Cl.

| | | |
|---|---|---|
| A61B 3/024 | (2006.01) | |
| A61B 3/028 | (2006.01) | |
| A61B 3/10 | (2006.01) | |
| A61B 3/113 | (2006.01) | |
| A61B 5/369 | (2021.01) | |
| A63F 13/212 | (2014.01) | |
| A63F 13/25 | (2014.01) | |
| G02B 27/00 | (2006.01) | |
| G02B 27/01 | (2006.01) | |
| G06F 3/0346 | (2013.01) | |
| G06F 3/147 | (2006.01) | |
| G09G 5/00 | (2006.01) | |
| A61B 5/024 | (2006.01) | |
| A61B 5/11 | (2006.01) | |
| A61B 5/378 | (2021.01) | |
| A61B 5/38 | (2021.01) | |

(52) U.S. Cl.
CPC ............... *A61B 3/10* (2013.01); *A61B 3/113* (2013.01); *A61B 5/369* (2021.01); *A63F 13/212* (2014.09); *A63F 13/25* (2014.09); *G02B 27/0093* (2013.01); *G02B 27/0172* (2013.01); *G06F 3/0346* (2013.01); *G06F 3/147* (2013.01); *G09G 5/006* (2013.01); *A61B 5/024* (2013.01); *A61B 5/11* (2013.01); *A61B 5/378* (2021.01); *A61B 5/38* (2021.01); *G02B 2027/0138* (2013.01); *G09G 2320/0693* (2013.01); *G09G 2354/00* (2013.01)

(58) Field of Classification Search
CPC ........... A61B 3/10; A61B 3/113; A61B 5/369; A61B 5/024; A61B 5/11; A61B 5/378; A61B 5/38; A61B 5/165; A61B 5/7275; A63F 13/212; A63F 13/25; G02B 27/0093; G02B 27/0172; G02B 2027/0138; G09G 5/006; G09G 2320/0693; G09G 2354/00; G16H 40/60; G16H 50/20
USPC ....................................................... 351/246
See application file for complete search history.

(56) References Cited

U.S. PATENT DOCUMENTS

| | | | |
|---|---|---|---|
| 6,089,714 A | 7/2000 | Galiana | |
| 6,118,456 A | 9/2000 | Cooper | |
| 6,367,932 B1 | 4/2002 | Donaldson | |
| 7,211,050 B1 | 5/2007 | Caplygin | |
| 7,367,673 B2 | 5/2008 | Mcgrath | |
| 7,513,622 B2 | 4/2009 | Khaderi | |
| 7,621,639 B2 | 11/2009 | Khaderi | |
| 7,699,466 B2 | 4/2010 | Hayakawa | |
| 7,938,539 B2 | 5/2011 | Khaderi | |
| 8,075,136 B2 | 12/2011 | Newman | |
| 8,251,508 B2 | 8/2012 | Khaderi | |
| 8,798,374 B2 | 8/2014 | Bartlett | |
| 8,820,931 B2 | 9/2014 | Walsh | |
| 9,530,048 B2 | 12/2016 | Bartlett | |
| 9,538,912 B2 | 1/2017 | Khaderi | |
| 10,209,773 B2 | 2/2019 | Khaderi | |
| 10,299,673 B2 | 5/2019 | Khaderi | |
| 11,096,570 B2 | 8/2021 | Khaderi | |
| 11,163,156 B2 | 11/2021 | Khaderi | |
| 11,561,614 B2* | 1/2023 | Khaderi | ............ G02B 27/0172 |
| 2006/0025658 A1 | 2/2006 | Newman | |
| 2006/0114414 A1 | 6/2006 | Mcgrath | |
| 2007/0166675 A1 | 7/2007 | Atkins | |
| 2007/0200927 A1 | 8/2007 | Krenik | |
| 2008/0084536 A1 | 4/2008 | Khaderi | |
| 2008/0158096 A1 | 7/2008 | Breed | |
| 2008/0161661 A1* | 7/2008 | Gizewski | ............ A61B 5/0064 600/306 |
| 2010/0045935 A1 | 2/2010 | Khaderi | |
| 2010/0092929 A1 | 4/2010 | Hallowell | |
| 2010/0156892 A1 | 6/2010 | Chan, II | |
| 2011/0043759 A1 | 2/2011 | Bushinsky | |
| 2012/0322588 A1 | 12/2012 | Khaderi | |
| 2013/0021373 A1 | 1/2013 | Vaught | |
| 2013/0044291 A1 | 2/2013 | Kato | |
| 2014/0039510 A1* | 2/2014 | van Saarloos | ......... A61B 3/107 606/107 |
| 2014/0152792 A1 | 6/2014 | Krueger | |
| 2014/0195900 A1 | 7/2014 | Gabel | |
| 2014/0212404 A1 | 7/2014 | Khaderi | |
| 2014/0270494 A1* | 9/2014 | Sawhney | ............... G06F 18/217 382/159 |
| 2015/0009117 A1 | 1/2015 | Peters | |
| 2015/0009121 A1 | 1/2015 | Chuang | |
| 2015/0213634 A1 | 7/2015 | Karmarkar | |
| 2015/0242780 A1 | 8/2015 | Besner | |
| 2015/0374303 A1 | 12/2015 | Gelbman | |
| 2016/0170481 A1 | 6/2016 | Fateh | |
| 2016/0173752 A1* | 6/2016 | Caviedes | ........... H04N 1/00204 348/207.11 |
| 2016/0270656 A1 | 9/2016 | Samec | |
| 2016/0367165 A1 | 12/2016 | Khaderi | |
| 2016/0370591 A1 | 12/2016 | Wilson | |
| 2017/0097449 A1 | 4/2017 | Ouderkirk | |
| 2017/0127055 A1 | 5/2017 | Khabiri | |
| 2017/0140223 A1 | 5/2017 | Wilson | |
| 2017/0140224 A1 | 5/2017 | Wilson | |
| 2017/0150881 A1 | 6/2017 | Khaderi | |
| 2017/0293356 A1 | 10/2017 | Khaderi | |
| 2019/0391638 A1 | 12/2019 | Khaderi | |
| 2022/0099966 A1 | 3/2022 | Khaderi | |

FOREIGN PATENT DOCUMENTS

| | | |
|---|---|---|
| WO | 2009091845 A1 | 7/2009 |
| WO | 2015003097 | 1/2015 |
| WO | 2015198477 A1 | 12/2015 |
| WO | 2015198502 A1 | 12/2015 |
| WO | 2016021034 A1 | 2/2016 |
| WO | 2016103525 A1 | 6/2016 |

OTHER PUBLICATIONS

Glenberg, Arthur A.; Schroeder, Jennifer L.; and Robertson, David A.; "Averting the gaze disengages the environment and facilitates remembering", Memory & Cognition 1998,26 (4),651-658.

R.N. Khushaba et al. / ""Consumer neuroscience: Assessing the brain response to marketing stimuli using electroencephalogram (EEG) and eye tracking""/Expert Systems with Applications 40 (2013) 3803-3812.

Knoblich et al. "An eye movement study of insight problem solving", Memory & Cognition 2001, 29 (7), 1000-1009.

Kok, Albert; "Event-related-potential (ERP) reflections of mental resources: a review and synthesis", Biological Psychology 45 (1997) 19-56.

Krajbich, Ian et al., "Visual fixations and the computation and comparison of value in simple choice", Nat. Neurosci. 13, 1292-1298 (2010); published online Sep. 12, 2010; corrected after print Feb. 10, 2011.

(56) References Cited

OTHER PUBLICATIONS

Lal, Saroj K.L. and Craig, Ashley, "Driver Fatigue: Electroencephalography and psychological assessment", Psychophysiology, 39 ~2002!, 313-321. Cambridge University Press.
Liversedge, Simon P. and Findlay, John M.; "Saccadic eye movements and cognition", Trends in Cognitive Sciences, vol. 4, No. 1, Jan. 2000, pp. 6-13.
O'Keefe, Paul A et al., "Learning from multiple representations: An examination of fixation patterns in a science simulation", Computers in Human Behavior 35 (2014) 234-242.
Osterhout, Lee and Holcomb, Phillip, "Event-Related Potentials and Language Comprehension", Based on Chapter 6 in Rugg, M. D., & Coles, M. G. H. Electrophysiology of mind: Event-related brain potentials and cognition. Oxford University Press, 1995.
Paas, Fred et al.; "Cognitive Load Measurement as a Means to Advance Cognitive Load Theory", Educational Psychologist, 38(1), 63-71, Mar. 2003.
Borbely, Alexander; Baumann, Fritz; Brandeis, Daniel; Strauch, Inge; and Lehmann, Dietrich; "Sleep Deprivation: Effect on Sleep Stages and EEG Power Density in Man"; Electroencephalography and Clinical Neurophysiology, 1981,51:483-493.
Richardson, Daniel C. and Dale, Rick; "Looking To Understand: The Coupling Between Speakers' and Listeners' Eye Movements and Its Relationship to Discourse Comprehension", Cognitive Science 29 (2005) 1045-1060.
Rozin, Paul and Cohen, Adam B; "High Frequency of Facial Expressions Corresponding to Confusion, Concentration, and Worry in an Analysis of Naturally Occurring Facial Expressions of Americans", Emotion, American Psychological Association, 2003, vol. 3, No. 1, 68-75.
Shultz, Sarah et al., "Inhibition of eye blinking reveals subjective perceptions of stimulus salience", PNAS, vol. 108, No. 52, (Dec. 27, 2011), pp. 21270-21275.
Simion, Claudiu and Shimojo, Shinsuke, "Interrupting the cascade: Orienting contributes to decision making even in the absence of visual stimulation", Perception & Psychophysics 2007, 69 (4), 591-595.
Smilek, Daniel et al.; "Out of Mind, Out of Sight : Eye Blinking as Indicator and Embodiment of Mind Wandering", Psychological Science published online Apr. 7, 2010, http://pss.sagepub.com/content/early/2010/04/07/0956797610368063.
Fiedler, Susann and Glockner, Andreas; "The dynamics of decision making in risky choice: an eye-tracking analysis", Frontiers in Psychology, Cognitive Science, vol. 3, Article 335, (Oct. 2012).
Sutherland, I. E. "A head-mounted three dimensional display", Proceedings of the Dec. 9-11, 1968, fall joint computer conference, part I (pp. 757-764). ACM.
Cobb, S. V., Nichols, S., Ramsey, A., & Wilson, J. R. "Virtual reality-induced symptoms and effects (VRISE)". Presence, 8(2), (1999), pp. 169-186.
Smith, T., & Guild, J. "The CIE colorimetric standards and their use", Transactions of the Optical Society, 33(3), (1931), p. 73.
Robertson, A. R. The CIE 1976 Color☐Difference Formulae. Color Research & Application, 2(1), (1977), pp. 7-11.
Boucheix, Jean-Michel and Lowe, Richard K.; "An eye tracking comparison of external pointing cues and internal continuous cues in learning with complex animations", Learning and Instruction 20 (2010) 123-135.
Krauskopf, J., Williams, D. R., & Heeley, D. W. "Cardinal directions of color space", Vision research, 22(9), (1982), pp. 1123-1131.

Hoffman, et al. :Virtual Reality Helmet Display Quality Influences the Magnitude of Virtual Realtiy Analgesia, The Journal of Pain, vol. 7, No. 11 Nov. 2006: pp. 843-850.
Desouza et al., "Preparatory Set Associated with Pro-Saccades and Anti-Saccades in Humans Investigated with Event-Related MRI", J Neurophysiol 89: 1016-1023, 2003.
Khaderi, Khizer et al. "The Visual Effects Associated with Head-Mounted Displays: A Meta-Analysis and Systematic Review".
Raaen, Kjetil and Kjellmo, Ivar; "Measuring Latency in Virtual Reality Systems", K. Chorianopoulos et al. (Eds.): ICEC 2015, LNCS 9353, pp. 457-462, 2015.
Khaderi, Khizer et al.; "Methods to Reduce Visual Sickness in Design of New VR Services", Journal of Digital Video, Society of Cable Telecommunications Engineers, Inc. (2016), pp. 5-16.
Ganin et al; "DeepWarp: Photorealistic Image Resynthesis for Gaze Manipulation", Skolkovo Institute of Science and Technology, Jul. 25, 2016.
Gaidon et al; "VirtualWorlds as Proxy for Multi-Object Tracking Analysis", May 20, 2016; http://www.xrce.xerox.com/Research-Development/Computer-Vision/Proxy-Virtual-Worlds.
Sharples, S. et al. "Virtual reality induced symptoms and effects (WRISE): Comparison of head mounted display (HMD), desktop and projection display systems", Displays 29 (2008) 58-69.
Krauskopf, John, "A Journey in Color Space", Verriest Lecture, Center for Neural Science, Supplement vol. 26, (2001), S1-S11.
Dinges, David F. and Powell, John W.; Microcomputer analyses of performance on a portable, simple visual RT task during sustained operations, Behavior Research Methods, Instruments, & Computers 1985, 17 (6), 652-655.
Fairman, Hugh S., "How the CIE 1931 Color-Matching Functions Were Derived from Wright-Guild Data", Transactions of the Optical Society, vol. 22, No. 1, Feb. 1997, pp. 11-23, Erratum in vol. 23, No. 4, Aug. 1998, p. 259.
Shi, Y., Ruiz, N., Taib, R., Choi, E., & Chen, F. (Apr. 2007). Galvanic skin response (GSR) as an index of cognitive load. In CHI'07 extended abstracts on Human factors in computing systems (pp. 2651-2656). ACM.
Miltner, W. H., Braun, C., Arnold, M., Witte, H., & Taub, E. (1999). Coherence of gamma-band EEG activity as a basis for associative learning. Nature, 397(6718), 434-436.
Toda, I., Fujishima, H., & Tsubota, K. (1993). Ocular fatigue is the major symptom of dry eye. Acta ophthalmologica, 71(3), 347-352.
Gebrehiwot, Temesgen; Paprocki, Rafal; and Lenskiy, Artem; "Analysis of Blink Rate Variability during reading and memory testing", Preprint, Mar. 2016.
Glaholt, Mackenzie; Wu, Mei-Chun; and Reingold, Eyal M.; "Predicting preference from fixations", PsychNology Journal, 2009 vol. 7, No. 2, 141-158.
International Search Report for PCT/US2017/026688, Jul. 19, 2017.
International Search Report for PCT/US2017/026689, Jul. 21, 2017.
Portello et al., "Blink Rate, Incomplete Blinks and Computer Vision Syndrome", Optometry and Vision Science, vol. 90, No. 5, pp. 782-487, May 2013.
Schleicher et al., "Blinks and saccades as indicators of fatigue in sleepiness warners: looking tired?" Ergonomics, Aug. 2008.
Watten et al., "The Influence of Long-Term Visual Near-Work on Accommodation and Vergence: A Field Study", J. Human Ergol., 23: 27-39, 1994.
International Search Report for PCT/US09/31024, Jun. 30, 2009.
Written Opinion of the International Searching Authority for PCT/US09/31024, Jun. 30, 2009.

* cited by examiner

| Afferent Source (Stimulus) (1) | Stimulus Event (2) | Stimulus Feature (3) | Efferent Source (Response) | Response Event | Response Feature | Psychometric Measure | Description |
|---|---|---|---|---|---|---|---|
| Display / Visual Environment | (any) | Position | Eye Tracking | Pro-Saccade (towards target) | Position | Detection | Saccade towards target (detected) or saccade elsewhere or no saccade (not detected) |
| Display / Visual Environment | (any) | Identity | Eye Tracking | Pro-Saccade (towards target) | Position | Accuracy (choice) | Saccade towards the correct object (correct) and not towards a distractor (incorrect) |
| Display / Visual Environment | (any) | Position | Eye Tracking | Pro-Saccade (towards target) | Position | Accuracy (position) | Error between saccade landing point and desired (target) (in polar coordinates) |
| Display / Visual Environment | (any) | Position | Eye Tracking | Pro-Saccade (towards target) | Velocity | Accuracy | Initial velocity (speed and direction) of saccade from a fixation |
| Display / Visual Environment | (any) | (any) | Eye Tracking | Pro-Saccade (towards target) | Timing | Reaction | Reaction Time - delay between stimulus event and response event |
| Display / Visual Environment | (any) | Position | Eye Tracking | Anti-Saccade (away from target) | Position | Detection | Saccade (directly) away from target (detected) or saccade elsewhere or no saccade (not detected) |
| Display / Visual Environment | (any) | Identity | Eye Tracking | Anti-Saccade (away from target) | Position | Accuracy (choice) | Saccade away from the correct object (correct) and not towards it or some orthogonal direction (incorrect) |
| Display / Visual Environment | (any) | Position | Eye Tracking | Anti-Saccade (away from target) | Position | Accuracy (position) | Error between saccade landing point and desired (opposite from target) (in polar coordiantes) |
| Display / Visual Environment | (any) | Position | Eye Tracking | Anti-Saccade (away from target) | Velocity | Accuracy | Initial velocity (speed and direction) of saccade from fixation |
| Display / Visual Environment | (any) | (any) | Eye Tracking | Anti-Saccade (away from target) | Timing | Reaction | Reaction Time - delay between stimulus event and response event |
| (any) | (any) | (any) | Eye Tracking | Microsaccades | Frequency/ Amplitude | Autonomic / Fatigue | Monitoring of microsaccade rates (during fixation) over time |

FIG. 14

| Stimulus Source | Stimulus Attribute | Stimulus Property | Response Modality | Response Type | Response Attribute | Response Measure | Description |
|---|---|---|---|---|---|---|---|
| Display / Visual Environment | (any) | Position | Eye Tracking | Saccade | Position | Inhibition of return | Tendency to avoid saccades to recently fixated locations |
| Display / Visual Environment | Object Motion | Position / Path | Eye Tracking | Pursuit: Moving Target | Position | Accuracy (position) | Positional error between gaze position and moving object position (also as a function of target speed) |
| Display / Visual Environment | Object Motion | Timing | Eye Tracking | Pursuit: Moving Target | Timing | Reaction | Reaction Time - delay between stimulus appearance / motion onset and pursuit onset |
| Display / Visual Environment | (any) | Position | Eye Tracking | Pursuit: Moving Target | Position | Accuracy / Coordination | Positional error between gaze position and still object during head motion |
| (any) | (any) | (any) | Eye Tracking | Pursuit-Saccade Pattern | Position | Dizziness | Mismatch between vestibular and visual inputs during dizziness causes eyes to follow a saw-tooth pattern of pursuit (tracking phantom head motion) and saccade (correction) |
| Display / Visual Environment | (any) | Position (depth) | Eye Tracking | Vergence | Position (vergence) | Accuracy (position) | Ability of eyes to converge or diverge in response to object depth |
| Display / Visual Environment | (any) | (any) | Eye Tracking | Multiple Saccades | Positions | Pattern | Pattern of saccades (i.e. during visual search) |
| Display / Visual Environment | (any) | Identity | Eye Tracking | Blink | Timing | Reaction | Blink in response to discrete visual stimulus event (e.g. reflexive blink) |
| Sound / Audio Environment | (any) | Identity | Eye Tracking | Blink | Timing | Reaction | Blink in response to discrete audio stimulus event (e.g. reflexive blink) |
| (any) | (any) | (any) | Eye Tracking | Blinks | Frequency | Autonomic / Fatigue | Blink rate over time - potentially correlated with state |
| Display / Visual Environment | (any) | Identity | Eye Tracking | Pupil Size | Timing | Reaction | Pupil size change in response to discrete visual stimulus event |

FIG. 14 (Cont.)

| Sound / Auditory Environment | | Eye Tracking | Pupil Size | Timing | Reaction | Pupil size change in response to discrete audio stimulus event |
|---|---|---|---|---|---|---|
| (any) | Identity | Eye Tracking | Pupil Size | Timing | Reaction | Pupil size change in response to discrete audio stimulus event |
| (any) | (any) | Eye Tracking | Pupil Size | Temporal Mean | Autonomic / Fatigue | Pupil size over time (central tendency and variability) |
| Display / Visual Environment | (any) | Head Tracking | Orientation (discrete) | Position | Detection | Orientation towards target (detected) or away or no orientation (not detected) |
| Display / Visual Environment | (any) | Head Tracking | Orientation (discrete) | Position | Accuracy (choice) | Orient towards the correct object (correct) and not towards a distractor (incorrect) |
| Display / Visual Environment | (any) | Head Tracking | Orientation (discrete) | Position | Accuracy (position) | Error between orientation and desired (evidenced by small, error-correcting motions following) |
| Display / Visual Environment | (any) | Head Tracking | Orientation (discrete) | Timing | Reaction | Reaction Time - delay between stimulus event and response event |
| Display / Visual Environment | (any) | Head Tracking | Tracking | Position | Accuracy | Positional error between head pointing and moving object position (also as a funtion of target speed) |
| Display / Visual Environment | Object Motion | Head Tracking | Tracking | Timing | Reaction | Reaction Time - delay between stimulus appearance / motion onset and pursuit onset |
| Display / Visual Environment | Position / Path | Manual (Cursor) | Click / Touch | Position | Detection | Click at target location (detected) or click elsewhere or no click (not detected) |
| Display / Visual Environment | (any) | Manual (Cursor) | Click / Touch | Position | Accuracy (choice) | Click at correct target (correct) and not at incorrect (distractor) object (incorrect) |
| Display / Visual Environment | Identity | Manual (Cursor) | Click / Touch | Position | Accuracy (position) | Error between click position and object position |
| Display / Visual Environment | (any) | | | | | |

FIG. 14 (Cont.)

| | | | | | | |
|---|---|---|---|---|---|---|
| Display / Visual Environment | (any) | Manual (Cursor) | Click / Touch | Timing | Reaction | Reaction Time - delay between stimulus event and response event |
| Display / Visual Environment | (any) | Manual (Cursor) | Click / Touch (pressure) | Pressure | Pressure | Pressure of touch (likely proportional with reaction time and able to correlate with confidence of response / accuracy |
| Display / Visual Environment | (any) | Manual (Cursor) | Click / Touch (multitouch) | Position (multi) | Multi-tracking | May be used to differentiate response type, but also has potential for multi-tracking |
| Display / Visual Environment | Object Motion | Manual (Cursor) | Tracking (pursuit) | Position | Accuracy (position) | Positional error between cursor position and moving object position (also as a function of target speed) |
| Display / Visual Environment | Object Motion | Manual (Cursor) | Tracking (pursuit) | Timing | Reaction | Reaction Time - delay between stimulus appearance / motion onset and pursuit onset |
| (any) | (any) | Manual (Direction Pad) | Direction Pad | Direction | Accuracy | Indicating direction on a direction pad / joystick Accuracy of direction (up/down/left/right or angle, depending on source) |
| (any) | Timing | Manual (Direction Pad) | Direction Pad | Timing | Reaction | Reaction Time - delay between stimulus event and response event |
| (any) | (any) | Manual (Scroll) | Scroll | Direction | Accuracy | Scroll direction indicating up/down |
| (any) | Timing | Manual (Scroll) | Scroll | Timing | Reaction | Reaction Time - delay between stimulus event and response event |
| (any) | (any) | Manual (Swipe) | Swipe | Direction | Accuracy | Swipe direction indicating up/down |
| (any) | Timing | Manual (Swipe) | Swipe | Timing | Reaction | Reaction Time - delay between stimulus event and response event |

FIG. 14 (Cont.)

| | | | | Gesture | Gesture | | |
|---|---|---|---|---|---|---|---|
| (any) | (any) | (any) | Gesture Tracking | | | (any) | Gesture identification through video or other motion capture |
| (any) | (any) | (any) | Electrophysiological (EEG) | Time-Locked Mean Response | Waveform | Waveform | Event related potentials (as in voltage potential) to stimuli: Visual evoked potentials, Auditory evoked potentials, Cognitive potentials |
| (any) | (any) | (any) | Electrophysiological (EEG) | Temporal (Frequency Tagged) | Rates | Autonomic / Brain State | Measures of autonomic or brain state over time or in response to stimulus events |
| (any) | (any) | Display / Visual Environment | Electrophysiological (EOG) | Saccade (Pro-Anti-) | Position / Timing | (any) | (Similar to eye tracking, but with better temporal and worse positional accuracy) |
| (any) | (any) | Display / Visual Environment | Electrophysiological (EOG) | Pursuit | Position / Timing | (any) | (Similar to eye tracking, but with better temporal and worse positional accuracy) |
| (any) | (any) | Display / Visual Environment | Electrophysiological (EOG) | Microsaccades | Frequency / Amplitude | Autonomic / Fatigue | Monitoring of microsaccade rates (during fixation) over time |
| (any) | (any) | (any) | Electrophysiological (ECG) | Temporal (Frequency Tagged) | Rates | Autonomic / Fatigue | Monitoring of heart rate over time |
| (any) | (any) | (any) | Galvanic Skin Response | Time-Locked Mean Response | Waveform | Waveform | Skin conductance response to stimulus events |
| (any) | (any) | (any) | Galvanic Skin Response | Temporal (Frequency Tagged) | Rates | Autonomic / Fatigue | Skin conductance response over time |
| (any) | (any) | (any) | Pulse Oximetry | Temporal | Rates | Autonomic / Fatigue | Oxygen saturation over time |
| (any) | (any) | (any) | Respiration | Temporal | Rates | Autonomic / Fatigue | Respiration rate over time or in response to stimulus events |
| (any) | (any) | (any) | Blood Pressure | Temporal | Rates | Autonomic / Fatigue | Blood pressure over time or in response to stimulus events |

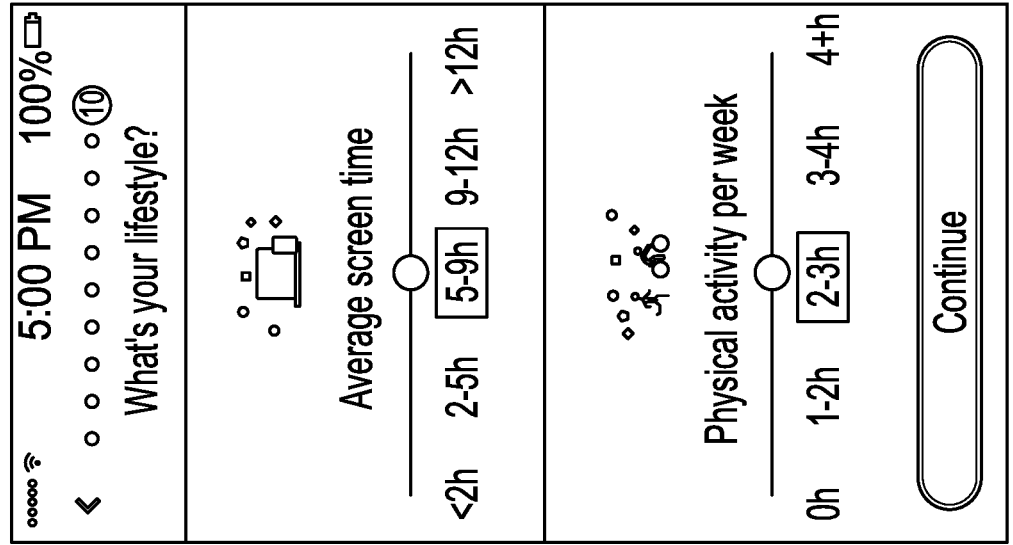
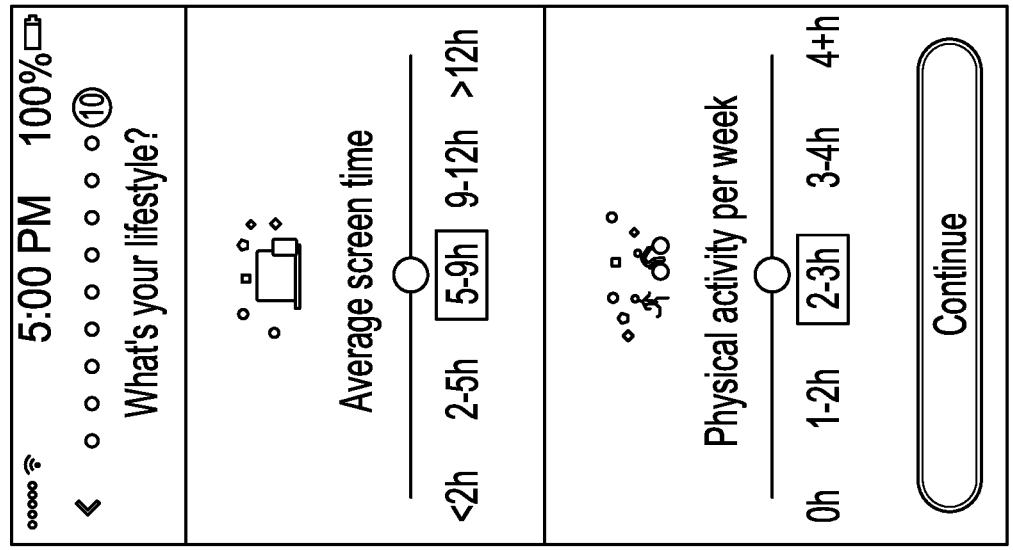
FIG. 21C

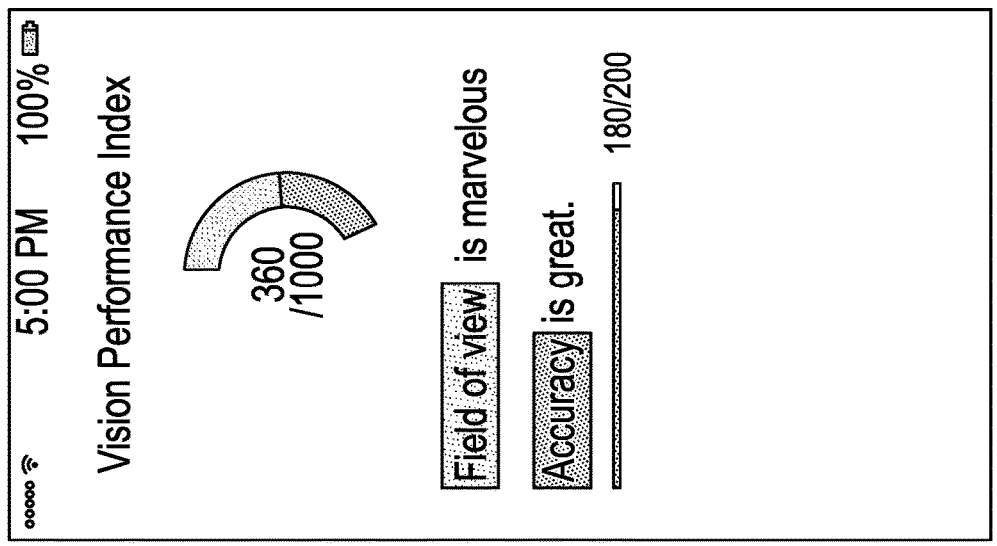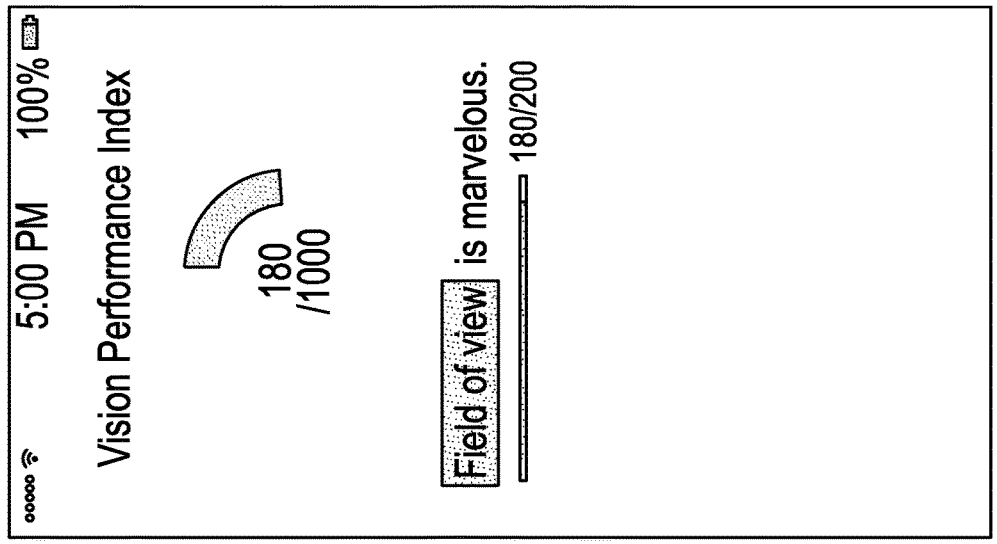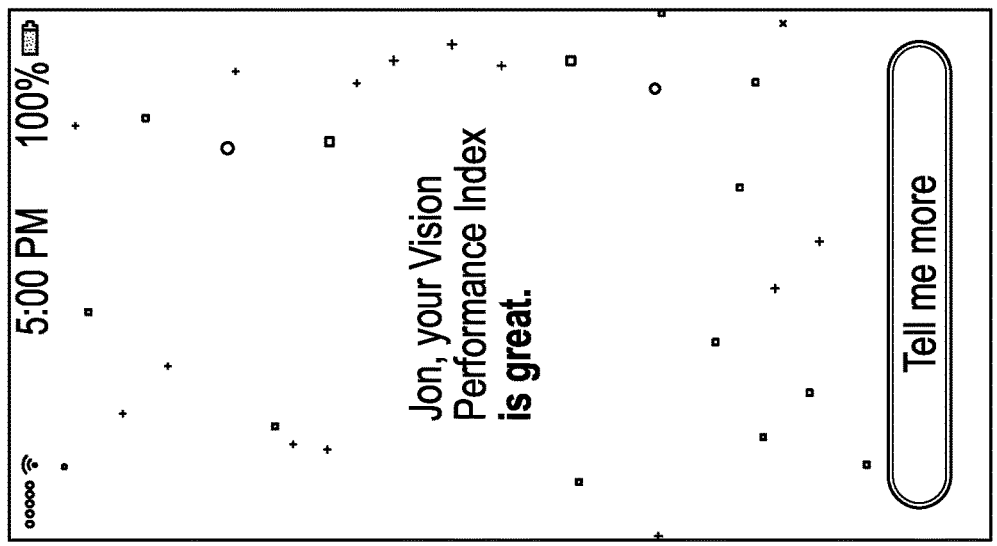
FIG. 22

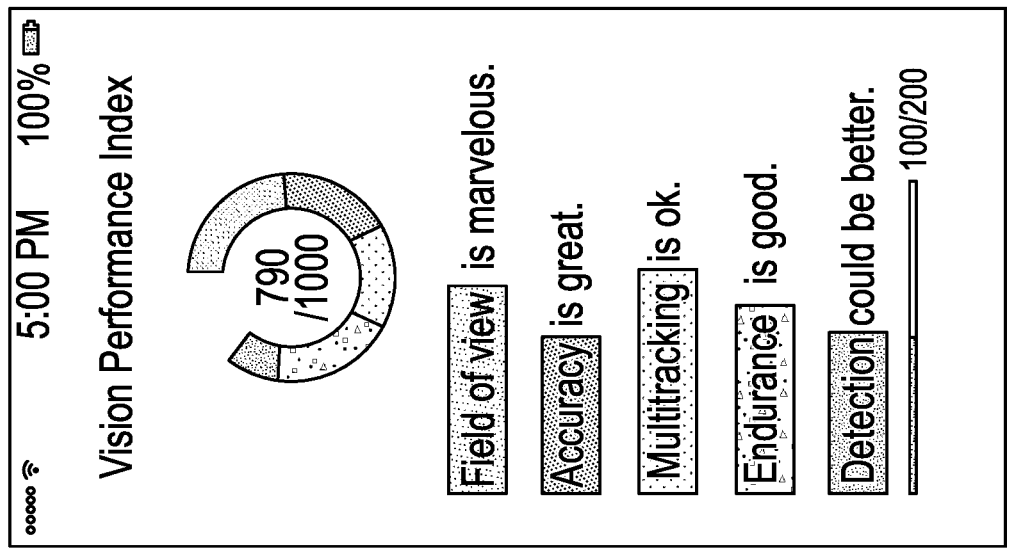
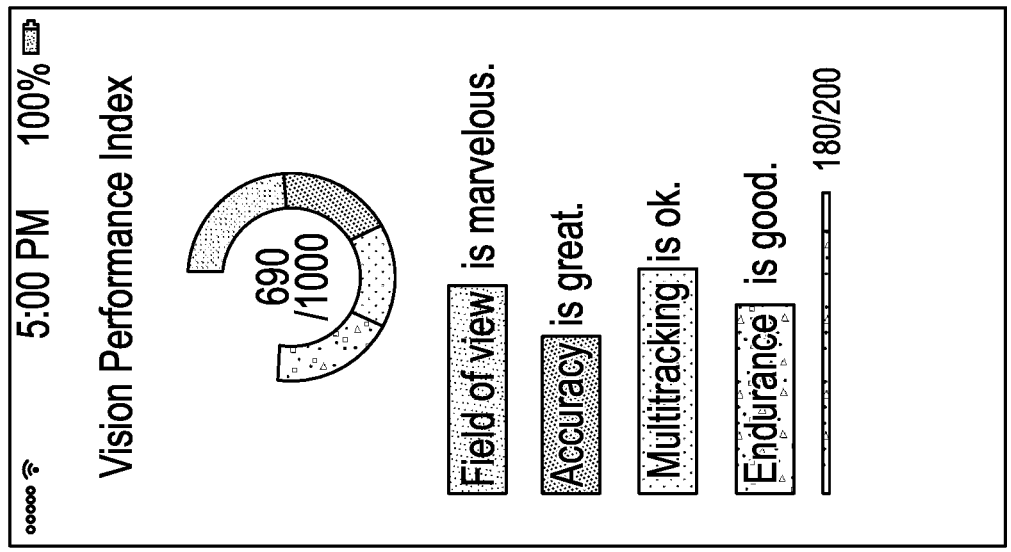
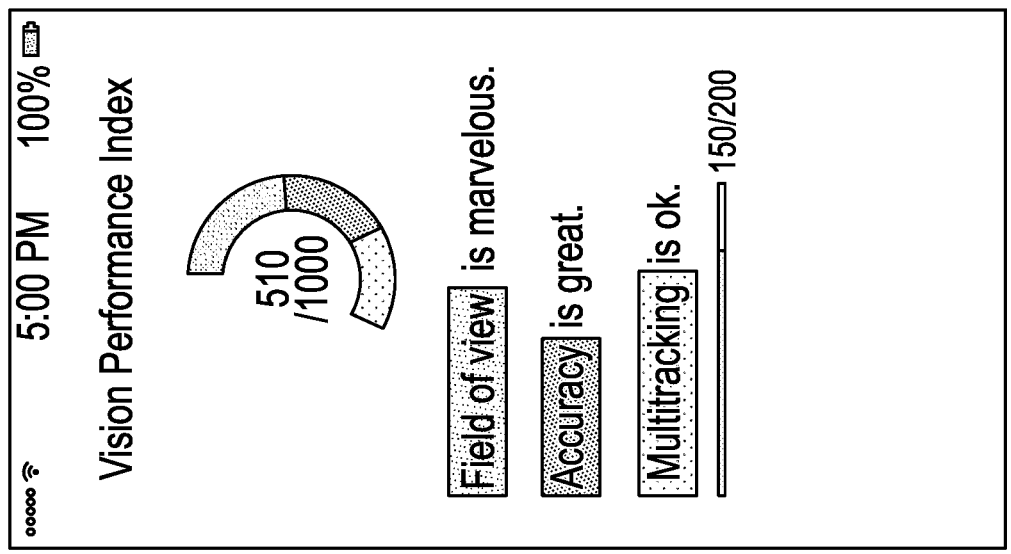
FIG. 22 (Cont.)

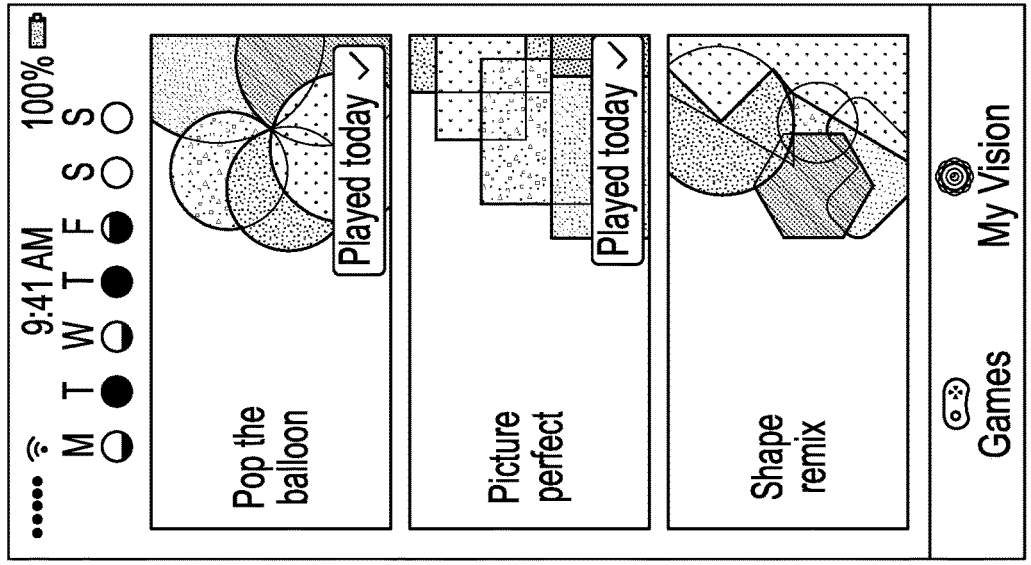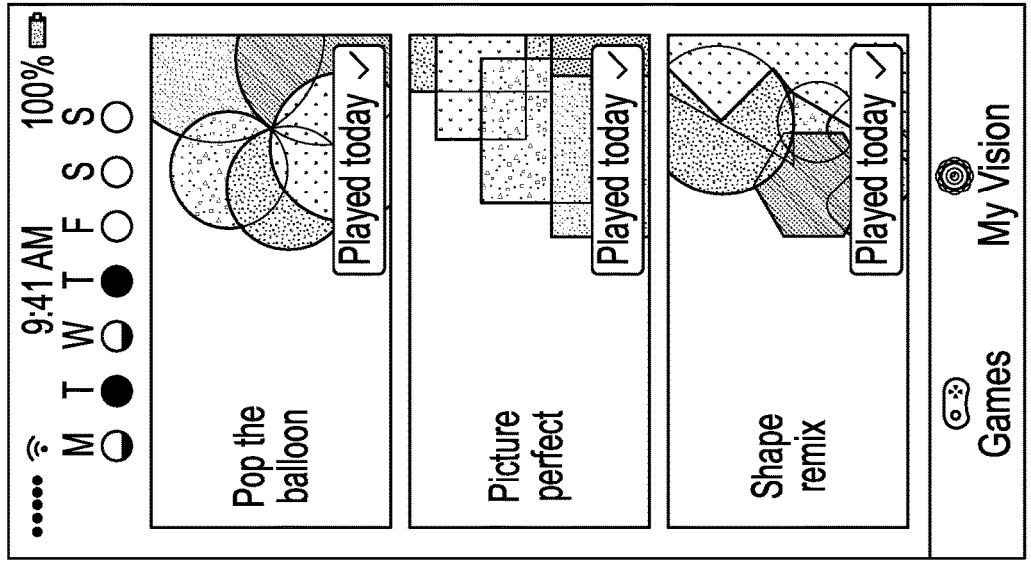
FIG. 23 (Cont.)

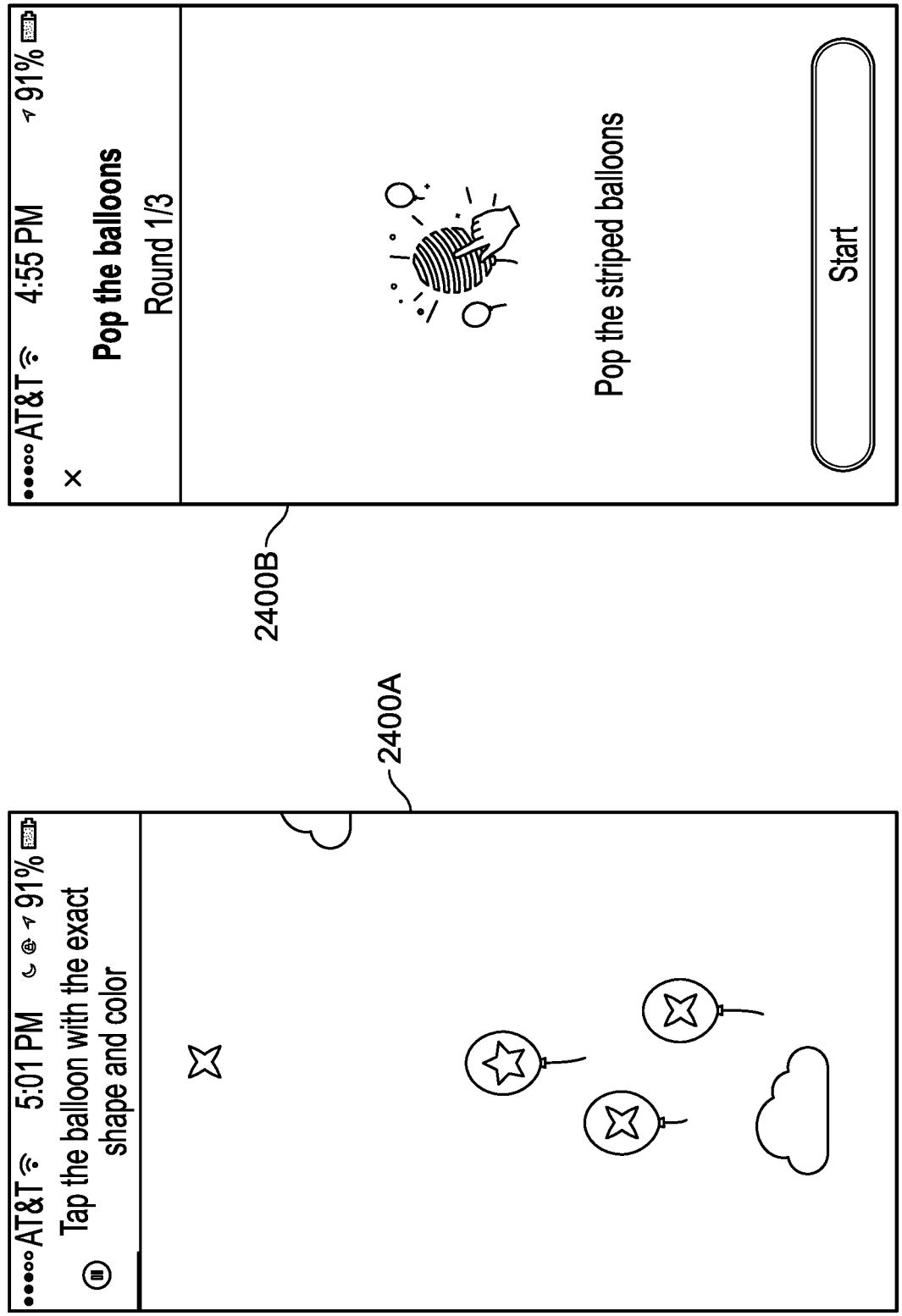

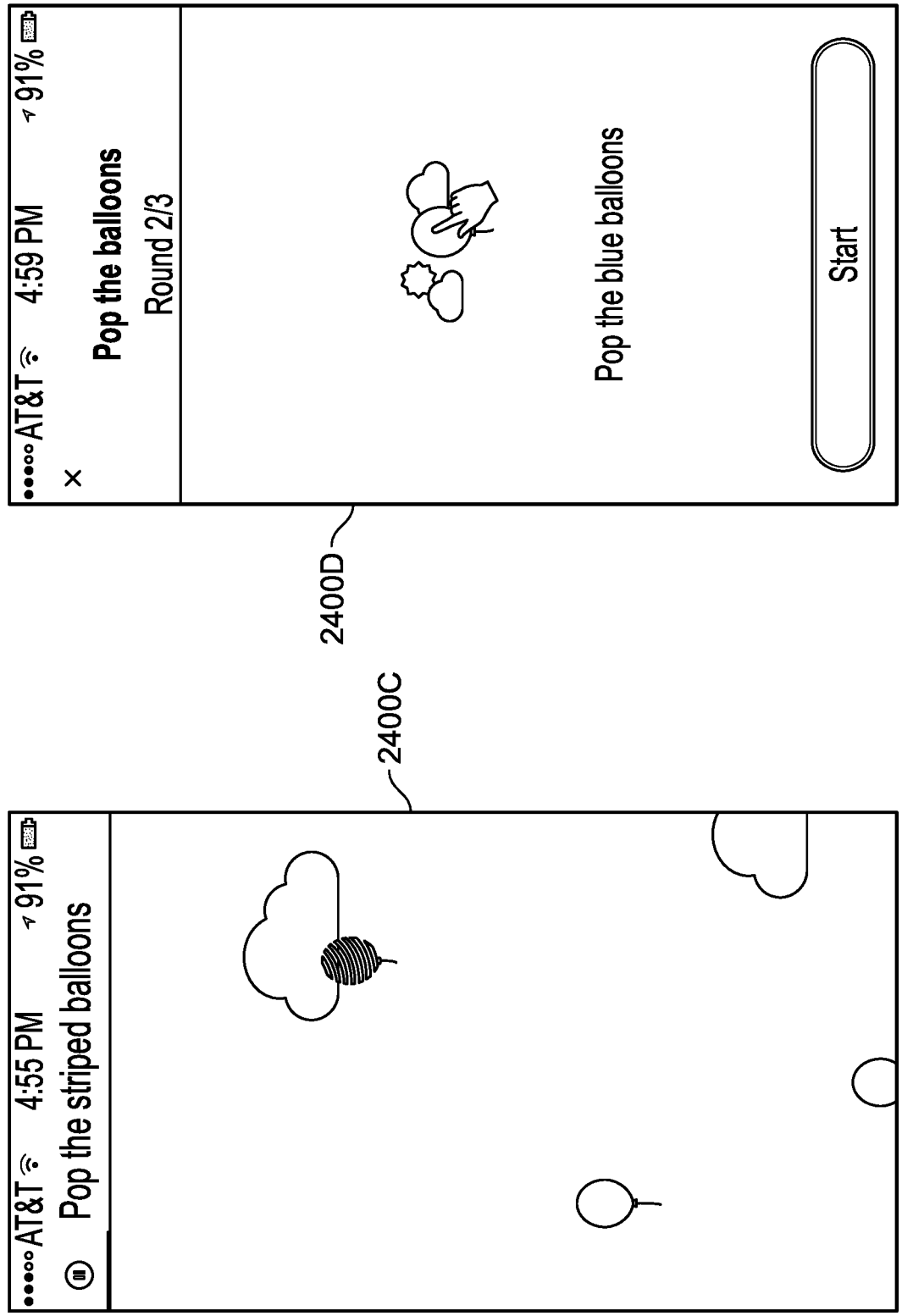

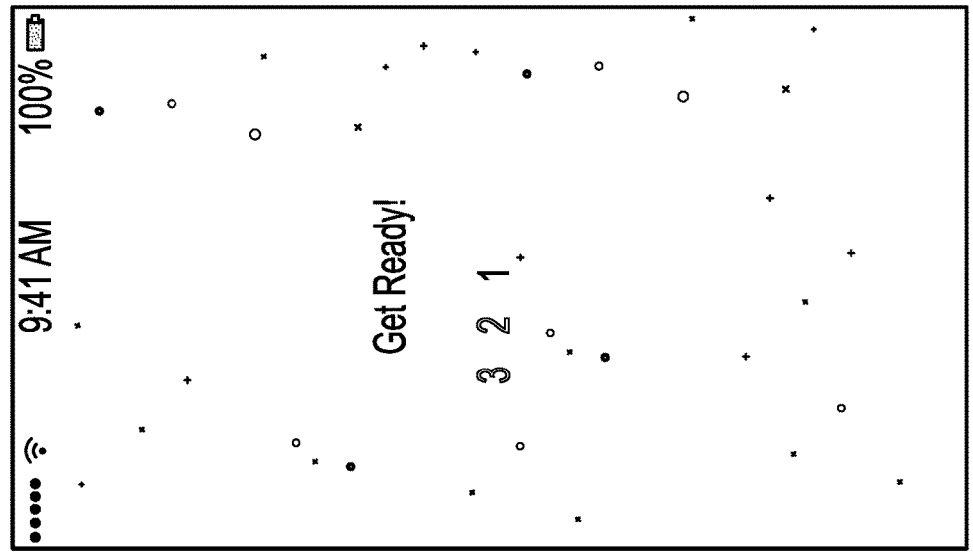
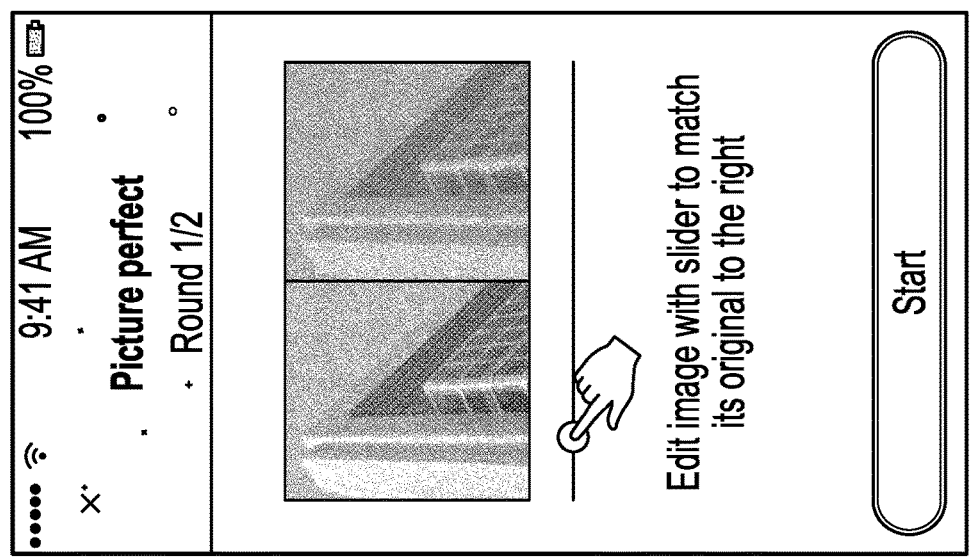
FIG. 25A

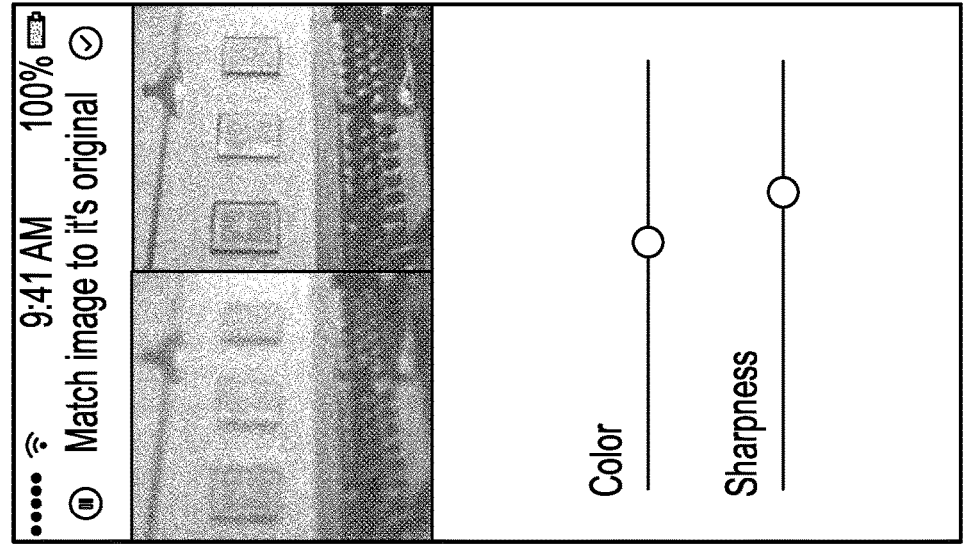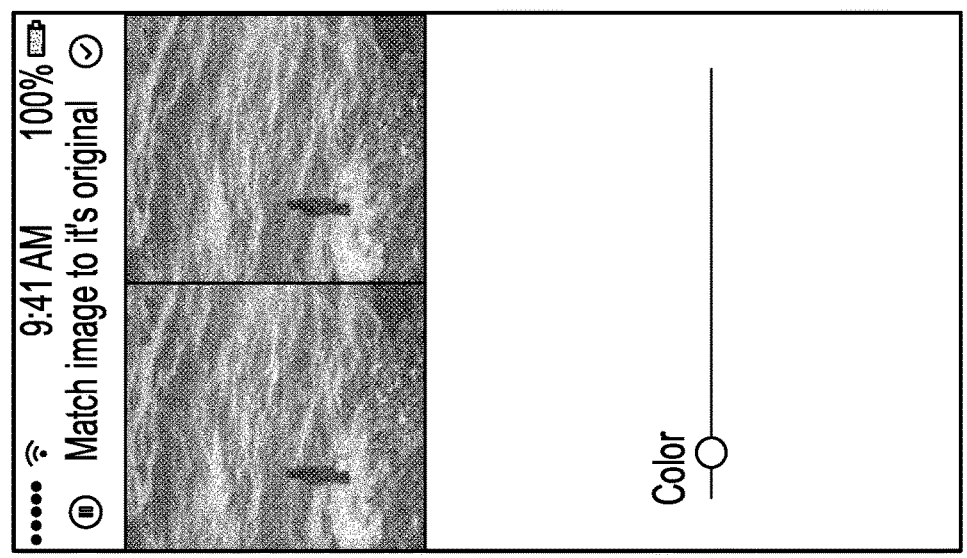
FIG. 25A (Cont.)

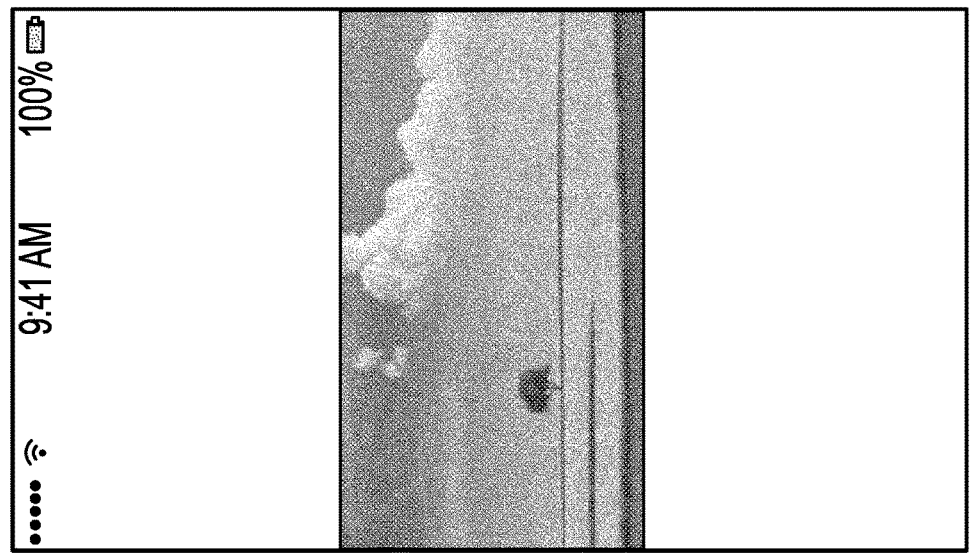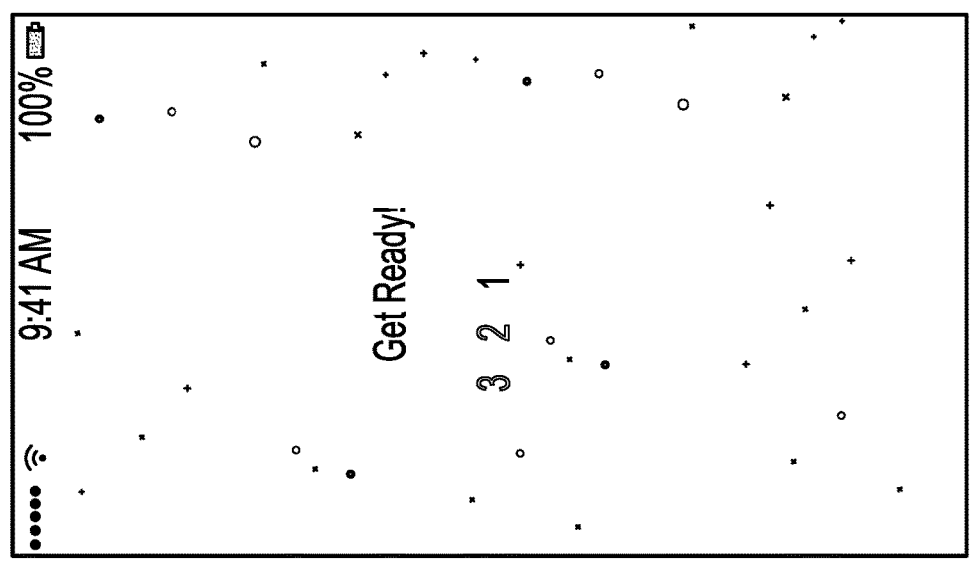
FIG. 25D

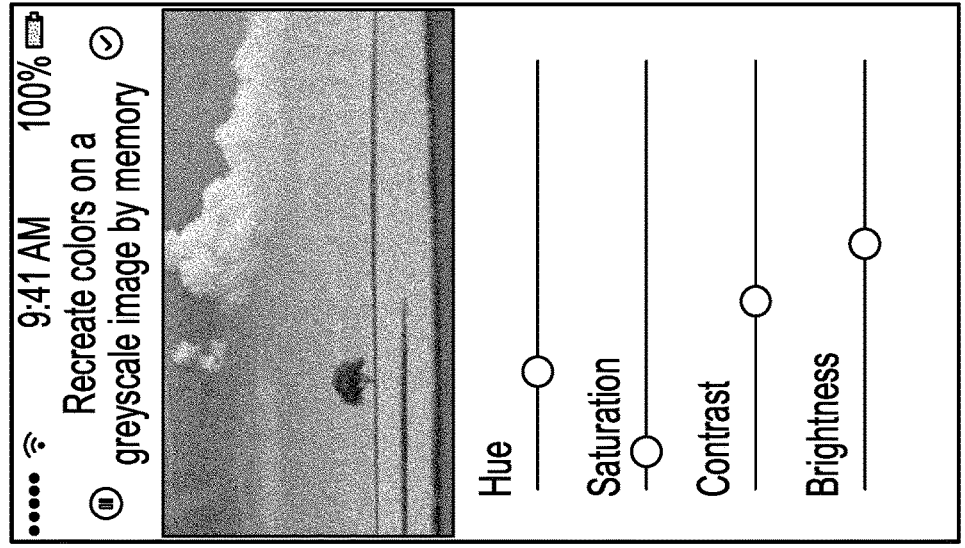
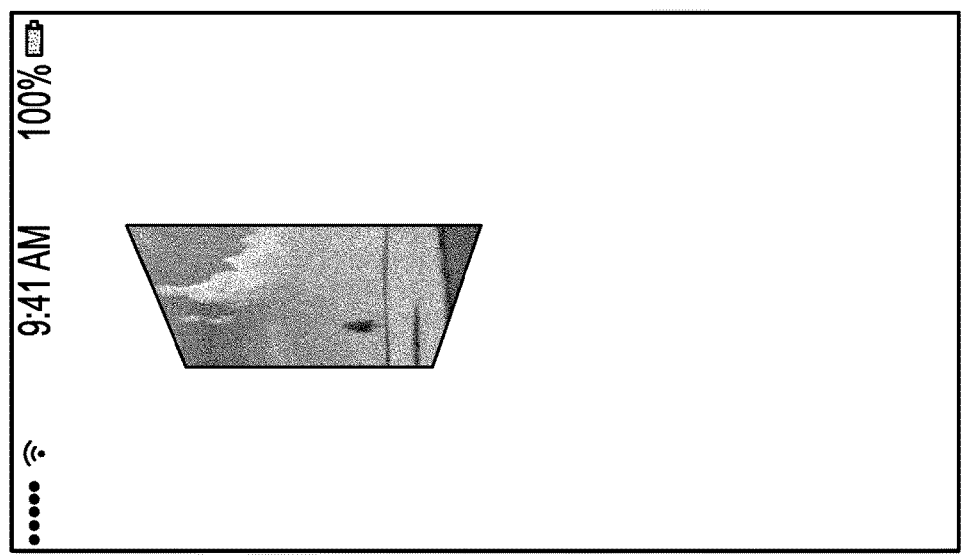
FIG. 25D (Cont.)

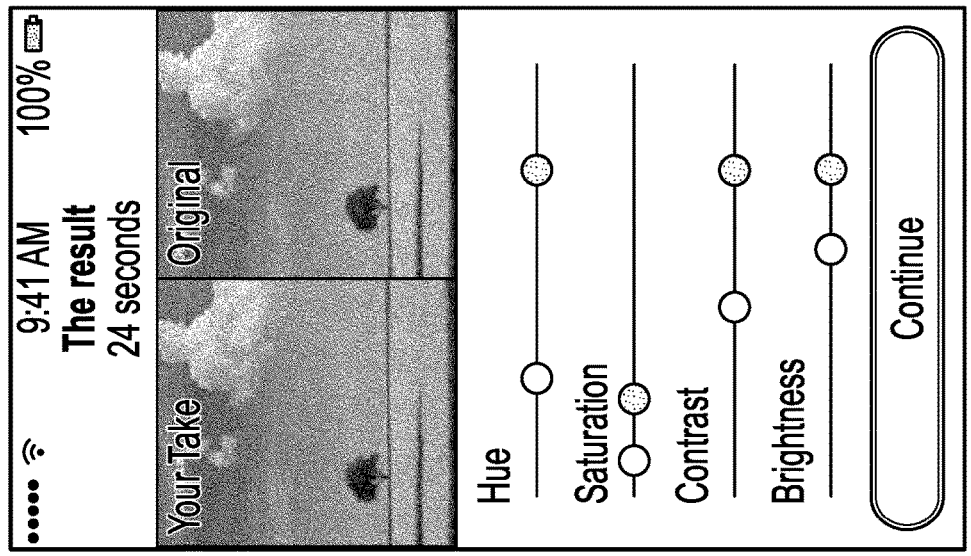
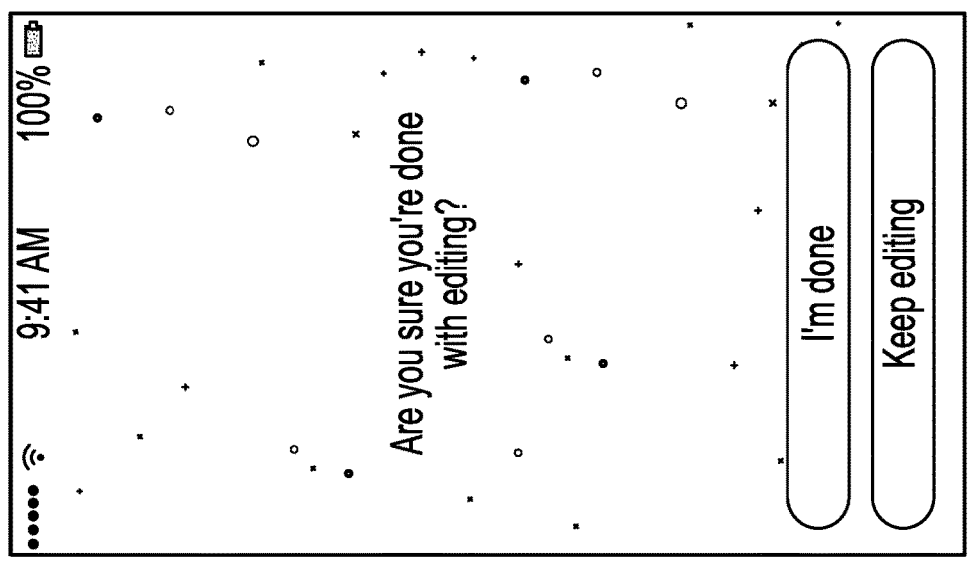
FIG. 25E

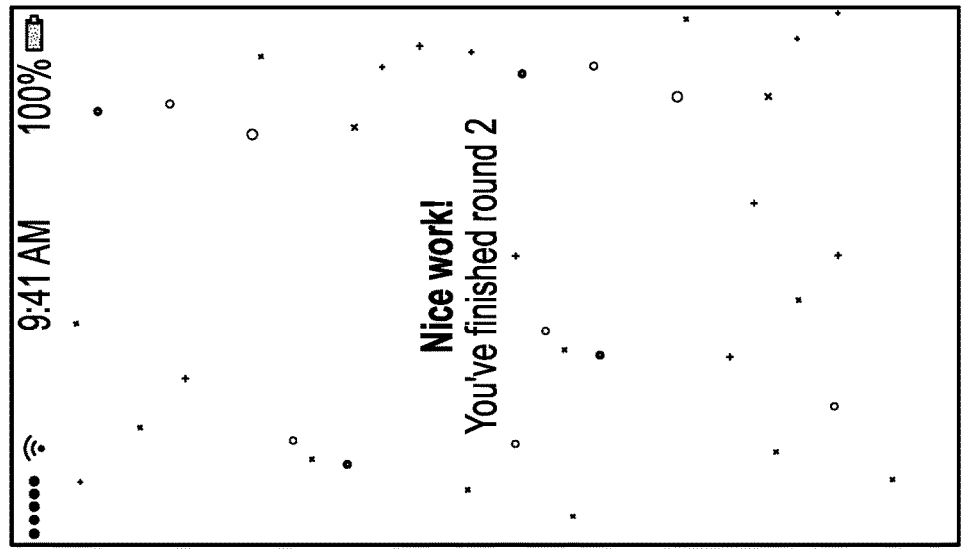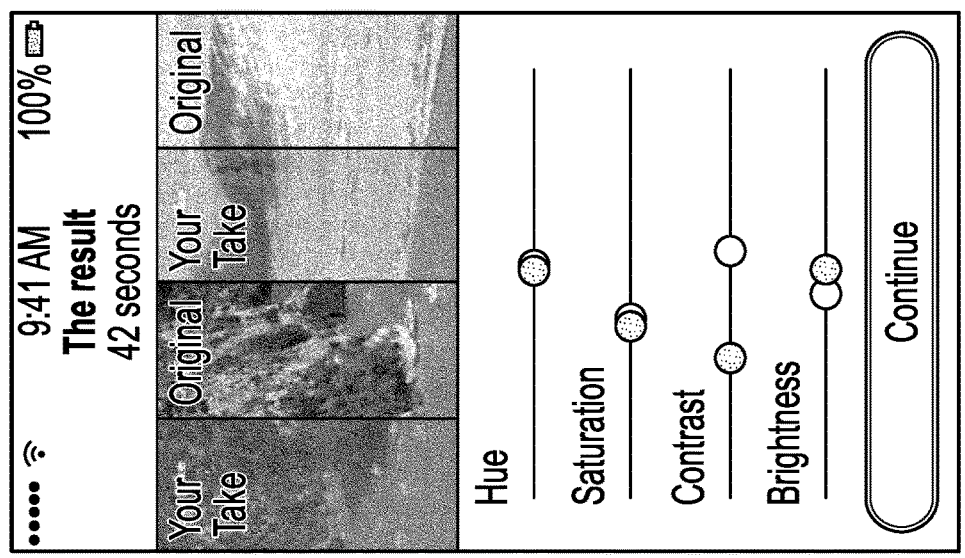
FIG. 25E (Cont.)

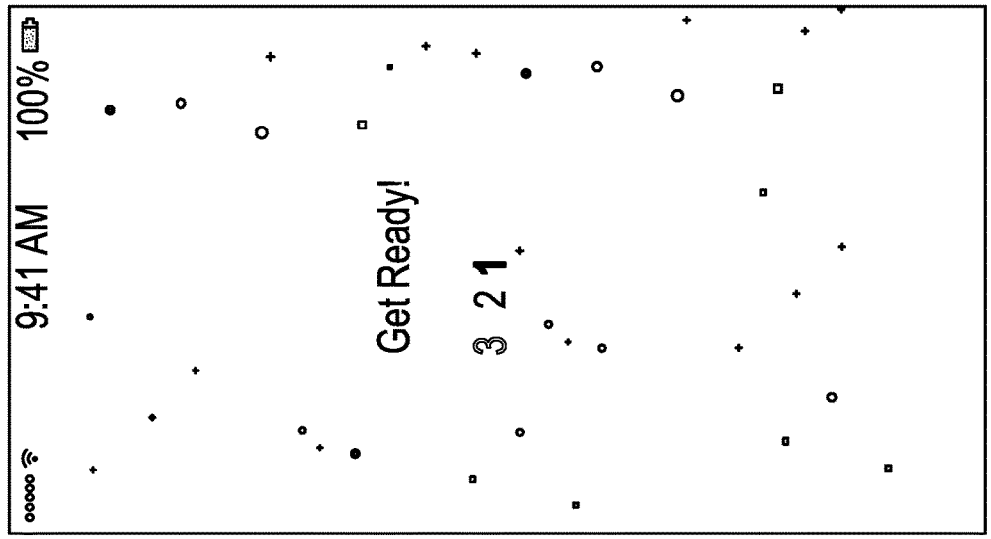
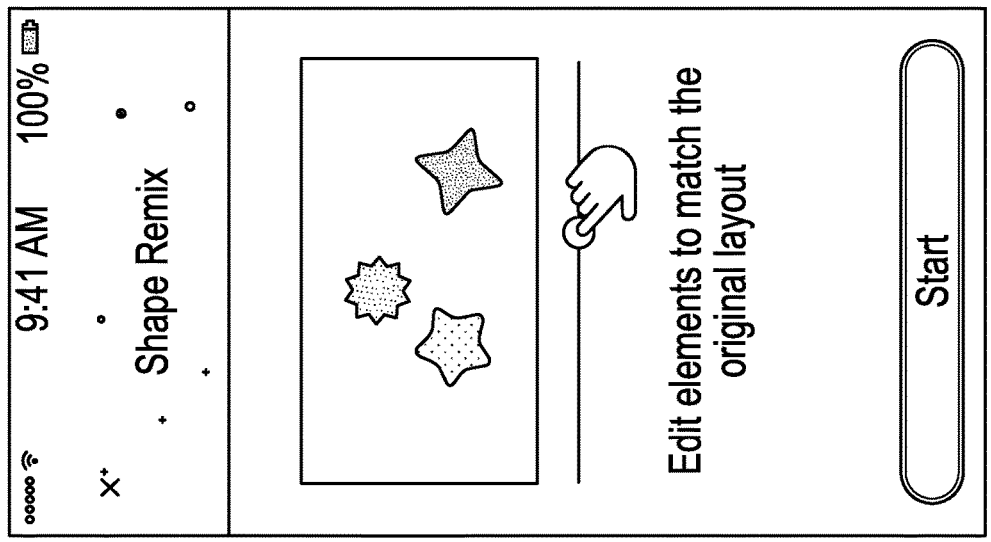
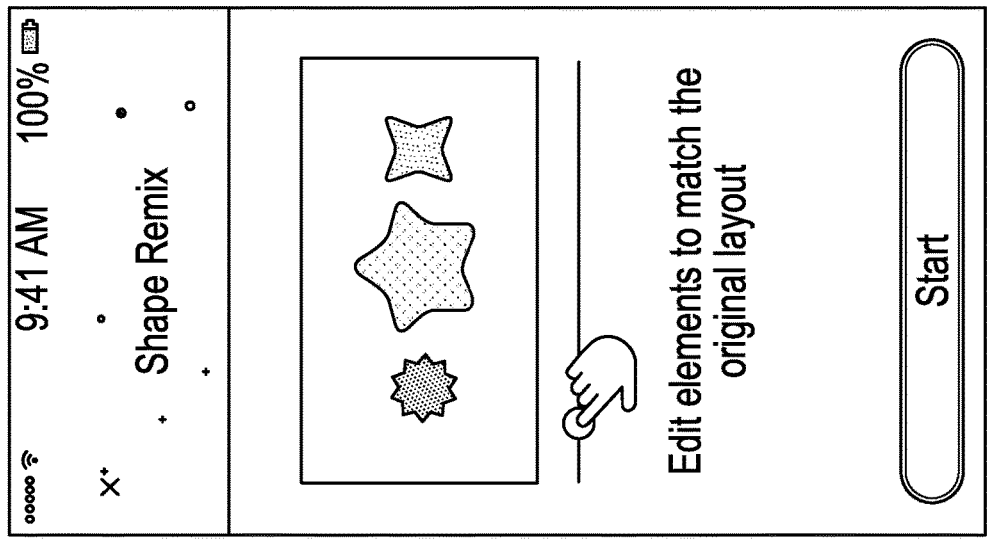
FIG. 26A

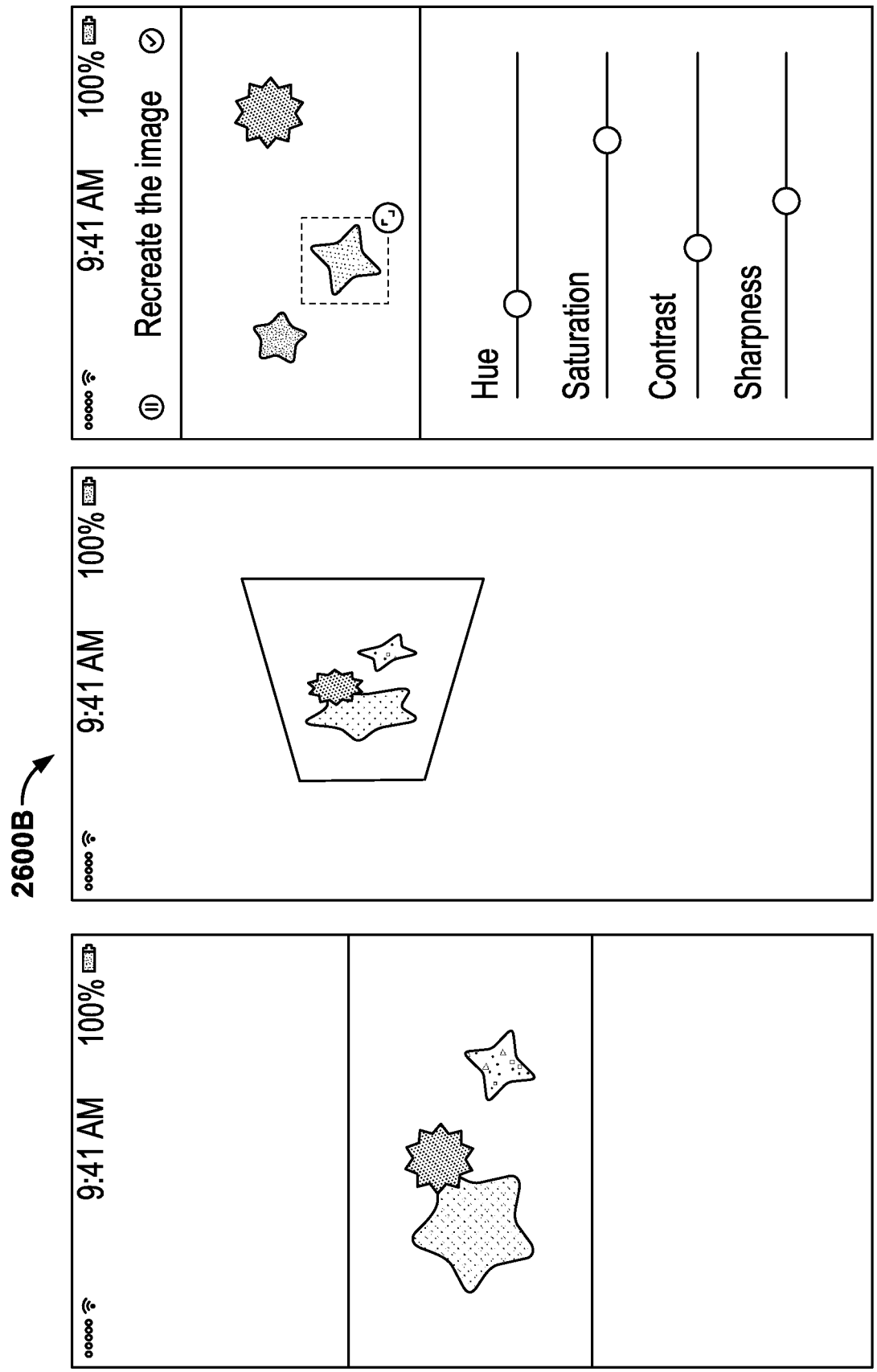

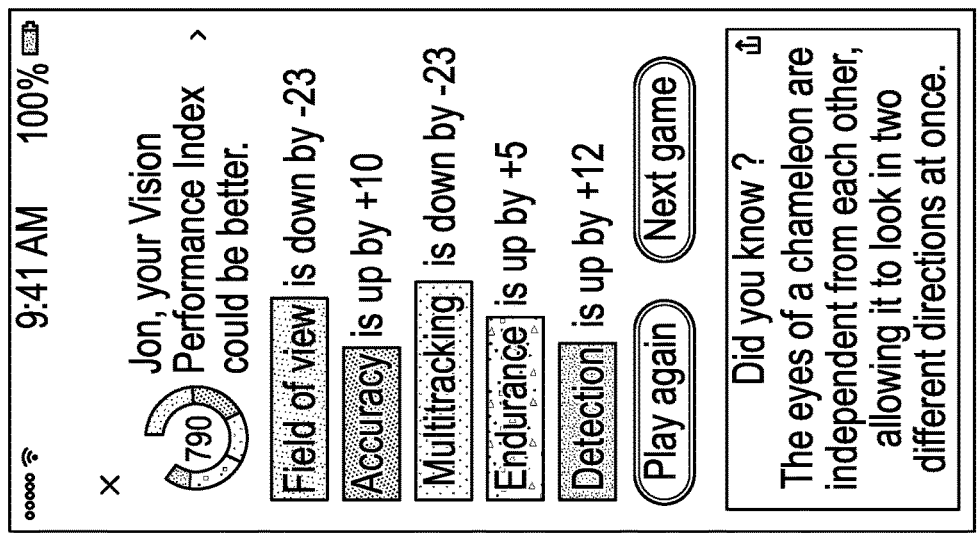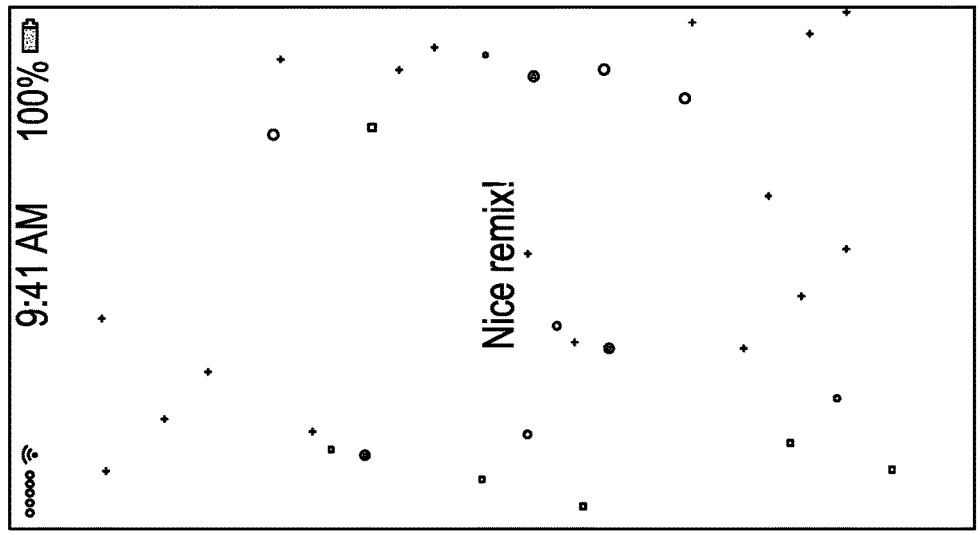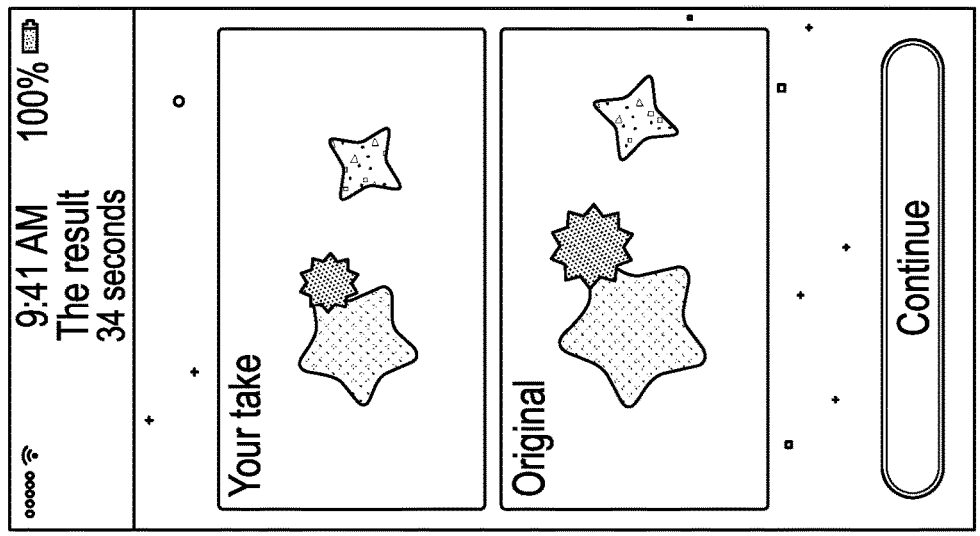
FIG. 26C

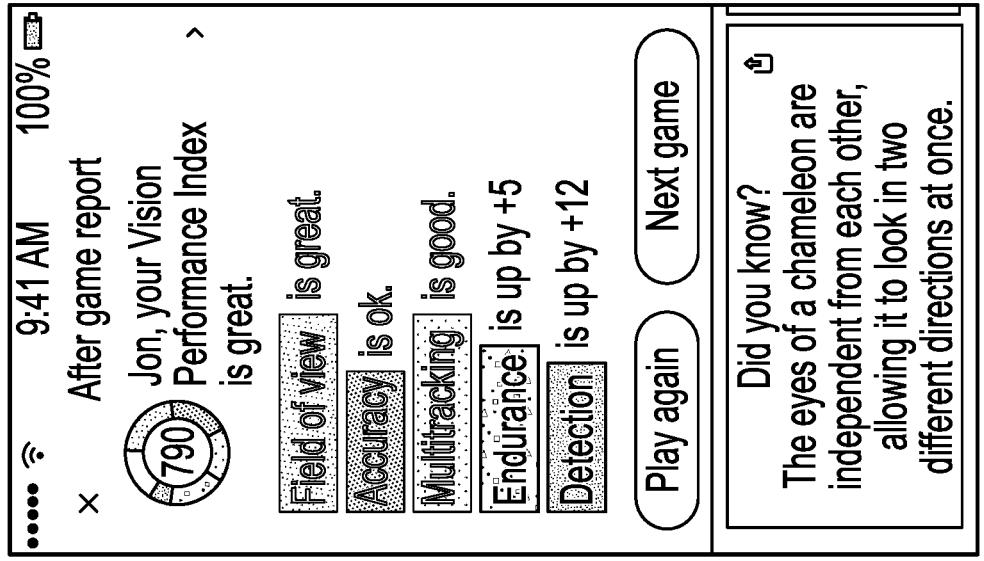
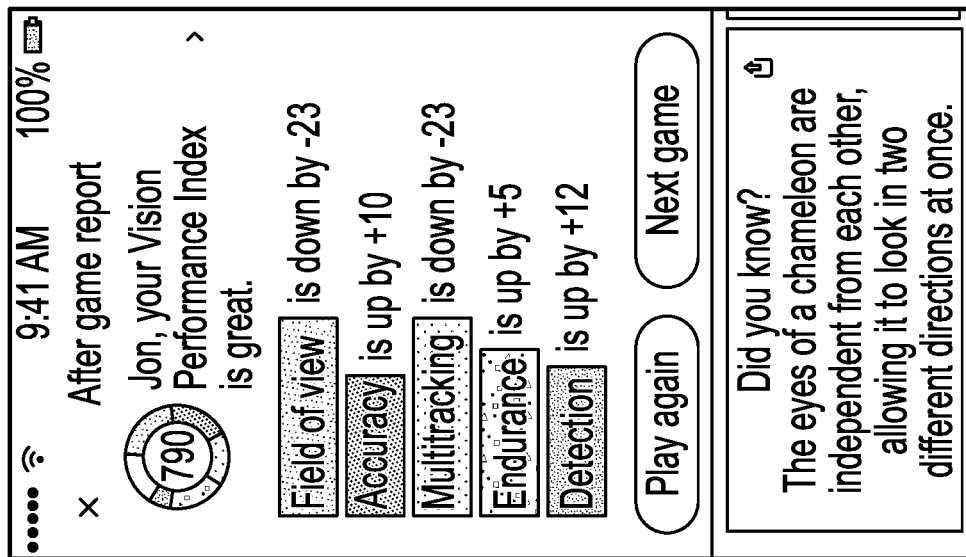
FIG. 27

| 9:41 AM | 100% 🔋 |
|---|---|
| Vision Performance Index | |
| List | Map |

Union Family Vision Center
Cupertino, 1930 9th St Ste 202 ⌄

Occhio Vision Center
Saint Paul, 20730 Valley Green Dr ⌄

In Focus Vision Center
Houston, 2501 Hudron Rd 222 1 Ste 1K21 ⌄

Westlake Vision Center
San Jose, 255 Westlake Park Blvd ⌄

Lifeconnections Vision Center
San Diego, 3571 N 1st St Ste 202 ⌄

Qualcomm Vision Center
Morrisville, 10155 Pacific Heights Bldg AZ ⌄

Apple Austin Vision Center
Morrisville, 10155 Pacific Heights Bldg AZ ⌄

Life Connections Vision Center at Rtp
San Jose, 7100 Kit Creek Rd 49 ⌄

Crossover Health Vision Center at Mountai....
Sacramanto, 1080 La Avenida Bldg A ⌄

Lettie Ball
San Carlos,

FIG. 28 (Cont.)

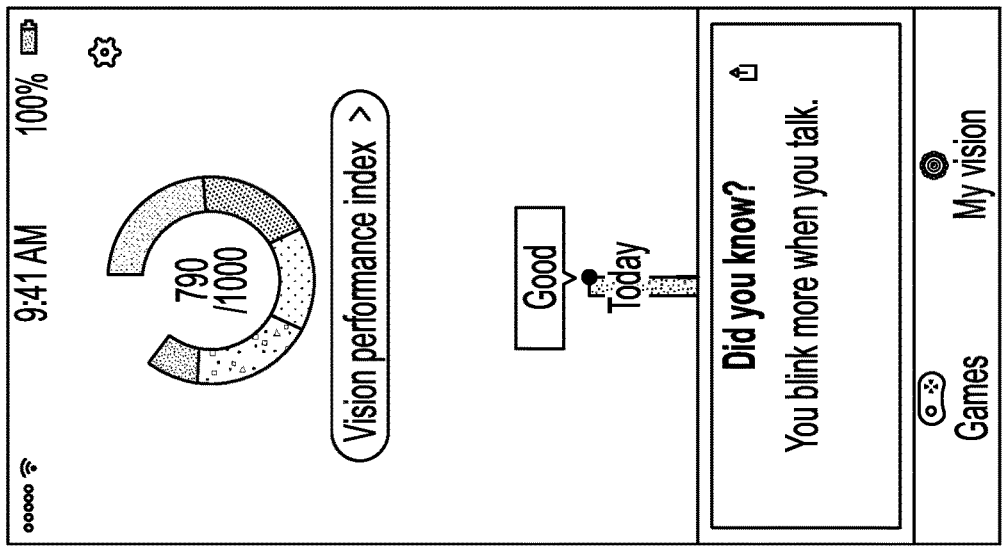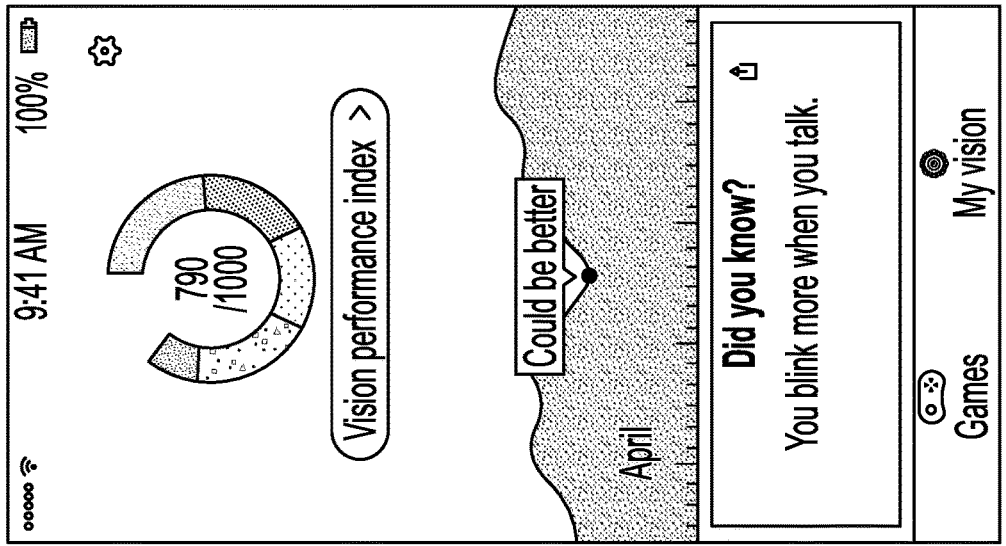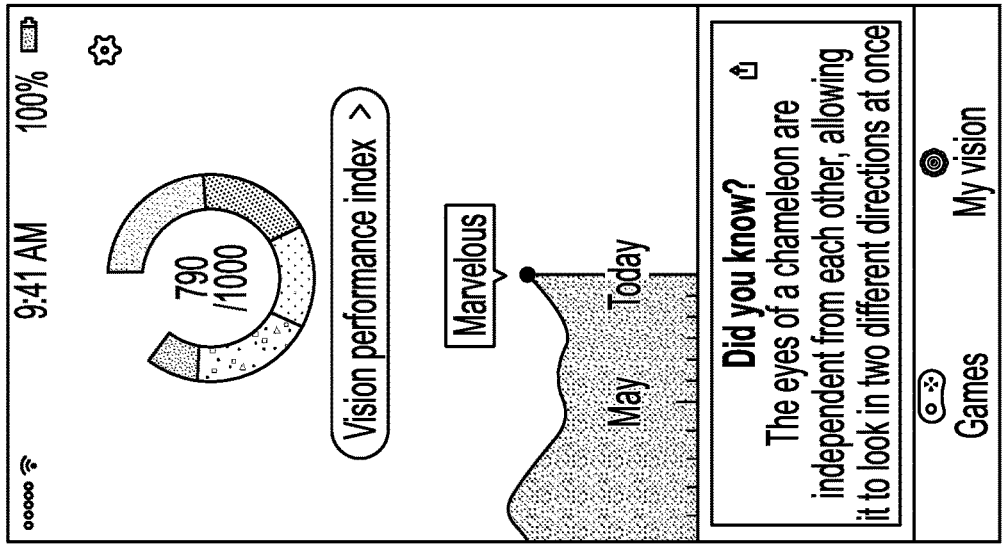
FIG. 29

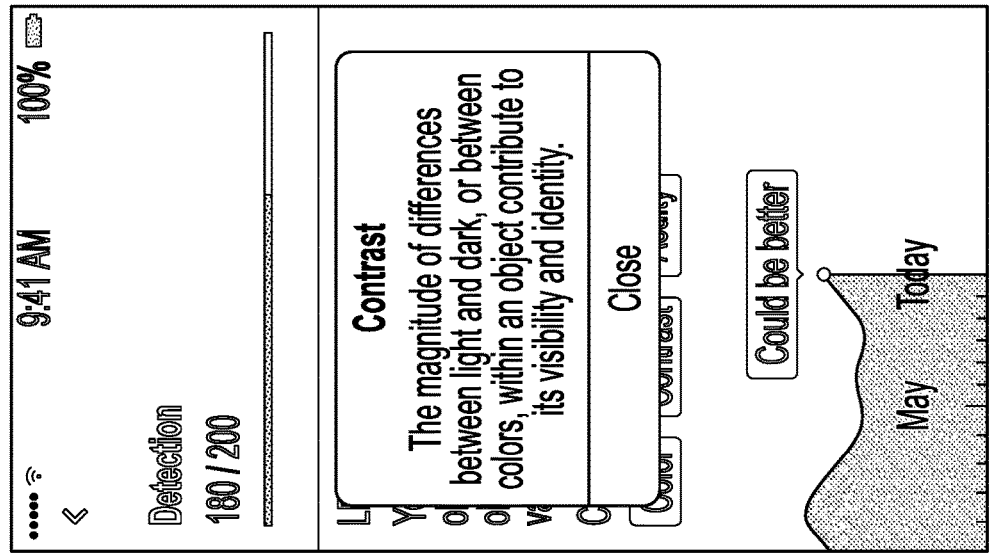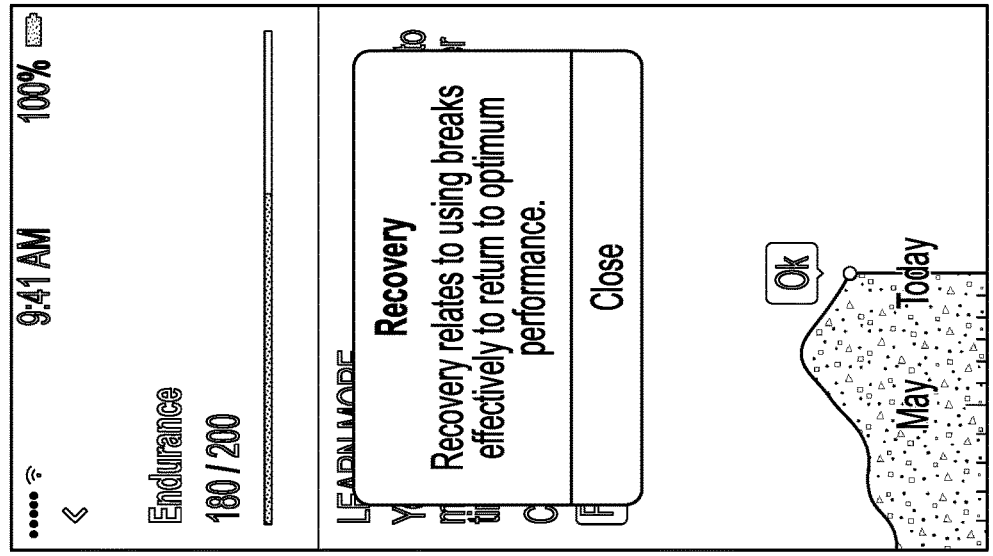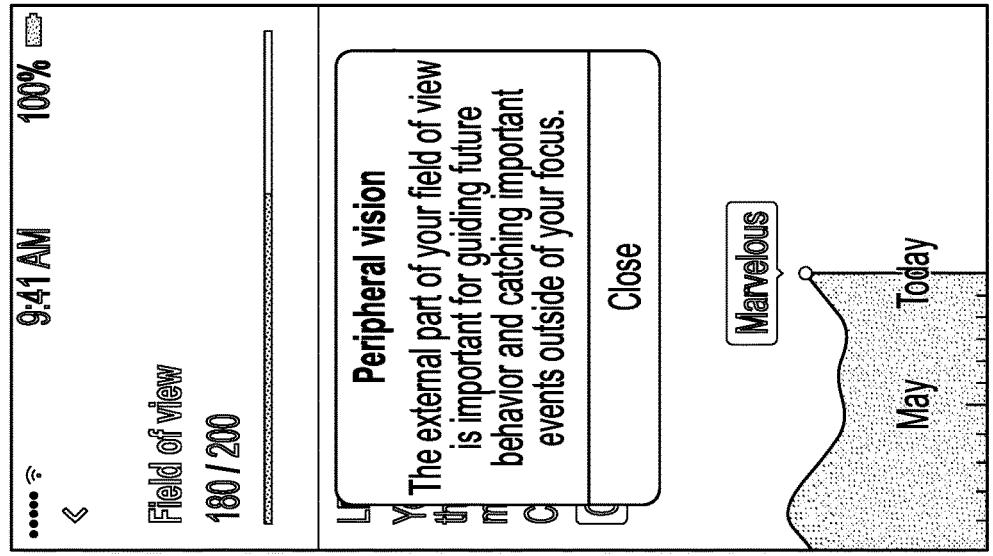
FIG. 30D

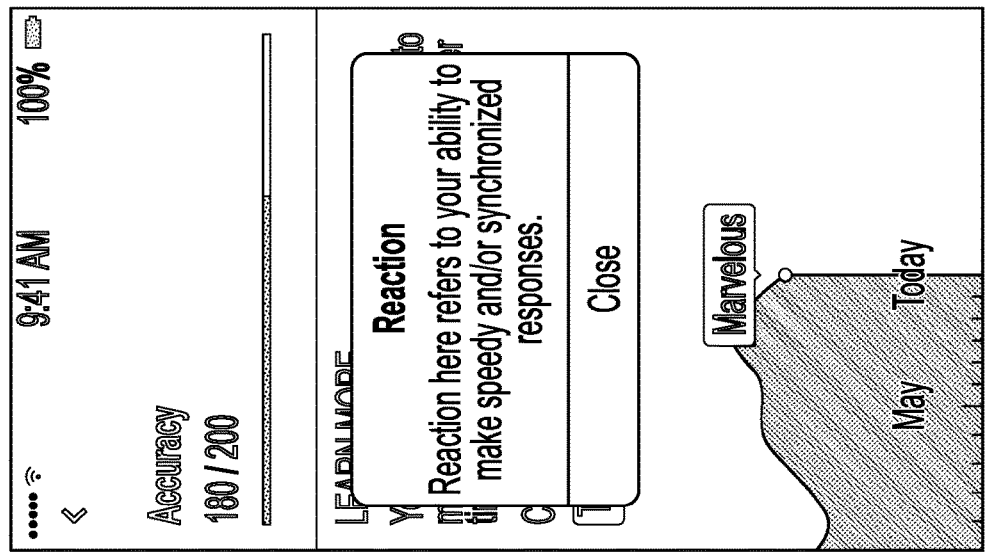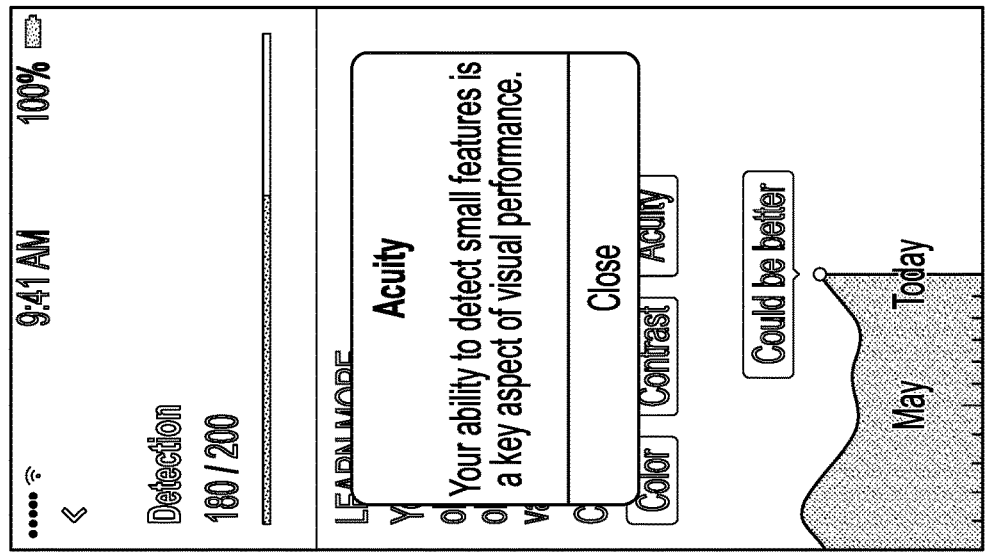
FIG. 30D (Cont.)

FIG. 31

Sight Kit Experiences (Games and Rounds)

| | Pop the Balloons Round 1 | Pop the Balloons Round 2 | Pop the Balloons Round 3 |
|---|---|---|---|
| F.o.V. Central Peripheral | Moderate | F.o.V. Central Peripheral | Minor |
| Accuracy Reaction Targeting | Major | Accuracy Reaction Targeting | Moderate |
| Multi-Track. Focussed Divided | Moderate | Multi-Track. Focussed Divided | Moderate |
| Endurance Fatigue Recovery | (Given Sufficient Play Time) | Endurance Fatigue Recovery | (Given Sufficient Play Time) |
| Detection Color Contrast Acuity | Minor Major Moderate | Detection Color Contrast Acuity | Moderate Minor |

| | Pop the Balloons Round 2 |
|---|---|
| F.o.V. Central Peripheral | Major |
| Accuracy Reaction Targeting | Major |
| Multi-Track. Focussed Divided | |
| Endurance Fatigue Recovery | (Given Sufficient Play Time) |
| Detection Color Contrast Acuity | Moderate |

Sight Kit Experiences (Games and Rounds)

| | Picture Perfect | Shape Remix |
|---|---|---|
| F.o.V. Central Peripheral | | |
| Accuracy Reaction Targeting | Minor | |
| Multi-Track. Focussed Divided | | |
| Endurance Fatigue Recovery | (Given Sufficient Play Time) | |
| Detection Color Contrast Acuity | Major | |

| | Picture Perfect | Shape Remix |
|---|---|---|
| F.o.V. Central Peripheral | | |
| Accuracy Reaction Targeting | | Minor |
| Multi-Track. Focussed Divided | | |
| Endurance Fatigue Recovery | | (Given Sufficient Play Time) |
| Detection Color Contrast Acuity | | Major |

FIG. 32 (Cont.)

METHODS AND SYSTEMS FOR OBTAINING, AGGREGATING, AND ANALYZING VISION DATA TO ASSESS A PERSON'S VISION PERFORMANCE

CROSS-REFERENCE

The present application is a continuation application of U.S. patent application Ser. No. 16/232,712, entitled "Methods and Systems for Obtaining, Aggregating, and Analyzing Vision Data to Assess a Person's Vision Performance" and filed on Dec. 26, 2018, which is a continuation application of U.S. patent application Ser. No. 15/482,560, of the same title, filed on Apr. 7, 2017, and issued as U.S. Pat. No. 10,209,773 on Feb. 19, 2019, which relies on, for priority, the following United States Provisional Patent Applications:

U.S. Provisional Patent Application No. 62/425,736, entitled "Methods and Systems for Gathering Visual Performance Data and Modifying Media Based on the Visual Performance Data" and filed on Nov. 23, 2016;

U.S. Provisional Patent Application No. 62/381,784, of the same title and filed on Aug. 31, 2016;

U.S. Provisional Patent Application No. 62/363,074, entitled "Systems and Methods for Creating Virtual Content Representations Via A Sensory Data Exchange Platform" and filed on Jul. 15, 2016;

U.S. Provisional Patent Application No. 62/359,796, entitled "Virtual Content Representations" and filed on Jul. 8, 2016;

U.S. Provisional Patent Application No. 62/322,741, of the same title and filed on Apr. 14, 2016; and U.S. Provisional Patent Application No. 62/319,825, of the same title and filed on Apr. 8, 2016.

All of the aforementioned applications are incorporated herein by reference in their entirety.

FIELD

The present specification relates generally to vision care and more specifically to methods and systems for obtaining, aggregating, and analysing vision data to assess a person's vision performance.

BACKGROUND

In recent years, the advent of various visual experiences, including Virtual Reality (VR) environments, Augmented Reality (AR), and Mixed Reality (MxR) applications through various mediums, such as tablet computers and mobile phones, have placed a greater strain on the vision of users. Reliable measurements of the strain on vision requires an understanding of numerous psychometrics and how various visual field parameters affect those psychometrics, and how those vision field parameters can be modified in order to avoid certain vision problems.

In turn, this requires an understanding of the interoperability, connectivity, and modularity of multiple sensory interfaces with the brain, with many being closed-looped.

Current measures and rating systems for AR/VR are qualitative in nature. Further, clinical testing interfaces include EEG, MRI, EOG, MEG, fMRI, ultrasound, and microwaves. Traditional industry standards for measuring Field of View include tests such as The Amsler grid, the Humphrey Visual Field Analyzer, Frequency-Doubling technology, the Tangent Screen Exam, the Goldmann Method, and the Octopus perimeter. For Accuracy, compensatory tracking, Jenson Box, and Hick's Law tests/standards are typically used. Industry standard tests for multi-tracking include auditory serial addition, the Posner Cueing Task, and the D2 Test of Attention. For Endurance, typical industry standard tests include Visual Field Perimetry (maintaining fixation) and Optical Coherence Tomography (OCT) Tests. Industry standard Detection tests include Ishihara test (color vision/color plates), Farnsworth-Munsell 100 hue test, Pelli Robson Contrast Sensitivity Chart, Vistech Contrast test, Snellen Charts, ETDRS, and Tumbling Cs.

While these traditional industry standards and clinical standards exist for sight testing, there is still a need for a comprehensive visual performance index or assessment that integrates multiple, disparate measures into a single aggregated measurement. What is also needed is a software interface that provides an aggregate quantification of multiple data points. What is also needed is a method and system for monitoring eye health and identifying changes to vision over time.

SUMMARY

The present specification is directed toward a method of assessing a vision performance of a patient using a computing device programmed to execute a plurality of programmatic instructions, comprising presenting, via the computing device, a first set of visual and/or auditory stimuli; monitoring a first plurality of reactions of the patient using at least one of the computing device and a separate hardware device; presenting, via the computing device, a second set of visual and/or auditory stimuli; monitoring a second plurality of reactions of the patient using at least one of the computing device and a separate hardware device; and based upon said first plurality of reactions and second plurality of reactions, determining quantitative values representative of the patient's field of view, visual acuity, ability of the patient to track multiple stimuli, visual endurance and visual detection.

Optionally, the method further comprises generating a single vision performance value representative of an aggregation of the field of view, the visual acuity, the ability of the patient to track multiple stimuli, the visual endurance and the visual detection. Optionally, the first plurality of reactions comprises at least one of rapid scanning data, saccadic movement data, blink rate data, fixation data, pupillary diameter data, and palpebral fissure distance data. Optionally, the second plurality of reactions comprises at least one of rapid scanning data, saccadic movement data, fixation data, blink rate data, pupillary diameter data, speed of head movement data, direction of head movement data, heart rate data, motor reaction time data, smooth pursuit data, palpebral fissure distance data, degree and rate of brain wave activity data, and degree of convergence data.

Optionally, the hardware device comprises at least one of a camera configured to acquire eye movement data, a sensor configured to detect a rate and/or direction of head movement, a sensor configured to detect a heart rate, and an EEG sensor to detect brain waves. Optionally, the quantitative values representative of the patient's field of view comprises data representative of a quality of the patient's central vision and data representative of a quality of the patient's peripheral vision. Optionally, the quantitative values representative of the patient's visual acuity comprises data representative of a quality of the patient's reaction time to said first set of visual and/or auditory stimuli. Optionally, the quantitative values representative of the patient's visual acuity comprises data representative of a quality of the patient's precise targeting of said first set of visual stimuli and wherein said quality of the patient's precise targeting of said first set of visual stimuli is based on a position of the patient's physical response relative to a position of the first set of visual stimuli.

Optionally, the quantitative values representative of the patient's ability of the patient to track multiple stimuli comprises data representative of a quality of the patient's ability to simultaneous track multiple elements in the second set of visual stimuli. Optionally, the quantitative values representative of the patient's visual endurance comprises data representative of a decrease in the patient's reaction time over a duration of presenting the first set of visual and/or auditory stimuli. Optionally, the quantitative values representative of the patient's visual endurance comprises data representative of an improvement in the patient's reaction time over a duration of presenting the second set of visual and/or auditory stimuli after a rest period. Optionally, the quantitative values representative of the patient's visual detection comprises data representative of to what extent the patient sees the first set of visual stimuli. Optionally, the quantitative values representative of the patient's visual detection comprises data representative of to what extent the patient can discriminate between similarly colored, contrasted, or shaped objects in the first set of visual stimuli.

In another embodiment, the present specification is directed to a method of assessing a vision performance of a patient using a computing device programmed to execute a plurality of programmatic instructions, comprising presenting, via a display on the computing device, a first set of visual stimuli, wherein the first set of visual stimuli comprises a first plurality of visual elements that move from a peripheral vision of the patient to a central vision of the patient; monitoring a first plurality of reactions of the patient using at least one of the computing device and a separate hardware device; presenting, via a display on the computing device, a second set of visual stimuli, wherein the second set of visual stimuli comprises a second plurality of visual elements that appear and disappear upon the patient physically touching said second plurality of visual elements; monitoring a second plurality of reactions of the patient using at least one of the computing device and said separate hardware device; and based upon said first plurality of reactions and second plurality of reactions, determining quantitative values representative of the patient's field of view, visual acuity, ability of the patient to track multiple stimuli, visual endurance and visual detection.

Optionally, at least a portion of the first plurality of visual elements have sizes that decrease over time. Optionally, at least a portion of the first plurality of visual elements have a speed of movement that increases over time. Optionally, over time, more of the first plurality of visual elements simultaneously appear on said computing device. Optionally, a third plurality of visual elements appear concurrent with said second plurality of visual elements, wherein the third plurality of visual elements appear different than the second plurality of visual elements, and wherein, if the patient physically touches any of said third plurality of visual elements, the quantitative value representative of the patient's visual acuity is decreased.

Optionally, the method further comprises presenting, via a display on the computing device, a third set of visual stimuli, wherein the third set of visual stimuli comprises a fourth plurality of visual elements; monitoring a third plurality of reactions of the patient using at least one of the computing device and said separate hardware device; and based upon said first plurality of reactions, second plurality of reactions, and third plurality of reactions determining quantitative values representative of the patient's field of view, visual acuity, ability of the patient to track multiple stimuli, visual endurance and visual detection. Optionally, the patient is instructed to identify one of the fourth plurality of visual elements having a specific combination of color, contrast, and/or shape.

It should be appreciated that while the method is described above as having a particular order of presenting visual stimuli, the present invention is directed toward any order of presenting the visual elements and corresponding monitoring for specific patient vision quantitative values. For example, optionally, at least a portion of the second plurality of visual elements have sizes that decrease over time. Optionally, at least a portion of the second plurality of visual elements have a speed of movement that increases over time. Optionally, over time, more of the second plurality of visual elements simultaneously appear on said computing device. Optionally, a third plurality of visual elements appear concurrent with said first plurality of visual elements, wherein the third plurality of visual elements appear different than the first plurality of visual elements, and wherein, if the patient physically touches any of said third plurality of visual elements, instead of the first plurality of visual elements, the quantitative value representative of the patient's visual acuity is decreased.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 14 provides a table containing a list of exemplary metrics for afferent and efferent sources, in accordance with some embodiments of the present specification;

Figure 19:
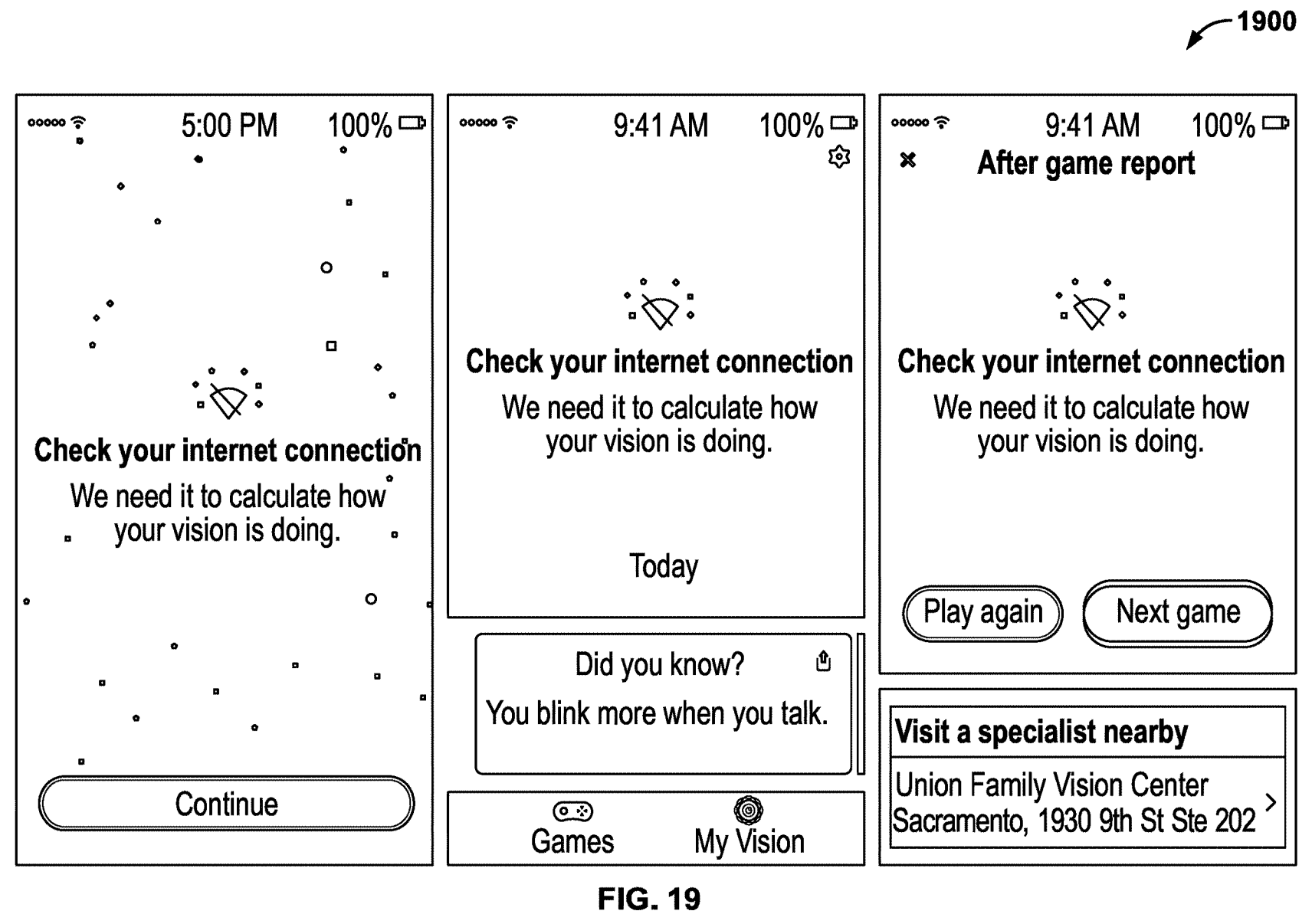

FIG. 19 illustrates screenshots of empty and error screens that may appear through the sight kit application, in accordance with an embodiment of the present specification;

FIG. 20C illustrates a series of screenshots of the login (registration) process including an exemplary registration by a user named 'Jon Snow' that may appear through the sight kit application, in accordance with an embodiment of the present specification;

FIG. 21A illustrates a series of screenshots of screens that prompt a user with demographic questions that may appear through the sight kit application, in accordance with an embodiment of the present specification;

FIG. 21C illustrates still further series of screenshots of screens that prompt a user with demographic questions that may appear through the sight kit application, in accordance with an embodiment of the present specification;

FIG. 24A illustrates a screenshot of Pop the Balloons Round 1 instructions, which may be presented through the sight kit application in accordance with an embodiment of the present specification;

FIG. 24B illustrates a screenshot of Pop the Balloons Round 1 game, which may be presented through the sight kit application in accordance with an embodiment of the present specification;

FIG. 24C illustrates a screenshot of Pop the Balloons Round 2 instructions, which may be presented through the sight kit application in accordance with an embodiment of the present specification;

FIG. 24D illustrates a screenshot of Pop the Balloons Round 2 game, which may be presented through the sight kit application in accordance with an embodiment of the present specification;

FIG. 25A illustrates a series of screenshots of Picture Perfect Round 1 game, which may be presented through the sight kit application in accordance with an embodiment of the present specification;

FIG. 25D illustrates a series of screenshots of Picture Perfect Round 2 game, which may be presented through the sight kit application in accordance with an embodiment of the present specification;

FIG. 25E illustrates a series of screenshots of Picture Perfect Round 2 game, which may be presented through the sight kit application in accordance with an embodiment of the present specification;

FIG. 26A illustrates a similar set of screenshots for 'Shape Remix' game, its instructions, and after game report, which may be presented through the sight kit application in accordance with an embodiment of the present specification;

FIG. 26C illustrates a similar set of screenshots for 'Shape Remix' game, its instructions, and after game report, which may be presented through the sight kit application in accordance with an embodiment of the present specification.

FIG. 27 illustrates screenshots of VPI game reports after playing different games that may appear through the sight kit application, in accordance with an embodiment of the present specification;

FIG. 29 illustrates some screenshots of the screens that present a user's profile that may appear through the sight kit application, in accordance with an embodiment of the present specification;

FIG. 30D illustrates some screenshots of the VPI breakdown that provide further details of parameters within each FAMED parameter, through the sight kit application in accordance with an embodiment of the present specification;

FIG. 31 illustrates screenshots for 'Settings' and related options within 'Settings', which may be presented through the sight kit application in accordance with an embodiment of the present specification; and FIG. 32 is a table showing exemplary experiences of different VPI parameters from the different games and rounds.

DETAILED DESCRIPTION

Figure 1:
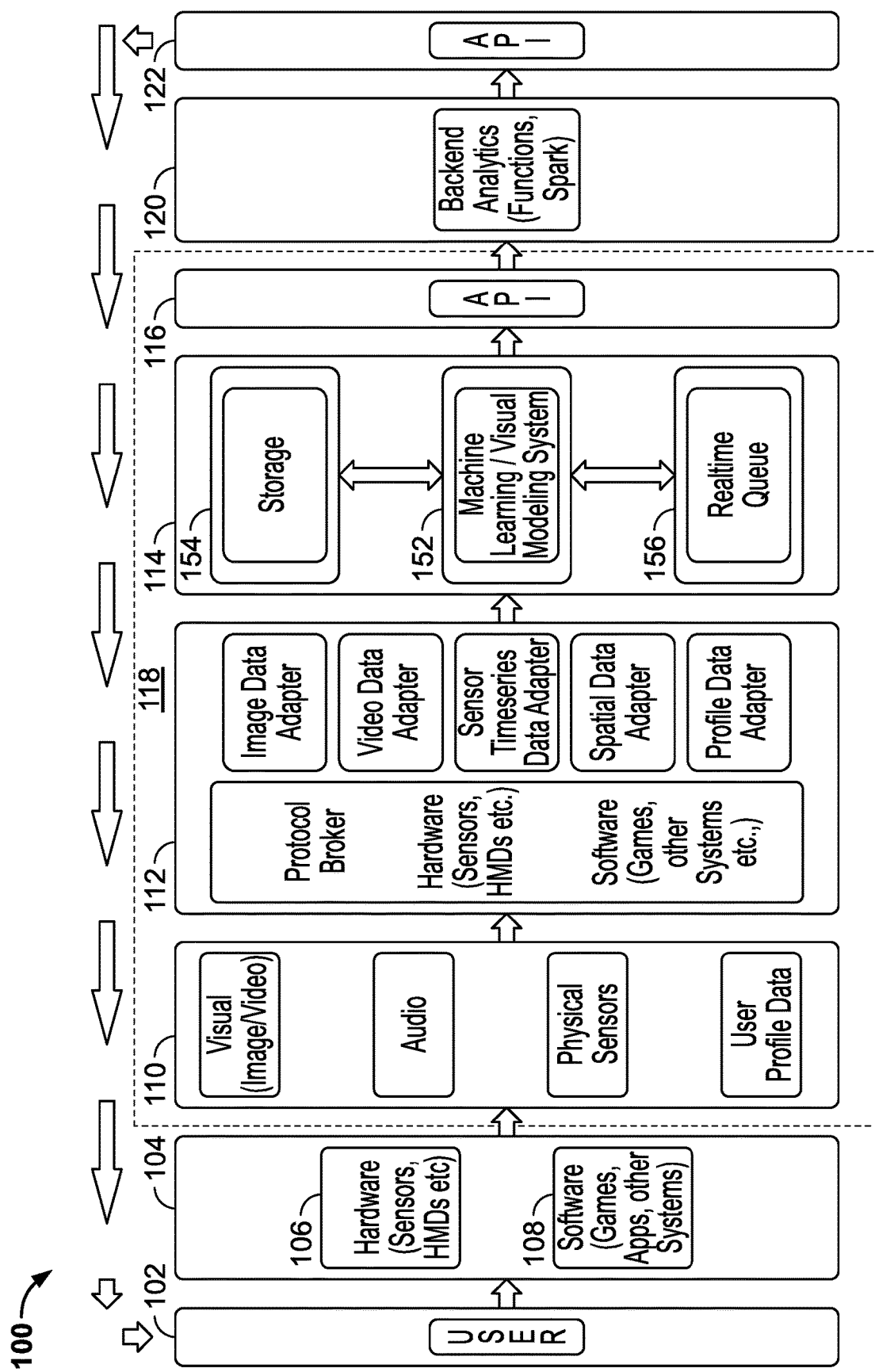
FIG. 1 shows a block diagram illustrating user interaction with an exemplary Sensory Data Exchange Platform (SDEP), in accordance with an embodiment of the present specification.

In one embodiment, the present specification describes methods, systems and software that are provided to vision service providers in order to gather more detailed data about the function and anatomy of human eyes in response to various stimuli.

In one embodiment, a Sensory Data Exchange Platform (SDEP) is provided, wherein the SDEP may enable developers of games, particularly mobile applications or other media and/or software, to optimize the media for a user and/or a group of users. In embodiments, the SDEP, or at least a portion thereof, is embodied in a software application that is presented to an end-user through one or more electronic media devices including computers, portable computing devices, mobile devices, or any other device that is capable of presenting virtual reality (VR), augmented reality (AR), and/or mixed reality MxR media.

In an embodiment, a user interacts with a software program embodying at least a portion of the SDEP in a manner that enables the software to collect user data and provided it to the SDEP. In an embodiment, the user may interact directly or indirectly with a SDEP to facilitate data collection. In an embodiment, the SDEP is a dynamic, two-way data exchange platform with a plurality of sensory and biometric data inputs, a plurality of programmatic instructions for analyzing the sensory and biometric data, and a plurality of outputs for the delivery of an integrated visual assessment.

In some embodiments, the SDEP outputs as a general collective output a "visual data profile" or a "vision performance index" (VPI). In some embodiments, the SDEP outputs as a general collective output a vision performance persona. The visual data profile or vision performance index may be used to optimize media presentations of advertising, gaming, or content in a VR/AR/MxR system. In embodiments, the platform of the present specification is capable of taking in a number of other data sets that may enhance the understanding of a person's lifestyle and habits. In addition, machine learning, computer vision, and deep learning techniques are employed to help monitor and predict health outcomes through the analysis of an individual's data. In embodiments, the vision performance index is employed as a tool for measuring vision function. In embodiments, the vision performance index may be generated based upon any plurality or combination of data described throughout this specification and is not limited to the examples presented herein.

In an embodiment, the SDEP is used via an operating system executed on hardware (such as mobile, computer or Head Mounted Display (HMD)). In another embodiment, the SDEP is used by one or more content developers. In one embodiment, both hardware and content developers use the SDEP. The SDEP may enable collection of data related to how the user is interfacing with the content presented, what aspects of the content they are most engaged with and how engaged they are. Data collected through the SDEP may be processed to create a profile for the user and or groups of users with similar demographics. The content may be represented, for a particular profile, in a way that conforms to the hardware capabilities of the VR/AR/MxR system in a manner to optimize experience of that user and other users with a similar profile.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all whole or fractional numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

It should be noted herein that any feature or component described in association with a specific embodiment may be used and implemented with any other embodiment unless clearly indicated otherwise.

It should be further appreciated that all the afferent data presented herein and efferent data collected are performed using a hardware device, such as a mobile phone, laptop, tablet computer, or specialty hardware device, executing a plurality of programmatic instructions expressly designed to present, track, and monitor afferent data and to monitor, measure, and track efferent data, as further discussed below.

General Definitions

The term "Virtual Reality" or "VR" is used throughout this specification, and, in embodiments, refers to immersive computer-simulated reality, or the computer-generated simulation of a three-dimensional image or environment that can be interacted with in a seemingly real or physical way by a person using special electronic equipment, such as a helmet with a screen inside and/or gloves fitted with sensors.

In embodiments, Augmented Reality (AR), also used along with VR throughout this specification, is a technology that superimposes a computer-generated image on a user's view of the real world, thus providing a composite view. In embodiments, a common helmet-like device is the HMD, which is a display device, worn on the head or as part of the helmet, that has a small display optic in front of one (monocular HMD) or each eye (binocular HMD). In embodiments, the SDEP is a cloud-based service that any party can access in order to improve or otherwise modify a visually presented product or service.

Further, in embodiments, Mixed Reality (MxR), is also used with VR and AR throughout this specification. MxR, also referred to as hybrid reality, is the merging of VR and/or AR environments with the real environment to produce new levels of visual-experiences where physical and digital objects co-exist and interact in real time.

In embodiments, VR, AR, and MxR devices could include one or more of electronic media devices, computing devices, portable computing devices including mobile phones, laptops, personal digital assistants (PDAs), or any other electronic device that can support VR, AR, or MxR media. It should be noted herein that while the present specification is disclosed in the context of Virtual Reality, any and all of the systems and methods described below may also be employed in an Augmented Reality environment as well as Mixed Reality environments. So, where a Virtual Reality (VR) system is described, it should be understood by those of ordinary skill in the art that the same concepts may apply to an Augmented Reality (AR) and a Mixed Reality (MxR) system.

Eye-Tracking Definitions

In terms of performance, several eye tracking measures are put into the context of Vision Performance Index (VPI) components, which are defined and described in detail in subsequent section of the specification. Blink rate and vergence measures can feed into measures of fatigue and recovery. Gaze and, more specifically, fixation positions can be used to estimate reaction and targeting measures. Continuous error rates during pursuit eye movements can also become targeting measures.

In embodiments, the vision performance index is employed as a tool for measuring vision function. In embodiments, the vision performance index may be generated based upon any plurality or combination of data described throughout this specification and is not limited to the examples presented herein.

Various examples of physical measures for eye tracking may be available with desired standard units, expected ranges for measured values and/or, where applicable, thresholds for various states or categories based on those measures. Some references are provided through sections that discuss various components and subcomponents of eye tracking.

The following terms are associated with eye-tracking measures as made from a combination of video recording and image processing techniques; expert human scoring; and/or from electrooculography (EOG) recording. Video eye tracking (VET) techniques may use explicit algorithmic analysis and/or machine learning to estimate proportional eyelid opening/closure, pupil size, pupil position (relative to the face) and gaze direction independently for each eye. EOG recording may be used to estimate eyelid and eye motion and, with limited precision, eye gaze direction. Both recording modalities may sample at rates of tens to thousands of times per second and allow for analysis of position, velocity, direction, and acceleration for the various measures. Comparison between the two eyes allows for measures of vergence which in turn allows for a three-dimensional (3D) gaze direction to be estimated.

Palpebral Fissure refers to the opening of the eyelids. While typically about 30 millimeters (mm) wide by 10 mm tall, most measurements can be relative to baseline distances measured on video. Of particular interest is the height (interpalpebral fissure height) as it relates to the following terms:

Percent Open ($p_{eye\ open}$) refers to how open the left ($p_{left\ eye\ open}$), right ($p_{right\ eye\ open}$), or both ($p_{both\ eyes\ open}$) eyes are, relative to the maximum open distance and typically measured over a predefined period of time.

Proportion Open ($P_{eyes\ open}$) refers to the proportion of time the eyes are open over a span of time (for example, during a session (P_(eyes open|session))). The threshold for 'open' may be variable (for example, $P_{eyes\ open}$ (where $P_{both\ eyes\ open} \geq 25\%$)).

Blink can be defined as a complete closure of both eyes ($p_{both\ eyes\ open} = 0\%$) for between roughly 10 to 400 milliseconds (ms), with a specific measured blink closure time being based on differences among users and the eye tracking method.

Blink Rate (Frequency) ($f_{blink}$) refers to the average number of blinks per second ($s^{-1}$ or Hz) measured for all blinks and/or blinks over a period of time (e.g. f_(blink|target present)). The blink rate may be referred to as a rate of change of the blink rate or a ratio of partial blinks to full blinks.

Blink Count Number (N_blink) refers to the number of blinks measured for all blinks and/or blinks over a period of time (e.g. N_(blink|target present)).

Pupil Size (S_pupil) refers to the size of the pupil, typically the diameter in millimeters (mm).

Pupil Position ([x, y]_pupil) refers to the position of the left ([x, y]_(left pupil)) or right ([x, y]_(right pupil)) pupil within the fixed reference frame of the face, typically as a function of time. The pupil position definition includes, and is dependent upon, an initial pupil position and a final pupil position.

Gaze Direction ([θ, φ]_gaze) refers to the direction in 3D polar coordinates of left ([θ, φ]_(left gaze)) or right ([θ, φ]_(right gaze)) eye gaze relative to the face, typically as a function of time. This is a measure of where the eyes are facing without regard to what the eyes see. It may be further classified as relevant or irrelevant depending on a task or a target.

Gaze Position ([x, y, z]_gaze or [r, θ, φ]_gaze) refers to the position (or destination) of gaze in the environment in Cartesian or spherical 3D coordinates, typically as a function of time. The reference frame may be with respect to the user, device or some other point in space, but most commonly the origin of a coordinate space will be the user's eyes (one or the other or a point halfway between). The gaze position definition includes, and is dependent upon, an initial gaze position and a final gaze position.

Vergence is derived from estimated gaze direction and may be quantified as the difference in angle of the two eyes (positive differences being divergence and negative being convergence). When derived from gaze position, vergence contributes to and may be quantified as the distance of the gaze position from the eyes/face. Convergence and divergence may each be defined by their duration and rate of change.

Fixation Position ($[x, y, z]_{fixation}$ or $[r, θ, φ]_{fixation}$) is the position of a fixation in Cartesian or spherical 3D space measured as the estimated position of the user's gaze at a point in time. The fixation position definition includes, and is dependent upon, an initial fixation position and a final fixation position.

Fixation Duration ($D_{fixation}$) is the duration of a fixation (i.e. the time span between when the gaze of the eye arrives at a fixed position and when it leaves), typically measured in milliseconds or seconds (s). The average duration is denoted with a bar $\underline{D}_{fixation}$ and may represent all fixations, fixations over a period of time (e.g. _D_(fixation|target present)) and/or fixations within a particular region (e.g. _D_(fixation|display center)). The fixation duration definition includes, and is dependent upon, a rate of change in fixations.

Fixation Rate (Frequency) (f_fixation) refers to the average number of fixations per second ($s^{-1}$ or Hz) measured for all fixations, fixations over a period of time (e.g. f_(fixation|target present)) and/or fixations within a particular region (e.g. f_(fixation|display center)).

Fixations Count (Number) ($N_{fixation}$) refers to the number of fixations measured for all fixations, fixations over a period of time (e.g. N_(fixation|target present)) and/or fixations within a particular region (e.g. N_(fixation|display center)).

Saccade Position ($[x_1, y_1, z_1|x_2, y_2, z_2]_{saccade}$ or $[r_1, θ_1, φ_1|r_2, θ_2, φ_2]_{saccade}$) refers to the starting (1) and ending (2) positions of a saccadic eye movement in Cartesian or spherical 3D space. The reference frame will generally be the same, within a given scenario, as that used for gaze position. The saccade position definition includes, and is dependent upon, a rate of change, an initial saccade position, and a final saccade position.

Saccade Angle ($Θ_{saccade}$) refers to an angle describing the 2-dimensional (ignoring depth) direction of a saccade with respect to some reference in degrees (°) or radians (rad). Unless otherwise specified the reference is vertically up and the angle increases clockwise. The reference may be specified (e.g. $Θ_{saccade-target}$) to denote the deviation of the saccade direction from some desired direction (i.e. towards a target). The average saccade direction is denoted with a bar $\underline{Θ}_{saccade}$ and may represent all or a subset of saccades (e.g. _Θ_(saccade|target present)); because the direction is angular (i.e. circular) the average direction may be random unless a relevant reference is specified (e.g. _Θ_(saccade-target|target present)). The saccade angle may be used to determine how relevant a target is to a user, also referred to as a context of relevancy towards a target.

Saccade Magnitude ($M_{saccade}$) refers to the magnitude of a saccade relating to the distance traveled; this may be given as a visual angle in degrees (°) or radians (rad), a physical distance with regard to the estimated gaze position (e.g. in centimeters (cm) or inches (in)) or a distance in display space with regard to the estimated gaze position on a display (e.g. in pixels (px)). In reference to a particular point (P) in space, the component of the saccade magnitude parallel to a direct line to that point may be given as:

$$M_{saccade-P} = M_{saccade} \cdot \cos(Θ_{saccade-P})$$

where $M_{saccade}$ is the magnitude of the saccade and $Θ_{saccade-P}$ is the angle between the saccade direction and a vector towards point P. The average saccade magnitude is denoted with a bar $\underline{M}_{saccade}$, and this notation may be applied to all saccades and/or a subset in time or space and with regard to saccade magnitudes or the components of saccade magnitude relative to a designated point.

Pro-Saccade refers to movement towards some point in space, often a target, area of interest or some attention-capturing event. By the above terminology a pro-saccade would have a relatively small saccadic angle and positive magnitude component relative to a designated position.

Anti-Saccade refers to movement away from some point in space, often due to aversion or based on a task (instruction to look away). By the above terminology an anti-saccade would have a relatively large saccadic angle (around ±180° or ±π rad) and a negative magnitude component relative to a designated position.

Inhibition of Return (IOR) is related to anti-saccades and describes a tendency during search or free viewing to avoid recently fixated regions which are less informative. IOR reflects a general strategy for efficient sampling of a scene. It may be furthered defined by, or a function of, anti-saccades.

Saccade Velocity ($v_{saccade}$) or the velocity of a saccade is taken as the change in magnitude over time (and not generally from magnitude components towards a reference point). Based on the degree of magnitude and direction of the saccade velocity, it may be indicative of a degree of relevancy of the target to the user. The average saccade velocity is denoted with a bar $\bar{v}_{saccade}$ and may be applied to all saccades or a subset in time and/or space.

Saccade Rate (Frequency) ($f_{saccade}$) denotes the average number of saccades per second ($s^{-1}$ or Hz) measured for all saccades, saccades over a period of time (e.g. f_(saccade|target present)), saccades within a particular region (e.g. f_(saccade|display center)) and/or saccades defined by their direction (e.g. f_(saccade|towards target)).

Saccade Count (Number) ($N_{saccade}$) is the number of saccades measured for all saccades, saccades over a period of time (e.g. N_(saccade|target present)), saccades within a particular region (e.g. N_(saccade|display center)) and/or saccades defined by their direction (e.g. N_(saccade|towards target)).

Pursuit Eye Movements (PEM) is used to refer to both smooth pursuit eye movements where gaze tracks a moving object through space and vestibulo-ocular movements that compensate for head or body movement. It may be further defined by data indicative of an initiation, a duration, and/or a direction of smooth PEM. Also included are compensatory tracking of stationary objects from a moving frame of reference. PEM generally do not consist of fixations and saccades but rather continuous, relatively slow motion interrupted by occasional error-correcting saccades. The smooth and saccadic portions of a PEM trace may be subtracted and analyzed separately.

Body Tracking Definitions

Body tracking entails measuring and estimating the position of the body and limbs as a function of time and/or discrete events in time associated with a class of movement (e.g. a nod of the head). Information sources include video tracking with and without worn markers to aid in image processing and analysis, position trackers, accelerometers and various hand-held or worn devices, platforms, chairs, or beds.

Screen Distance ($d_{screen}$) refers to the distance between the user's eyes (face) and a given display device. As a static quantity, it is important for determining the direction towards various elements on the screen (visual angle), but as a variable with time, screen distance can measure user movements towards and away from the screen. Screen distance is dependent upon a rate of change, an initial position, and a final position between the user's eyes (face) and a given display device. Combined with face detection algorithms, this measure may be made from device cameras and separate cameras with known position relative to displays.

Head Direction (Facing) ($[\theta, \phi]_{facing}$) refers to the direction in 3D polar coordinates of head facing direction relative to either the body or to a display or other object in the environment. Tracked over time this can be used to derive events like nodding (both with engagement and fatigue), shaking, bobbing, or any other form of orientation. Head direction is dependent upon a rate of change, an initial position, and a final position of head facing direction relative to either the body or to a display or other object in the environment.

Head Fixation, while similar to fixations and the various measures associated with eye movements, may be measured and behavior-inferred. Generally head fixations will be much longer than eye fixations. Head movements do not necessarily indicate a change in eye gaze direction when combined with vestibulo-ocular compensation. Head fixation is dependent upon a rate of change, an initial position, and a final position of head fixations.

Head Saccade, while similar to saccades and their various measures associated with eye movements, may be measured as rapid, discrete head movements. These will likely accompany saccadic eye movements when shifting gaze across large visual angles. Orienting head saccades may also be part of auditory processing and occur in response to novel or unexpected sounds in the environment.

Head Pursuit, while similar to pursuit eye movements, tend to be slower and sustained motion often in tracking a moving object and/or compensating for a moving frame of reference.

Limb Tracking refers to the various measures that may be made of limb position over time using video with image processing or worn/held devices that are themselves tracked by video, accelerometers or triangulation. This includes pointing devices like a computer mouse and hand-held motion controllers. Relative limb position may be used to derive secondary measures like pointing direction. Limb tracking is dependent upon a rate of change, an initial position, and a final position of the limbs.

Weight Distribution refers to the distribution of weight over a spatial arrangement of sensors while users stand, sit or lie down can be used to measure body movement, position and posture. Weight distribution is dependent upon a rate of change, an initial position, and a final position of weight.

Facial expressions including micro-expressions, positions of eyebrows, the edges, corners, and boundaries of a person's mouth, and the positions of a user's cheekbones, may also be recorded.

Electrophysiological and Autonomic Definitions

Electrophysiological measures are based on recording of electric potentials (voltage) or electric potential differences typically by conductive electrodes placed on the skin. Depending on the part of the body where electrodes are placed various physiological and/or behavioral measures may be made based on a set of metrics and analyses. Typically voltages (very small—microvolts μV) are recorded as a function of time with a sample rate in the thousands of times per second (kHz). While electrophysiological recording can measure autonomic function, other methods can also be used involving various sensors. Pressure transducers, optical sensors (e.g. pulse oxygenation), accelerometers, etc. can provide continuous or event-related data.

Frequency Domain (Fourier) Analysis allows for the conversion of voltage potentials as a function of time (time domain) into waveform energy as a function of frequency. This can be done over a moving window of time to create a spectrogram. The total energy of a particular frequency or range of frequencies as a function of time can be used to measure responses and changes in states.

Electroencephalography (EEG) refers to electrophysiological recording of brain function. Time averaged and frequency domain analyses (detailed below) provide measures of states. Combined with precise timing information about stimuli, event-related potentials (EEG-ERP) can be analyzed as waveforms characteristic of a particular aspect of information processing.

Frequency Bands are typically associated with brain activity (EEG) and in the context of frequency domain analysis different ranges of frequencies are commonly used to look for activity characteristic of specific neural processes or common states. Frequency ranges are specified in cycles per second ($s^{-1}$ or Hz):

Delta—Frequencies less than 4 Hz. Typically associated with slow-wave sleep.
Theta—Frequencies between 4 and 7 Hz. Typically associated with drowsiness.
Alpha—Frequencies between 8 and 15 Hz.
Beta—Frequencies between 16 and 31 Hz.
Gamma—Frequencies greater than 32 Hz.

Electrocardiography (ECG) refers to electrophysiological recording of heart function. The primary measure of interest in this context is heart rate.

Electromyography (EMG) refers to electrophysiological recording of muscle tension and movement. Measures of subtle muscle activation, not necessarily leading to overt motion, may be made. Electrodes on the face can be used to detect facial expressions and reactions.

Electrooculography (EOG) refers to electrophysiological recording across the eye. This can provide sensitive measures of eye and eyelid movement, however with limited use in deriving pupil position and gaze direction.

Electroretinography (ERG) refers to electrophysiological recording of retinal activity.

Galvanic Skin Response (GSR) (Electrodermal response) is a measure of skin conductivity. This is an indirect measure of the sympathetic nervous system as it relates to the release of sweat.

Body Temperature measures may be taken in a discrete or continuous manner. Relatively rapid shifts in body temperature may be measures of response to stimuli. Shifts may be measured by tracking a rate of change of temperature, an initial temperature, and a final temperature.

Respiration Rate refers to the rate of breathing and may be measured from a number of sources including optical/video, pneumography and auditory and will typically be measured in breaths per minute ($min^{-1}$ Brief pauses in respiration (i.e. held breath) may be measured in terms of time of onset and duration.

Oxygen Saturation ($S_{O_2}$) is a measure of blood oxygenation and may be used as an indication of autonomic function and physiological state.

Heart Rate is measured in beats per minute ($min^{-1}$nd may be measured from a number of sources and used as an indication of autonomic function and physiological state.

Blood Pressure is typically measured with two values: the maximum (systolic) and minimum (diastolic) pressure in millimeters of mercury (mm Hg). Blood pressure may be used as an indication of autonomic function and physiological state.

Efferent Audio Recording Definitions

Audio recording from nearby microphones can measure behavioral and even autonomic responses from users. Vocal responses can provide measures of response time, response meaning or content (i.e. what was said) as well as duration of response (e.g. "yeah" vs. "yeeeeeeeaaaah"). Other utterances like yawns, grunts or snoring might be measured. Other audible behaviors like tapping, rocking, scratching or generally fidgety behavior may be measured. In certain contexts, autonomic behaviors like respiration may be recorded.

Vocalizations, such as spoken words, phrases and longer constructions may be recorded and converted to text strings algorithmically to derive specific responses. Time of onset and duration of each component (response, word, syllable) may be measured. Other non-lingual responses (yelling, grunting, humming, etc.) may also be characterized. Vocalizations may reflect a range of vocal parameters including pitch, loudness, and semantics.

Inferred Efferent Responses refer to certain efferent responses of interest that may be recorded by audio and indicate either discrete responses to stimuli or signal general states or moods. Behaviors of interest include tapping, scratching, repeated mechanical interaction (e.g. pen clicking) bouncing or shaking of limbs, rocking and other repetitive or otherwise notable behaviors.

Respiration, such as measures of respiration rate, intensity (volume) and potentially modality (mouth vs. nose) may also be made.

Afferent Classification/Definitions

The states discussed below are generally measured in the context of or response to various stimuli and combinations of stimuli and environmental states. A stimulus can be defined by the afferent input modality (visual, auditory, haptic, etc.) and described by its features. Features may be set by applications (e.g. setting the position, size, transparency of a sprite displayed on the screen) or inferred by image/audio processing analysis (e.g. Fourier transforms, saliency mapping, object classification, etc.).

Regions of interest as discussed below may be known ahead of time and set by an application, may be defined by the position and extent of various visual stimuli and/or may be later derived after data collection by image processing analysis identifying contiguous, relevant and/or salient areas. In addition to stimulus features, efferent measures may be used to identify regions of interest (e.g. an area where a user tends to fixate is defined by gaze position data). Likewise both afferent and efferent measures may be used to segment time into periods for summary analysis (e.g. total number of fixations while breath is held).

Sensory Data Exchange Platform Overview

Reference is made to FIG. 1, which shows a block diagram 100 illustrating user interaction with an exemplary SDEP, in accordance with an embodiment of the present specification. In an embodiment, a user 102 interfaces with a media system, such as an app on a tablet computer or a VR/AR/MxR system 104. The media system 104 may include devices such as HMDs, sensors, and/or any other forms of hardware elements 106 that present visual, auditory, and other sensory media to the user and enables collection of user response data during user interaction with the presented media. The media may be communicated by a server, through a network, or any other type of content platform that is capable of providing content to hardware devices, such as HMDs. Sensors may be physiological sensors, biometric sensors, or other basic and advanced sensors to monitor user 102. Additionally, sensors may include environmental sensors that record audio, visual, haptic, or any other types of environmental conditions that may directly or indirectly impact the vision performance of user 102. The media system 104 may also include software elements 108 that may be executed in association with hardware elements 106. Exemplary software elements 108 include gaming programs, software applications (apps), or any other types of software elements that may contribute to presentation of media to user 102. Software elements 108 may also enable the system to collect user response data. Collected data may be tagged with information about the user, the software application, the game (if any), the media presented to the user, the session during which the user interacted with the system, or any other data. A combination of hardware elements 106 and software elements 108 may be used to present media to user 102.

In an embodiment, stimulus and response data collected from user's 102 interaction with the software system 104 may constitute data sources 110. Data sources 110 may be created within a SDEP 118 based on an interaction between software elements 108 and SDEP 118. Software elements 108 may also interact with SDEP 118 through proprietary function calls included in a Software Development Kit (SDK) for developers (i.e. the developers may send/receive data to/from SDEP 118 using predefined functions). SDEP 118 may include storage and processing components and could be a computing system. The functionality of SDEP 118 may largely reside on one or more servers and the data stored and retrieved from cloud services. Sources of data may be in the form of visual data, audio data, data collected by sensors deployed with the software system 104, user profile data, or any other data that may be related to user 102. Visual data may largely include stimulus data and may be sourced from cameras (such as cell phone cameras or other vision equipment/devices), or from other indirect sources such as games and applications (apps). Sensors may provide spatial and time series data. User data may pertain to login information, or other user-specific information derived from their profiles, from social media apps, or other personalized sources. In embodiments, data sources are broadly classified as afferent data sources and efferent data sources, which are described in more detail in subsequent sections of the specification. In an embodiment, user profile data may be collected from another database, or may be provided through a different source. In an exemplary embodiment user profile data may be provided by service providers including one or more vision care insurance provider. In other embodiments, the user profile data may be collected from other sources including user's device, opt-in options in apps/games, or any other source.

Data sources 110 may be provided to a data ingestion system 112. Data ingestion system 112 may extract and/or transform data in preparation to process it further in a data processing system 114. Data adapters, which are a set of objects used to communicate between a data source and a dataset, may constitute data ingestion system 112. For example, an image data adapter module may extract metadata from images, and may also process image data. In another example, a video data adapter module may also extract metadata from video data sources, and may also include a video transcoder to store large volumes of video into distributed file system. In another example, a time series data adapter module parses sensor data to time series. In another embodiment, a spatial data adapter module may utilize data from relatively small areas such as skin, and spatially transform the data for area measurements. In another example, a user profile data adapter module may sort general user data, such as through a login, a social media connect API, unique identifiers on phone, and the like.

SDEP 118 may further comprise a data processing system 114 that receives conditioned data from data ingestion system 112. A machine learning module 152 within data processing system 114 may communicate with a storage 154 and a real time queue 156 to output data to a data serving system 116, which may include an Application Program Interface (API). In embodiments, the machine learning system may implement one or more known and custom models to process data output from data ingestion system 112.

In embodiments, SDEP 118 may further include a module 120 for backend analytics that feeds another API 122. API 122 may, in turn, interface with user 102, providing modified media to user 102.

Figure 2A:
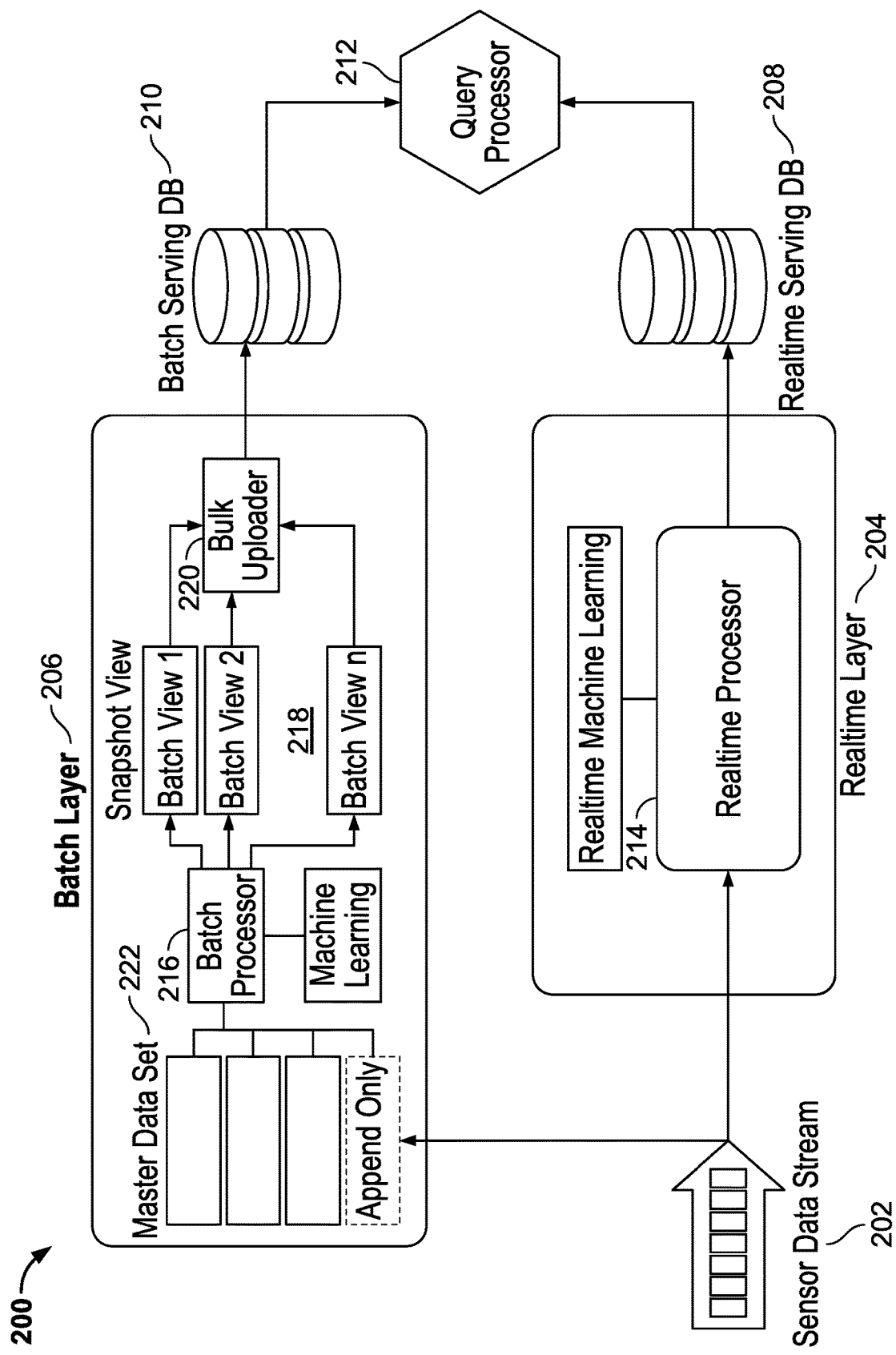
FIG. 2A is a block diagram illustrating processing of a sensor data stream before it reaches a query processor, in accordance with an embodiment of the present specification.

FIG. 2A is a block diagram illustrating processing of a sensor data stream before it reaches a query processor, in accordance with an embodiment of the present specification. In an embodiment, FIG. 2A illustrates a lambda architecture 200 for a sensor data stream received by a SDEP. Data processing architecture 200 may be designed to handle large quantities of data by parallel processing of data stream and batch. In an embodiment, a sensor data stream 202 comprising sensor data collected from users in real time is provided to a real time layer 204. Real time layer 204 may receive and process online data through a real time processor 214. Data collected in batches may be provided to a batch layer 206. Batch layer 206 comprises a master data set 222 to receive and utilize for processing time stamped events that are appended to existing events. Batch layer 206 may precompute results using a distributed processing system involving a batch processor 216 that can handle very large quantities of data. Batch layer 206 may be aimed at providing accurate data by being able to process all available sensor data, to generate batch views 218. A bulk uploader 220 may upload output to be stored in a database 210, with updates completely replacing existing precomputed batch views. Processed data from both layers may be uploaded to respective databases 208 and 210 for real time serving and batch serving. Data from databases 208 and 210 may subsequently be accessed through a query processor 212, which may be a part of a serving layer. Query processor 212 may respond to ad-hoc queries by returning precomputed views or building views from the processed data. In embodiments, real-time layer 204, batch layer 206, and serving layer may be utilized independently.

Data Acquisition

Events may be coded within the stream of data, coming potentially from the app, the user and environmental sensors, and may bear timestamps indicating when things happen. Anything with an unambiguous time of occurrence may qualify as an "event". Most events of interest may be discrete in time, with time stamps indicating either the start or the end of some state. As an exception, electrophysiological data may be recorded continuously and generally analyzed by averaging segments of data synchronized in time with other events or by some other analysis.

In an embodiment, data collected from interactions with user 102 is broadly classified as afferent data and efferent data, corresponding to afferent events and efferent events. In the peripheral nervous system, an afferent nerve fiber is the nerve fiber (axon) of an afferent neuron (sensory neuron). It is a long process (projection) extending far from the nerve cell body that carries nerve impulses from sensory receptors or sense organs toward the central nervous system. The opposite direction of neural activity is efferent conduction. Conversely, an efferent nerve fiber is the nerve fiber (axon) of an efferent neuron (motor neuron). It is a long process (projection) extending far from the nerve cell body that carries nerve impulses away from the central nervous system toward the peripheral effector organs (mainly muscles and glands).

A "stimulus" may be classified as one or more events, typically afferent, forming a discrete occurrence in the physical world to which a user may respond. A stimulus event may or may not elicit a response from the user and in fact may not even be consciously perceived or sensed at all; thus, if an event occurred, it is made available for analysis. Stimulus event classes may include "Application Specific Events" and "General and/or Derived Stimulus Events".

Application Specific Events may include the many stimulus event classes that may be specific to the sights, sounds, and other sensory effects of a particular application. All of the art assets are potential visual stimuli, and all of the sound assets are potential auditory stimuli. There may be other forms of input including, but not limited to gustatory, olfactory, tactile, along with physiologic inputs—heart rate, pulse ox, basal body temperature, along with positional data accelerometer, visual-motor—limb movement, gyroscope—head movements/body movement—direction, force, and timing. The sudden or gradual appearance or disappearance, motion onset or offset, playing or pausing or other change in state of these elements will determine their specific timestamp. Defining these stimulus event classes may require an app developer to collaborate with the SDE, and may include specific development of image/audio processing and analysis code.

General and/or Derived Stimulus Events are those stimulus events that may be generic across all applications. These may include those afferent events derived from video (e.g. head mounted camera) or audio data recorded of the scene and not coming directly from the app (which itself will provide a more accurate record of those events). Device specific, but not app specific, events may also be classified. Likewise calibration and other activities performed for all apps may be considered general (though perhaps still able to be categorized by the app about to be used).

Some stimulus events may not be apparent until after a large volume of data is collected and analyzed. Trends may be detected and investigated where new stimulus event classes are created to explain patterns of responding among users. Additionally, descriptive and predictive analysis may be performed in order to facilitate real-time exchange of stimuli/content depending on the trends/patterns so as to personalize user-experience.

A "response" may be classified as one or more events, typically efferent, forming a discrete action or pattern of actions by the user, potentially in response to a perceived stimulus (real or imagined). Responses may further include any changes in physiological state as measured by electrophysiological and/or autonomic monitoring sensors. Responses may not necessarily be conscious or voluntary, though they will be identified as conscious/unconscious and voluntary/involuntary whenever possible. Response events classes may include discrete responses, time-locked mean responses, time derivative responses, and/or derived response events.

"Discrete Responses" represent the most common response events associated with volitional user behavior and are discrete in time with a clear beginning and end (usually lasting on the order of seconds or milliseconds). These include, among others, mouse or touch screen inputs, vocalizations, saccadic and pursuit eye movements, eye blinks (voluntary or not), head or other body part movement and electrophysiologically detected muscle movements.

Due to the noisy nature of some data recording, notably electrophysiological recording, it is difficult to examine responses to individual stimulus events. A Time-Locked Mean Response refers to the pattern of responding to a particular stimulus event, which may be extracted from numerous stimulus response events by averaging. Data for a length of time (usually on the order of seconds) immediately following each presentation of a particular stimulus is put aside and then averaged over many "trials" so that the noise in the data (presumably random in nature) cancels itself out leaving a mean response whose characteristics may be measured.

Time Derivative Responses reflect that some responses, particularly autonomic responses, change slowly over time; Sometimes too slowly to associate with discrete stimulus events. However the average value, velocity of change or acceleration of velocity (and other derived measures) within certain periods of time may be correlated with other measured states (afferent or efferent).

As with stimulus events, some response events may not be apparent before data collection but instead reveal themselves over time. Whether through human or machine guided analysis, some characteristic responses may emerge in the data, hence may be termed Inferred Response Events.

Whenever possible, responses will be paired with the stimuli which (may have) elicited them. Some applications may make explicit in the data stream how stimuli and responses are paired (as would be the case in psychophysical experimentation). For the general case, stimulus event classes will be given a set period of time, immediately following presentation, during which a response is reasonably likely to be made. Any responses that occur in this time frame may be paired with the stimulus. If no responses occur then it will be assumed the user did not respond to that stimulus event. Likewise response events will be given a set period of time, immediately preceding the action, during which a stimulus is likely to have caused it. Windows of time both after stimuli and before responses may be examined in order to aid in the discovery of new stimulus and response event classes not previously envisioned.

Stimulus and Response Event Classes may be defined and differentiated by their features (parameters, values, categories, etc.). Some features of an event class may be used to establish groups or categories within the data. Some features may (also) be used to calculate various metrics. Features may be numeric in nature, holding a specific value unique to the event class or the individual instance of an event. Features may be categorical, holding a named identity either for grouping or potentially being converted later into a numerical representation, depending on the analysis.

The features of stimulus events may primarily constitute a physical description of the stimulus. Some of these features may define the event class of the stimulus, and others may describe a specific occurrence of a stimulus (e.g. the timestamp). The named identity of a stimulus (e.g. sprite file name) and state information (e.g. orientation or pose) are stimulus features. The pixel composition of an image or waveform of a sound can be used to generate myriad different descriptive features of a stimulus. Some stimulus features may require discovery through data analysis, just as some stimulus event classes themselves may emerge from analysis.

Response features may generally include the type or category of response made, positional information (e.g. where the mouse click occurred or where a saccade originated/landed, a touch, a gaze, a fixation, turn of head, turn of body, direction and velocity of head, or body/limb movement) and timing information. Some derived features may come from examining the stimulus to which a response is made; for example: whether the response was "correct" or "incorrect".

Figure 2B:
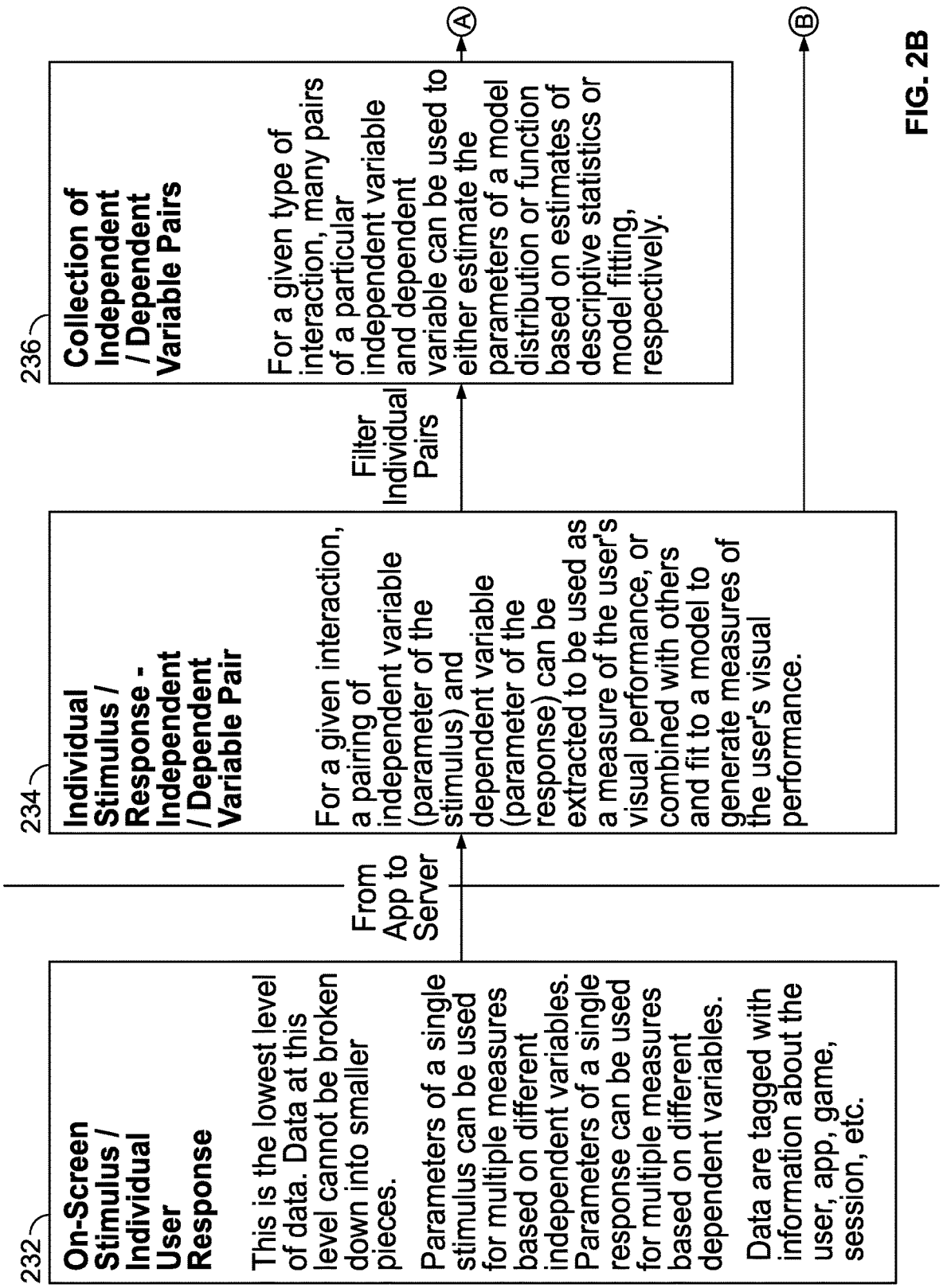
FIG. 2B is an exemplary outline of a data analysis chain.
Figure 2B:
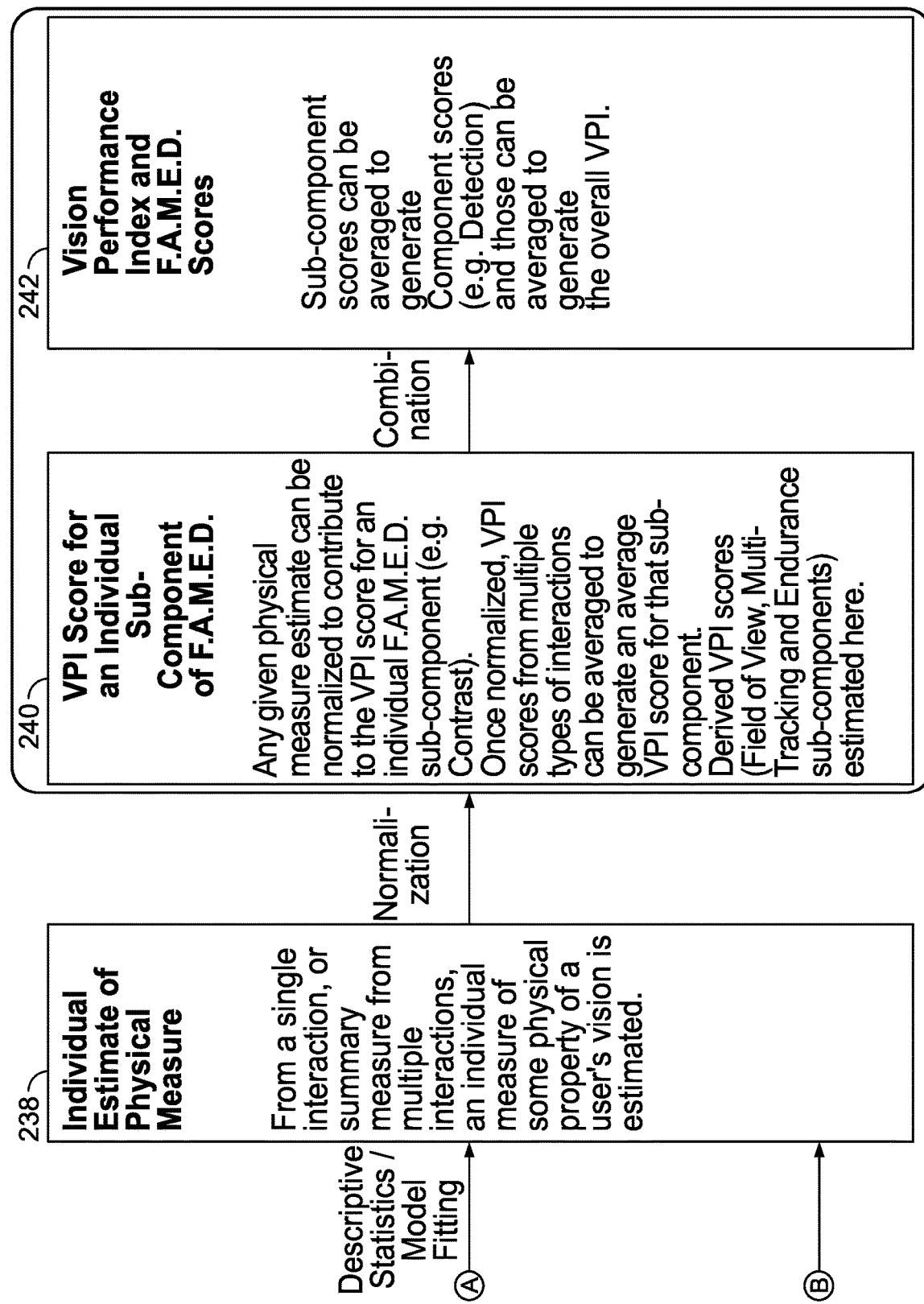

FIG. 2B illustrates an exemplary outline of a data analysis chain. The data analysis begins at the lowest level at 232 wherein data at this level may not be simplified or broken down further. At 232, parameters of a single stimulus can be used for multiple measures based on different independent variables, which correspond to direct features of a stimulus. Parameters of a single response can be used for multiple measures based on different dependent variables.

Figure 3:
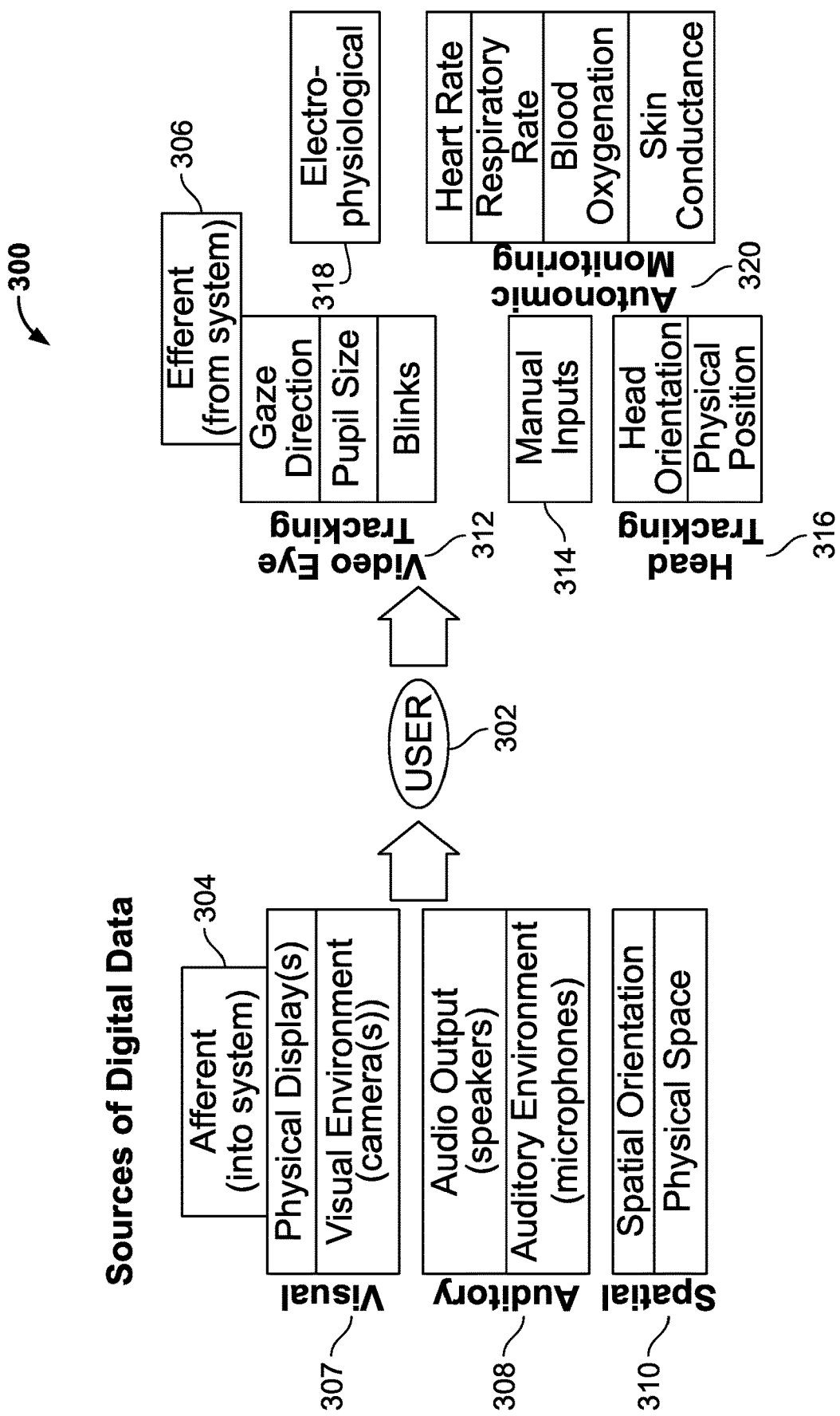
FIG. 3 illustrates an overview of sources of digital data, in accordance with an embodiment of the present specification.

FIG. 3 illustrates an overview 300 of sources of digital data. In embodiments, afferent data 304 may be collected from sources that provide visual information 307, auditory information 308, spatial information 310, or other environmentally measured states including and not limited to temperature, pressure, and humidity. Sources of afferent data 304 may include events that are meant to be perceived by a user 302. User 302 may be a user interfacing with a media system in accordance with various embodiments of the present specification.

Afferent and efferent data may be collected for a plurality of people and related to demographic data that correspond to the profiles for each of the plurality of people, wherein the demographic data includes at least the sex and the age of each of the plurality of people. Once such a database is created, medical treatments can be created that are targeted to a group of people having at least one particular demographic attribute by causing the media content of that service to have a greater impact on the retino-geniculo-cortical pathway of the targeted group.

Afferent Data

Afferent (stimulus) events may be anything happening on a display provided to user 302 in the display, events coming from speakers or head/earphones, or haptic inputs generated by an app. Data may also be collected by environment sensors including and not limited to head-mounted cameras and microphones, intended to keep a record of things that may have been seen, heard, or felt by user 302 but not generated by the app itself. Afferent data 304 may be a form of stimulus, which may be broken down into raw components (features or feature sets) that are used to build analytic metrics.

In embodiments, an afferent (stimulus) event is paired with an efferent (response) event. In the pairing, each of the component stimulus features may be paired with each of the component response features for analysis. In some cases pairs of stimulus features or pairs of response features may also be examined for correlations or dependencies. Stimulus/response feature pairs are at the root of most of the conceivable metrics to be generated. All analyses may be broken down by these feature pairs before being grouped and filtered according to various other of the event features available. In embodiments, for all data sources including afferent 304 and efferent 306 data sources, timing information is required to correlate inputs to, and outputs from, user's 302 sensory system. The correlations may be utilized to identify characteristic metrics or psychophysical metrics for the user. For example, if the media system 104 records that an object was drawn on a screen at time tS (stimulus), and also that a user pressed a particular key at a time tR (response), the time it took the user to respond to the stimulus may be derived by subtracting tR-tS. In alternate embodiments, the user may press a key, or make a gesture, or interact with the media environment through a touch or a gesture. This example correlates afferent data 302 and efferent data 304.

An example that correlates two types of afferent data 304 may be if a gaze tracker indicates that the gaze position of a user changed smoothly over a given period of time indicating that the user was tracking a moving object. However, if a head tracker also indicates smooth motion in the opposite direction, at the same time, it might also indicate that the user was tracking a stationary object while moving their head.

Another example that correlates two types of afferent data 304 may be if visual object appears at time t1, and a sound file is played at time t2. If the difference between t1 and t2 is small (or none), they may be perceived as coming from the same source. If the difference is large, they may be attributed to different sources.

The data taken from accumulated response events may be used to describe patterns of behavior. Patterns of responding, independent of what stimuli may have elicited them, can be used to categorize various behavioral or physiological states of the user. Grouping responses by the stimuli that elicited them can provide measures of perceptual function. In some cases analyses of stimulus events may provide useful information about the apps themselves, or in what experiences users choose to engage. The analysis may include following parameters: unique events, descriptive statistics, and/or psychometric functions.

Unique Events represent instances where raw data may be of interest. Some uncommon stimulus or response events may not provide opportunities for averaging, but instead are of interest because of their rarity. Some events may trigger the end of a session or time period of interest (e.g. the user fails a task and must start over) or signal the beginning of some phase of interaction.

Descriptive Statistics provide summarized metrics. Thus, if multiple occurrences of an event or stimulus/response event or feature pairing may be grouped by some commonality, measures of central tendency (e.g. mean) and variability (e.g. standard deviation) may be estimated. These summarized metrics may enable a more nuanced and succinct description of behavior over raw data. Some minimal level of data accumulation may be required to be reasonably accurate.

Psychometric Functions may form the basis of measures of perceptual sensitivity and ability. Whenever a particular class of stimulus event is shown repeatedly with at least one feature varying among presentations there is an opportunity to map users' pattern of responses against that stimulus feature (assuming responding varies as well). For example, if the size (stimulus feature) of a particular object in a game varies, and sometimes the user finds it and sometimes they don't (response feature), then the probability of the user finding that object may be plotted as a function of its size. This may be done for multiple stimulus/response feature pairs for a single stimulus/response event pairing or for many different stimulus/response event pairs that happen to have the same feature pairing (e.g. size/detection). When a response feature (detection, discrimination, preference, etc.) plotted against a stimulus feature (size, contrast, duration, velocity, etc.) is available with mean responses for multiple stimulus levels, a function to that data (e.g. detection vs. size) may be fitted. The variables that describe that function can themselves be descriptive of behavior. Thresholds may be defined where on one side is failure and the other side success, or on one side choice A and the other side choice B, among others.

Visual Information

Referring back to FIG. 3, in an embodiment, for an application, visual information data 307 from physical display(s) and the visual environment is in the form of still image files and/or video files captured by one or more cameras. In an embodiment, data is in the form of instructions for drawing a particular stimulus or scene (far less data volume required, some additional time in rendering required).

Figure 4:
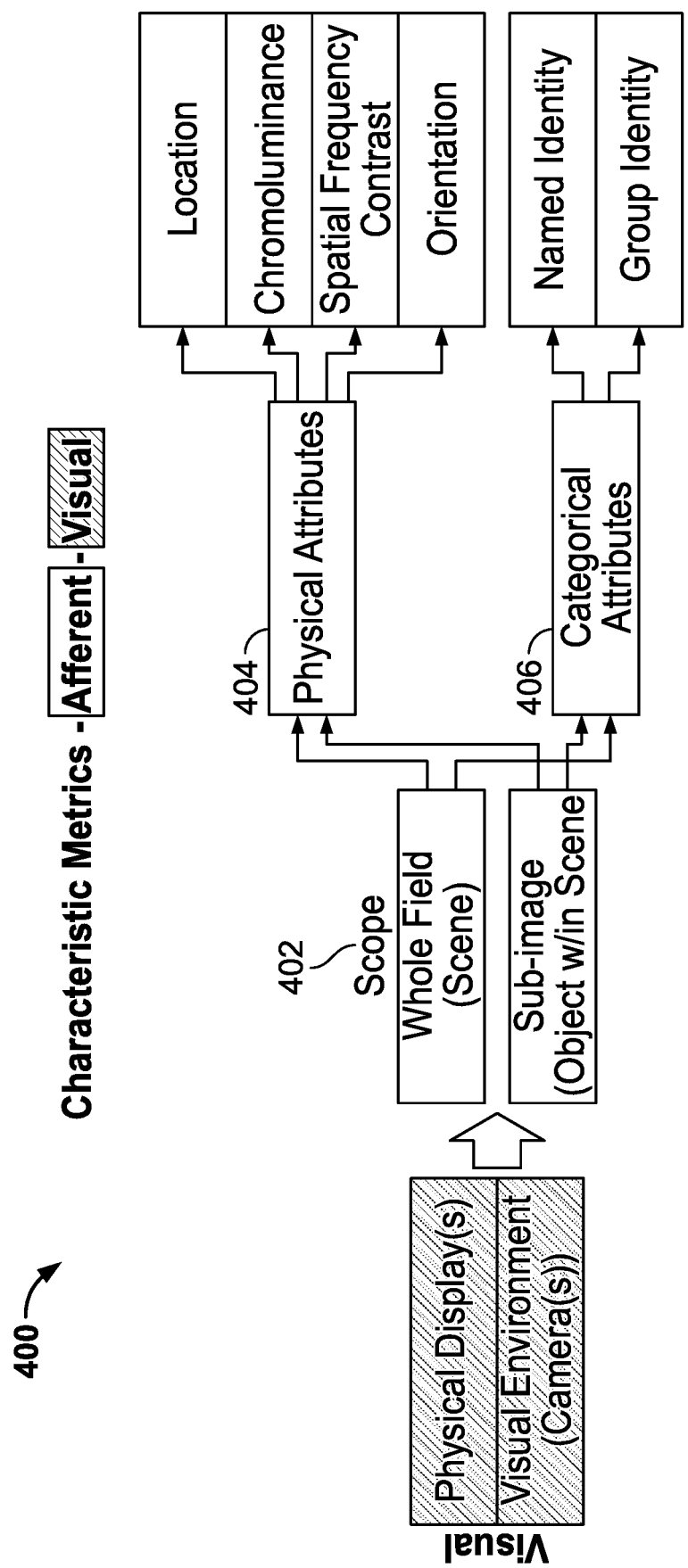
FIG. 4 illustrates characteristic metrics for visual data, in accordance with an embodiment of the present specification.

FIG. 4 is a block diagram 400 illustrating characteristic metrics for visual data, in accordance with an embodiment of the present specification. Characteristic metrics may characterize a user session and may be time-averaged. Referring FIG. 4, scope 402 may refer to whether the visual data is for an entire scene (the whole visual display or the whole image from a user-head-mounted camera). Physical attributes 404 may refer to objective measures of the scene or objects within it. They may include location relative to the retina, head and body, an orthogonal 3-D chromoluminance; and contrast vs. spatial frequency vs. orientation. Categorical attributes 406 may be named properties of the image, which may include named identity of an object, and/or the group identity.

Visual stimuli may generally be taken in as digital, true color images (24-bit) either generated by an application (image data provided by app directly) or taken from recorded video (e.g. from a head mounted camera). Images and video may be compressed in a lossy fashion; where weighted averaging of data may account for lossy compression, but otherwise image processing would proceed the same regardless. A developer may choose to provide information about the presentation of a stimulus which may allow for the skipping of some image processing steps and/or allow for post hoc rendering of scenes for analysis. Visual stimuli may include, but are not limited to the following components: objects, size, chromatic distance, luminance contrast, chromatic contrast, spatial feature extraction, saliency maps and/or temporal dynamics.

Objects (stimuli) may be identified in an image (or video frame) either by information from the application itself or found via machine learning (Haar-like features classification cascade, or similar). Once identified, the pixels belonging to the object itself (or within a bounding area corresponding to a known size centered on the object) will be tagged as the "object". The pixels in an annulus around the object (necessarily within the boundaries of the image/scene itself) with the same width/height of the object (i.e. an area 3× the object width and 3× the object height, excluding the central area containing the object) will be tagged as the "surround". If another image exists of the same exact area of the surround, but without the object present (thus showing what is "behind" the object), that entire area without the object may be tagged as the "background". Metrics may be calculated relative to the surround and also relative to the background when possible. Object segments or parts may be used to break objects down into other objects and may also be used for identity or category variables. Objects need not correspond to physical objects and may include regions or boundaries within a scene or comprise a single image feature (e.g. an edge).

Object size is an important feature for determining acuity, or from known acuity predicting whether a user will detect or correctly identify an object. The object size may be defined as a width and height, either based on the longest horizontal and vertical distance between pixel locations in the object or as the width and height of a rectangular bounding box defining the object's location. Smaller features that may be necessary to successfully detect or discriminate the object from others may be located within the object. It may be assumed that the smallest feature in an object is 10% of the smaller of its two dimensions (width and height). It may also be assumed the smallest feature size is proportional to the size of a pixel on the display for a given viewing distance. The smallest feature size may be more explicitly found either by analysis of a Fourier transform of the image or examining key features from a Han-like feature classification cascade (or similar machine learning based object detection) trained on the object.

The first of two breakdowns by color, chromatic distance is a measure of the color difference between the object and its surround/background, independent of any luminance differences. Red, green and blue values may be independently averaged across all pixels of the object and all pixels of the surround/background. These mean RGB values will be converted into CIE Tristimulus values (X, Y and Z) and then into CIE chromaticity (x and y) using either standard conversion constants or constants specific to the display used (when available). In an embodiment, conversion constants for conversion from RGB to XYZ, taken from Open CV function 'cvtColor' based on standard primary chromaticities, a white point at D65, and a maximum, white luminance of 1, is:

$$\begin{bmatrix} X \\ Y \\ Z \end{bmatrix} \leftarrow \begin{bmatrix} 0.412453 & 0.357580 & 0.180423 \\ 0.212671 & 0.715160 & 0.072169 \\ 0.019334 & 0.119193 & 0.950227 \end{bmatrix} \cdot \begin{bmatrix} R \\ G \\ B \end{bmatrix}$$

In this embodiment, RGB is converted to xy using the following:

$$x = \frac{X}{X+Y+Z}$$
$$y = \frac{Y}{X+Y+Z}$$

The absolute distance between the chromaticity of the object and that of the surround/background will be logged as the chromatic distance. Next, a line will be drawn from the midpoint between the two chromaticities and each of the three copunctal points for L, M and S cones. These lines are confusion lines for L, M and S cone deficiencies, along which someone missing one of those cone types would be unable to discriminate chromaticity. The component of the line between object and surround/background chromaticity parallel to each of these three confusion lines will be logged as the L, M and S specific chromatic distances.

Figure 5:
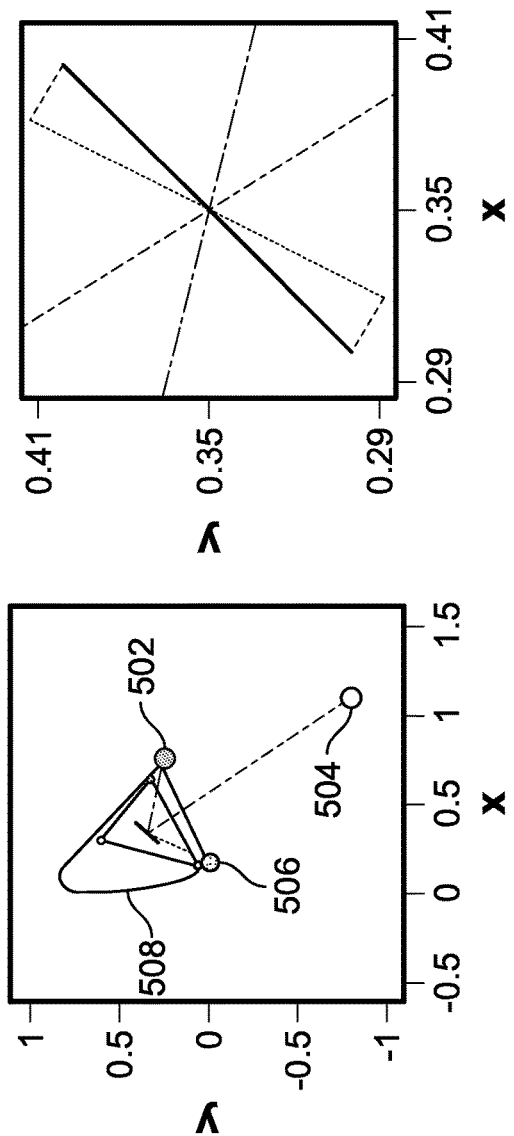
FIG. 5 provides a graphical presentation of color pair confusion components, in accordance with an embodiment of the present specification.

FIG. 5 provides a graphical presentation of color pair confusion components, in accordance with an embodiment of the present specification. Referring to the figure, a line 508 is drawn between the two chromaticities given. As seen in the figure, three large dots—red 502, green 504, and blue 506 are copunctal points for L, M and S cones, respectively. From each dot extends a similarly color-coded, dashed line. Bold line 508 has a mid-point where the three, dashed lines intersect. Based on the angle between line 508 and the lines drawn from the midpoint to each of the copunctal points, the parallel component of that line for each of the three resulting confusion lines is determined. In embodiments, the closer to the parallel line between the colors is to a particular confusion line, the more difficult it will be for someone with a deficiency of the corresponding cone to discriminate. The component length divided by the total length (the quotient will be in the interval [0,1]) would be roughly the probability of the colors being confused.

Figure 6:
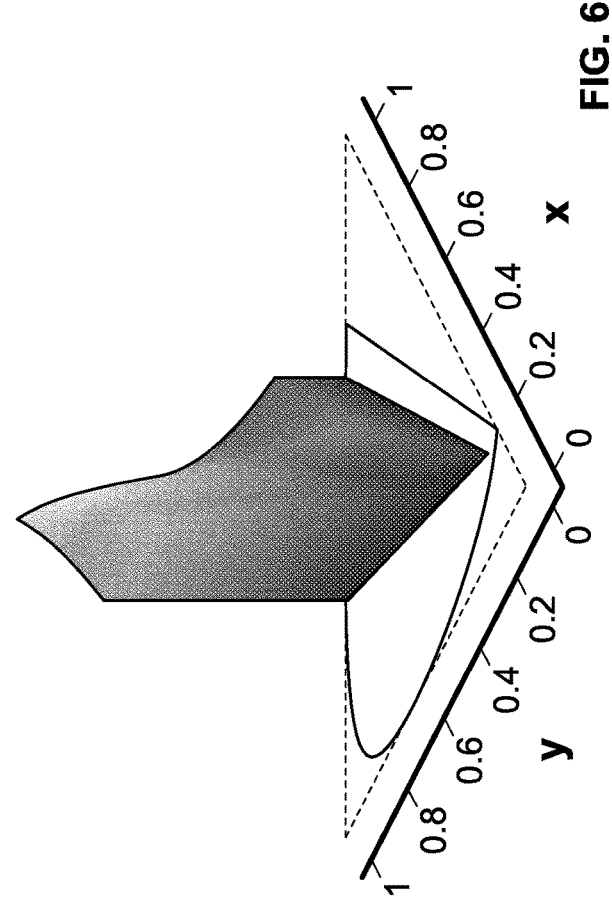
FIG. 6 shows a graph illustrating how luminance may be found for a given chromaticity that falls on the top surface of the display gamut projected into 3D chromoluminance space.

FIG. 6 shows a graph illustrating how luminance may be found for a given chromaticity that falls on the top surface of the display gamut projected into 3D chromoluminance space. The graph shows a projection of a full display gamut for a computer screen into CIE 1931 chromoluminance space. While the RGB space used to define the color of pixels on a display can be represented by a perfect cube, the actual physical property of luminance is somewhat complexly derived from those values, represented by the shape seen in FIG. 6. Luminance contrast may be defined in three ways. Generally the context of an analysis will suggest which one of the three to use, but all three may be computed for any object and its surround/background. For instances where a small object is present on a large, uniform background (e.g. for text stimuli), Weber contrast may be computed using the CIE Tristimulus values Y (corresponding to luminance) calculated from the mean RGB of the object and of the surround/background. Here it is assumed that the average luminance is roughly equal to the surround luminance. Weber contrast can be positive or negative and is theoretically unbounded. For object/surrounds that are periodic in nature, and especially with gradients (e.g. a sine wave grating), Michelson contrast may be computed from the minimum and maximum luminance values in the stimulus. Michelson contrast will always be a value between 0 and 1. For most cases it will be necessary to compute contrast from all of the pixel values, instead of from a mean or from the minimum and maximum. The RMS contrast (root mean square, or standard deviation) can be found by taking the standard deviation of the CIE Tristimulus value Y for all pixels. The RMS contrast of the object is one measure. The RMS contrast of the object relative to the RMS contrast of the surround/background is another. Finally, the RMS contrast of the object and surround together is yet a third measure of RMS contrast that can be used.

Chromatic contrast may be calculated on any pair of chromaticity values, independently, in all of the ways described above for luminance contrast. The most useful of these will either be the a* and b* components of CIELAB color space, or the L vs. M and S vs. LM components of cone-opponent color space. For any pair of dimensions, the Weber, Michelson and/or RMS contrast may be calculated, depending on the type of stimulus being analyzed. In addition, RMS contrast will be calculated for L, M and S cone deficiencies. CIE chromaticity values for all pixels will be converted into three sets of polar coordinates centered on the L, M and S copunctal points. In an embodiment, the following equation is used to convert Cartesian coordinates to polar coordinates, with an option to provide center points other than [0,0]:

$$\theta = \tan^{-1}\left(\frac{y - y_c}{x - x_c}\right)$$

$$\text{Radius} = \sqrt{(y - y_c)^2 + (x - x_c)^2}$$

RMS contrast may be calculated based on the radius coordinates for each conversion.

In addition to finding objects, algorithms may also identify prominent features present in a scene, or within objects, that may capture attention, be useful for a task the user is performing or otherwise be of interest as independent variables to correlate with behavior. Edges, those inside identified objects and otherwise, may be targets for fixations or other responses and their positions may be responsible for observed positional errors in responding and be worth correlating with correct and incorrect responses. Regions, contours, surfaces, reflections, shadows and many other features may be extracted from this data.

Saliency Maps refer to data that are collected from user interactions to inform models of saliency for future analysis of stimulus scenes. Edges, contours and other image features may be used to measure saliency and predict where user responses, including eye gaze fixations, may fall. Multiple algorithms may be applied to highlight different types of features in a scene.

Temporal Dynamics are also important because features of a visual display or environment, and any objects and object features thereof, may change over time. It will be important to log the time of any change, notably: appearance/disappearance or change in brightness/contrast of objects or features, motion start/stop or abrupt position change (in x, y, z planes), velocity change (or acceleration or any higher order time derivative of position) and any and all changes in state or identity of objects or features. Changes in chromaticity or luminance of objects or features should also be logged. Secondary changes in appearance resulting from changes in orientation or pose of an object or the object's position relative to the surround/background may also be logged.

Auditory Information

Referring back to FIG. 3, auditory information 308 may be received from audio output such as speakers, and the environment by using microphones. In an embodiment auditory information 308 may be available in raw, waveform files or in more descriptive terms (e.g. this audio file played at this time).

Figure 7:
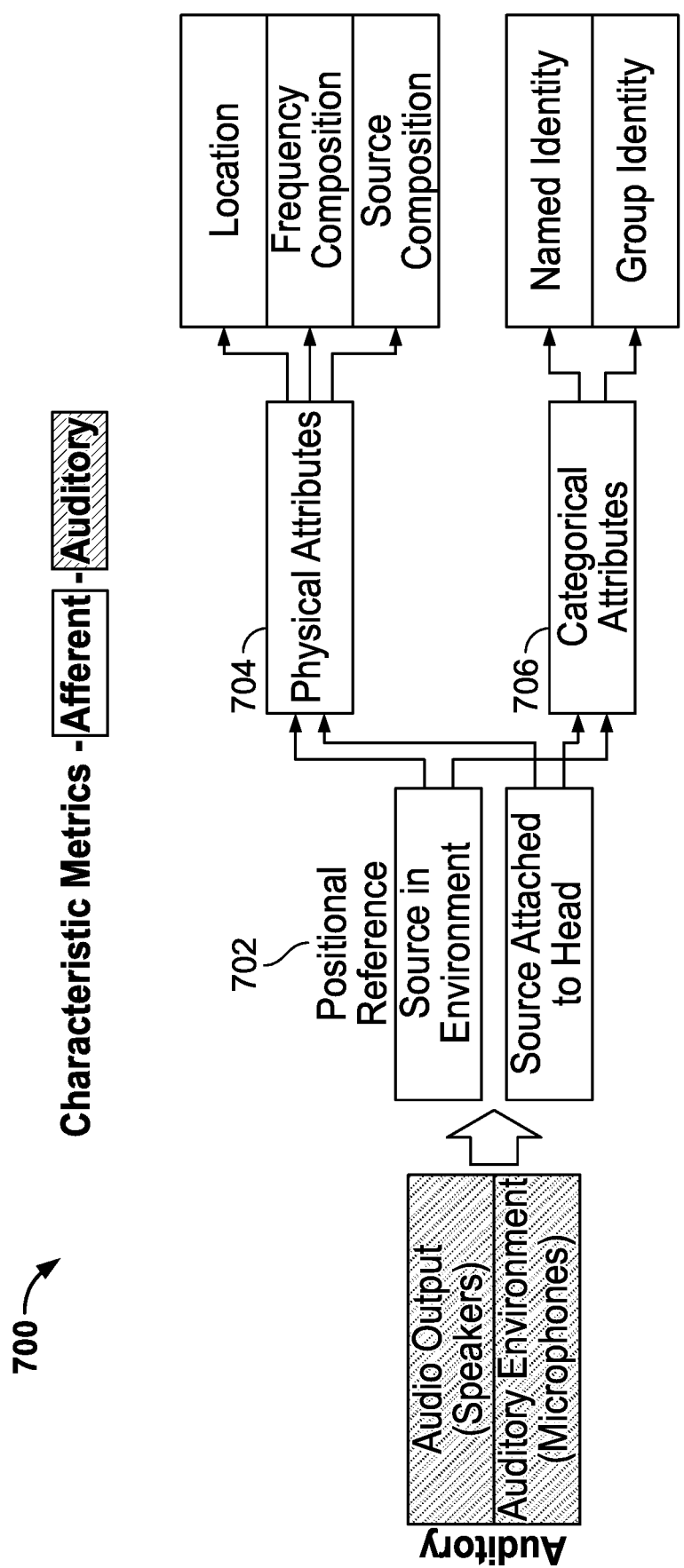
FIG. 7 illustrates characteristic metrics for auditory information, in accordance with an embodiment of the present specification.

FIG. 7 illustrates characteristic metrics 700 for auditory information 308, in accordance with an embodiment of the present specification. Referring to FIG. 7, a positional reference 702 may be noted to identify the location of sounds. The position, relative to a user's head, of an object or speaker in the environment will vary as they move their head. The position of a virtual source perceived through headphones may not change as the user turns their head (unless head tracking and sound processing work together to mimic those changes).

The physical attributes 704 of sound may include their location (derived from intensity, timing and frequency differences between the ears), frequency composition (derived from the waveform), and the composition of different sources. Categorical attributes 706 may be named properties of the image, which may include named identity of an object, and/or the group identity and may follow a similar description as for visual stimuli.

Auditory (Sound) stimuli may generally be taken in as digital waveforms (with varying spatial and temporal resolution or bitrate and possible compression) either generated by an application or taken from recorded audio (e.g. head mounted microphones, preferably binaural). Compression parameters, if any, may be recorded. Developers may choose to provide information about the presentation of a stimulus which may allow for the skipping of some processing. Visual information may be used to model the audio environment so that sound reflections or obscurations can be taken into account. Audio stimuli may be broken down to include the following parameters: Fourier Decomposition, Head-Centric Position, Sound Environment, and/or Objects.

Fourier Decomposition may be performed to break sound waves into components based on sound objects. Time-domain waveform data may be transformed into the frequency domain such that the amplitude and phase of different audio frequencies over time may be analyzed. This will allow the utilization of sound parameters (e.g. frequency, amplitude, wavelength, shape and envelope, timbre, phase, etc.) as independent variables.

Head-Centric Position or head tracking data may be necessary for environmental sounds. The position of sound sources relative to a user's ears may be derived, and whenever possible the sound waveforms as they exist at the user's ears may be recorded (ideally from binaural, head-mounted microphones). Binaural headset sound sources (e.g. headphones/earphones) may obviate the necessity for this.

Similarly, tracking data for body and/or limbs may be necessary for environmental sounds. The position of sound sources relative to a user's body and limbs may be derived. This data may be related to head tracking data identified for environmental sounds. The data may enable understanding of how body and limbs react with the movement of head.

Sound Environment is not critical in most common use cases (e.g. sound is coming from headset or from directly in front of the user), but will be important for considering environmental sounds to which users are anticipated to respond. Objects in the environment that reflect and/or block sound (commonly frequency specific) may change the apparent source location and other frequency dependent features of a sound. It may be useful to roughly characterize the physical environment as it affects the propagation of sound from its sources to the user.

Audio objects may be detected and segmented out using the same type of machine learning algorithms (Haar-like feature classification cascades or similar) that are used for detecting and segmenting out visual objects. This should be used whenever possible to obtain accurate audio event details and may also be useful for extracting audio parameters used by the auditory system for localization.

Most analysis may revolve around visual and (to a lesser extent) auditory stimuli occurring discretely in time. Other stimuli may include those sensed in other modalities (e.g. touch, taste, smell, etc.) or general environmental state variables that define the context of user interactions with applications (e.g. ambient lighting and background audio).

Examples of other stimuli may include the following:

Haptic Stimuli, where developers may choose to use haptic feedback mechanisms and, if they so choose, provide details about the nature and timing of those events. Haptic stimulation may also be derived via direct recording (unlikely) or derived from other sources (e.g. hearing the buzz of a physical vibration via microphone).

Other Modality Stimuli, where developers may be able to initiate smell, taste, temperature, pressure, pain or other sensation at discrete times creating stimulus events not already discussed. As with haptic stimuli, any record of such stimulation would best come directly from the application itself via function calls.

Environmental Stimuli, or stimuli that do not occur discretely in time and are either of constant state or steadily repeating, may provide important context for the discrete stimuli and responses that occur in a session. Ambient light levels may affect contrast sensitivity, baseline pupil size, circadian patterns and other physiological states of the user. Ambient sounds may affect auditory sensitivity, may mask certain auditory stimuli and also affect physiological and other states of the user. The time of day may also be an important variable for categorization and correlation.

Though perhaps not readily recorded by an application, user input could provide information about sleep patterns, diet and other physiologically relevant state variables as well as categorical descriptions of the space including temperature, pressure, humidity (which may also be derived from location and other services).

Spatial Information

Referring back to FIG. 3, in an embodiment, spatial information 310 may consist of descriptions of the setting around user 302. This may include spatial orientation of user 302 and physical space around user 302.

In an embodiment, setting is an environment in which interactions between user 302 and the app take place. Setting data may refer to things that are mostly static during a session including the physical setting, ambient light levels, room temperature, and other types of setting information. In embodiments, spatial information 310 is a part of the setting data. Setting data may generally be constant throughout a session with user 302 and therefore may not be broken down into "events" as described earlier. Setting data may pertain to a physical setting or may relate to personal details of user 302.

Physical setting data may correspond to any description of the physical space, such as and not limited to a room or an outdoor setting, and may be useful to categorize or filter data. In an exemplary embodiment, physical setting data such as the ambient lighting present, may directly affect measures of pupil size, contrast sensitivity and others. Lighting may affect quality of video eye tracking, as well as any afferent events derived from video recording of a scene. Similarly, environmental sounds may affect users' sensitivity as well as the ability to characterize afferent events derived from audio recording.

Personal details of a user may pertain to any personal, largely demographic, data about the user or information about their present physiological or perceptual state (those that will remain largely unchanged throughout the session). This data may also be useful for categorization and filtering. Personal details may include any information regarding optics of the user's eyes (for example, those derived from knowledge of the user's eyeglass or contact prescription). Personal details may also include diet related information, such as recent meal history. Further, time, duration, and quality of most recent sleep period, any psychoactive substances recently taken in (e.g. caffeine) and recent exercise or other physical activity may all impact overall data.

Efferent Data

Eye Tracking

Video eye tracking and electrooculography provide information about eye movements, gaze direction, blinking and pupil size. Derived from these are measures of vergence, fatigue, arousal, aversion and information about visual search behavior. Information pertaining to eye movements include initiation, duration, and types of pro-saccadic movements (toward targets), anti-saccadic movements (toward un-intended target), the amount of anti-saccadic error (time and direction from intended to unintended target), smooth pursuit, gaze with fixation duration, pupil changes during movement and during fixation, frequency and velocity of blink rate, as well as frequency and velocity of eye movements. Information pertaining to vergence may include both convergence and divergence—in terms of initiation and duration. Combined with information about the visual scene, measures of accuracy, search time and efficiency (e.g. minimizing number of saccades in search) can be made.

Autonomic measures derived from video eye tracking data may be used to guide stimulus selection towards those that increase or decrease arousal and/or aversion. Summary information about gaze position may indicate interest or engagement and likewise be used to guide stimulus selection.

Figure 8:
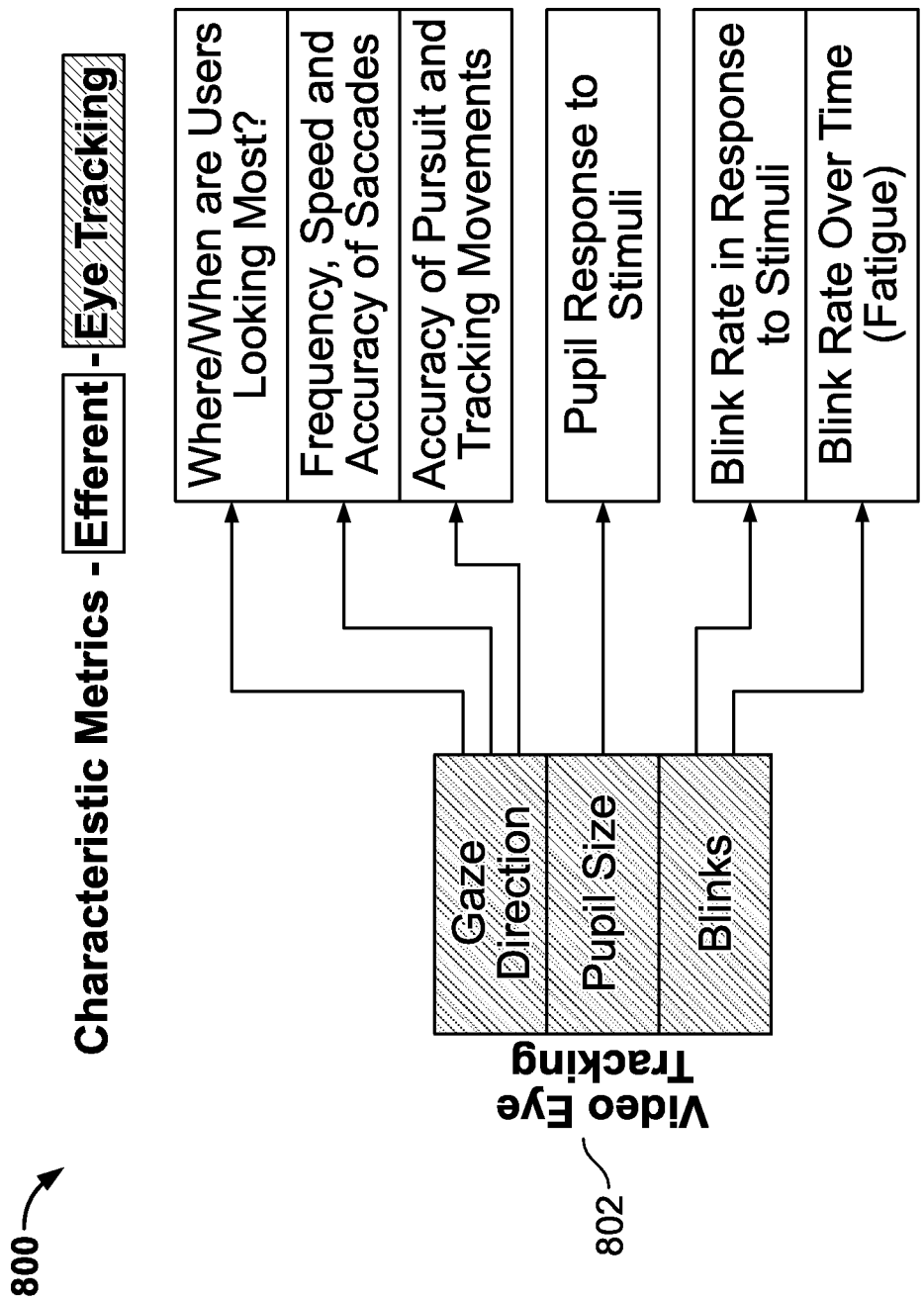
FIG. 8 illustrates characteristic metrics for eye tracking, in accordance with an exemplary embodiment of the present specification.

Referring to FIG. 3, efferent data sources 306 may include video eye tracking data 312. Data 312 may measure gaze direction, pupil size, blinks, and any other data pertaining to user's 302 eyes that may be measured using a Video Eye Tracker (VET) or an electro-oculogram. This is also illustrated in FIG. 8, which shows characteristic metrics 800 for eye tracking, in accordance with an exemplary embodiment of the present specification. Video eye tracking 802 generally involves recording images of a user's eye(s) and using image processing to identify the pupil and specific reflections of known light sources (typically infrared) from which may be derived measures of pupil size and gaze direction. The angular resolution (of eye gaze direction) and temporal resolution (frames per second) may limit the availability of some measures. Some measures may be recorded as discrete events, and others recorded over time for analysis of trends and statistics over epochs of time.

Gaze Direction

Software, typically provided with the eye tracking hardware, may provide calibrated estimates of gaze direction in coordinates tied to the display used for calibration. It may be possible/necessary to perform some of this conversion separately. For head mounted units with external view cameras the gaze position may be in head centric coordinates or in coordinates relative to specific objects (perhaps provided reference objects) in the environment. It is assumed that gaze direction will be provided at some rate in samples per second. Most of the following metrics will be derived from this stream of gaze direction data: saccade, pursuit, vergence, patterns, and/or microsaccades.

Saccade: Prolonged periods of relatively fixed gaze direction separated by rapid changes in gaze (over a matter of milliseconds) may be logged as "fixations" and the jumps in between as "saccades". Fixations will be noted for position, start and end time and duration. In some cases they may also be rated for stability (variability of gaze direction during fixation). Saccades will be noted for their direction (angle), speed and distance. It is worth noting, and it will generally be assumed, that there is a period of cortical suppression during saccades when visual information is not (fully) processed. This saccadic suppression may be exploited by developers to alter displays without creating a percept of motion, appearance or disappearance among display elements.

Pursuit: Pursuit eye movements may be characterized by smooth changes in gaze direction, slower than typical saccades (and without cortical suppression of visual processing). These smooth eye movements generally occur when the eyes are pursuing/tracking an object moving relative to head facing direction, a stationary object while the head moves or moving objects while the head also moves. Body or reference frame motion can also generate pursuit eye movements to track objects. Pursuit can occur in the absence of a visual stimulus based on the anticipated position of an invisible or obscured target.

Vergence: This measure may require relatively fine resolution gaze direction data for both eyes simultaneously so that the difference in gaze direction between eyes can be used to determine a depth coordinate for gaze. Vergence is in relation to the distance of the object in terms of the user to measure objects between the near point of convergence and towards infinity in the distance—all of which may be modelled based off the measurements of vergence between convergence and divergence.

Patterns: Repeated patterns of eye movements, which may be derived from machine learning analysis of eye gaze direction data, may be used to characterize response events, states of user interaction or to measure effects of adaptation, training or learning. Notable are patterns during visual search for targets or free viewing of scenes towards the completion of a task (e.g. learning of scene details for later recognition in a memory task). Eye movement patterns may also be used to generate models for creating saliency maps of scenes, guiding image processing.

Microsaccades: With relatively sensitive direction and time resolution it may be possible to measure and characterize microsaccadic activity. Microsaccades are generally present during fixation, and are of particular interest during rigid or prolonged fixation. Feedback into a display system may allow for creating images that remain static on the retina resulting in Troxler fading. Microsaccades are not subject to conscious control or awareness.

Sample questions concerning eye tracking metrics that may be answered over a period of time may include: where are users looking the most (potentially in response to repeating events), how fast and accurate are saccadic eye movements, how rapidly are users finding targets, are users correctly identifying targets, how accurate is pursuit/tracking, are there preferences for certain areas/stimuli.

During free viewing or search, fixations (relatively stable eye gaze direction) between saccades typically last on the order of 200-300 milliseconds. Saccades have a rapidly accelerating velocity, up to as high as 500 degrees per second, ending with a rapid deceleration. Pursuit eye movements occur in order to steadily fixate on a moving object, either from object motion or head motion relative to the object or both. Vergence eye movements are used to bring the eyes together to focus on near objects. Vestibular eye movements are compensatory eye movements derived from head and/or body movement.

Reference is made to WO2015003097A1 entitled "A Non-Invasive Method for Assessing and Monitoring Brain". In an example, a pro-saccade eye tracking test is performed. The pro-saccade test measures the amount of time required for an individual to shift his or her gaze from a stationary object towards a flashed target. The pro-saccade eye tracking test may be conducted as described in The Antisaccade: A Review of Basic Research and Clinical Studies, by S. Everling and B. Fischer, Neuropsychologia Volume 36, Issue 9, 1 Sep. 1998, pages 885-899 ("Everling"), for example.

The pro-saccade test may be performed while presenting the individual with a standardized set of visual stimuli. In some embodiments, the pro-saccade test may be conducted multiple times with the same or different stimuli to obtain an average result. The results of the pro-saccade test may comprise, for example, the pro-saccade reaction time. The pro-saccade reaction time is the latency of initiation of a voluntary saccade, with normal values falling between roughly 200-250 ms. Pro-saccade reaction times may be further sub-grouped into: Express Pro-Saccades: 80-134 ms; Fast regular: 135-175 ms; Slow regular: 180-399 ms; and Late: (400-699 ms).

Similarly, an anti-saccade eye tracking test may be performed. The anti-saccade test measures the amount of time required for an individual to shift his or her gaze from a stationary object away from a flashed target, towards a desired focus point. The anti-saccade eye tracking test can be conducted as described in Everling, for example. In some examples, the anti-saccade test may also measure an error time and/or error distance; that is, the amount of time or distance in which the eye moves in the wrong direction (towards the flashed target). The anti-saccade test may be performed using the standardized set of visual stimuli. The results of the anti-saccade test may comprise, for example, mean reaction times as described above for the pro-saccade test, with typical mean reaction times falling into the range of roughly 190 to 270 ms. Other results may include initial direction of eye motion, final eye resting position, time to final resting position, initial fovea distance (i.e., how far the fovea moves in the direction of the flashed target), final fovea resting position, and final fovea distance (i.e., how far the fovea moves in the direction of the desired focus point).

Also, a smooth pursuit test may be performed. The smooth pursuit test evaluates an individual's ability to smoothly track moving visual stimuli. The smooth pursuit test can be conducted by asking the individual to visually follow a target as it moves across the screen. The smooth pursuit test may be performed using the standardized set of visual stimuli, and may be conducted multiple times with the same or different stimuli to obtain an average result. In some embodiments, the smooth pursuit test may include tests based on the use of fade-in, fade-out visual stimuli, in which the target fades in and fades out as the individual is tracking the target. Data gathered during the smooth pursuit test may comprise, for example, an initial response latency and a number of samples that capture the fovea position along the direction of motion during target tracking. Each sampled fovea position may be compared to the position of the center of the target at the same time to generate an error value for each sample.

For more sensitive tracking hardware, it may also be possible to measure nystagmus (constant tremor of the eyes), drifts (due to imperfect control) and microsaccades (corrections for drift). These will also contribute noise to gross measurements of gaze position; as a result fixations are often characterized by the mean position over a span of relatively stable gaze position measures. Alternatively, a threshold of gaze velocity (degrees/second) can be set, below which any small movements are considered to be within a fixation.

Saccades require time to plan and execute, and a delay, or latency, of at least 150 ms is typical after, for example, the onset of a visual stimulus eliciting the saccade. Much can be said about the latency before a saccade and various contexts that may lengthen or shorten them. The more accurate information we have regarding the relative timing of eye movements and events occurring in the visual scene, the more we can say about the effect of stimulus parameters on saccades.

Although usually correlated, shifts in attention and eye gaze do not necessarily have to happen together. In some contexts it may be efficient for the user to direct attention to a point in their visual periphery, for example to monitor one location while observing another. These scenarios may be useful for generating measures related to Field of View and Multi-Tracking.

It is possible to use image processing techniques to highlight regions within a scene of greater saliency based on models of the visual system. For example areas of greater high-spatial-frequency contrast (i.e. edges and lines) tend to capture attention and fixations. It is possible within a specific context to use eye gaze direction to develop custom saliency maps based on the information available in the visual scene combined with whatever tasks in which an observer may be engaged. This tool can be used to highlight areas of interest or greater engagement.

Pupil Size

Pupil size may be measured as part of the image processing necessary to derive gaze direction. Pupil size may generally change in response to light levels and also in response to certain stimulus events via autonomic process. Pupil responses are not subject to conscious control or awareness (except secondarily in the case of extreme illumination changes). Sample questions concerning eye tracking metrics that may be answered over a period of time may include: how are the pupils responding to different stimuli, how are the pupils behaving over time.

Pupil diameter generally falls between 2 and 8 mm at the extremes in light and dark, respectively. The pupil dilates and constricts in response to various internal and external stimuli. Due to differences in baseline pupil diameter, both among observers and due to ambient lighting and physiological state, pupil responses may generally be measured as proportions of change from baseline. For example, the baseline pupil diameter might be the diameter at the moment of an external stimulus event (image appears), and the response is measured by the extent to which the pupil dilates or constricts during the 1 second after the stimulus event. Eye color may affect the extent of constriction, and age may also be a factor.

In addition to responding to light, accommodation for distance and other spatial and motion cues, pupil diameter will often be modulated by cognitive load, certain imagery and reading. Pupil diameter may be modulated during or at the termination visual search. Proportional changes can range from a few to tens of percentage points.

Thresholds for determining computationally if a response has been made will vary depending on the context and on the sensitivity of the hardware used. Variations in ambient lighting and/or the mean luminance of displays will also have a large influence on pupil diameter and proportional changes, so thresholds will need to be adaptable and likely determined by the data itself (e.g. threshold for dilation event itself being a percentage of the range of pupil diameter values recorded within a session for one user).

Reference is again made to WO2015003097A1 titled "A Non-Invasive Method for Assessing and Monitoring Brain". In an example, pupillary response is assessed. Pupillary response is often assessed by shining a bright light into the individual's eye and assessing the response. In field settings, where lighting is difficult to control, pupillary response may be assessed using a standardized set of photographs, such as the International Affective Picture System (IAPS) standards. These photographs have been determined to elicit predictable arousal patterns, including pupil dilation. The pupillary response test may be performed using a variety of stimuli, such as changes to lighting conditions (including shining a light in the individual's eyes), or presentation of photographs, videos, or other types of visual data. In some embodiments, the pupillary test may be conducted multiple times with the same or different stimuli to obtain an average result. The pupillary response test may be conducted by taking an initial reading of the individual's pupil diameter, pupil height, and/or pupil width, then presenting the individual with visual stimuli to elicit a pupillary response. The change in pupil dilation (e.g., the change in diameter, height, width, and/or an area calculated based on some or all of these measurements) and the time required to dilate are measured. The results of the pupillary response test may include, for example, a set of dilation (mydriasis) results and a set of contraction (miosis) results, where each set may include amplitude, velocity (speed of dilation/constriction), pupil diameter, pupil height, pupil width, and delay to onset of response.

Blinks

Video eye trackers, as well as less specialized video imaging of a user's face/eye region, may detect rapid or prolonged periods of eye closure. Precautions may be taken as loss of acquisition may also be a cause for periods of data loss. Blink events, conscious or reflexive, and blink rates over time related to measures of fatigue or irritation may be recorded. Sample questions concerning eye tracking metrics are mentioned in FIG. 8. In embodiments, these are questions that may be answered over a period of time and may include: are the users blinking in response to the onset of stimuli, is the blink rate changing in response to the stimuli, is the blink rate changing overall, does the blink rate suggest fatigue.

Normal blinking rates among adults are around 10 blinks per minute at rest, and generally decreases to around 3 blinks per minute during focused attention (e.g. reading). Other properties of blinks, for example distance/speed of eyelid movement and durations of various stages within a blink, have been correlated with error rates in non-visual tasks (for example, using auditory stimulus discrimination) and other measures; whenever possible it may be advantageous to use video recordings to analyze eyelid position in detail (i.e. automated eyelid tracking). Blink durations longer than 150 ms may be considered long-duration blinks.

As with most measures, proportional changes from baseline may be more valuable than absolute measures of blink frequency or average duration. Generally, significance can be assigned based on statistical measures, meaning any deviation is significant if it is larger than the general variability of the measure (for example as estimated using a t-test).

Manual Inputs

Figure 9:
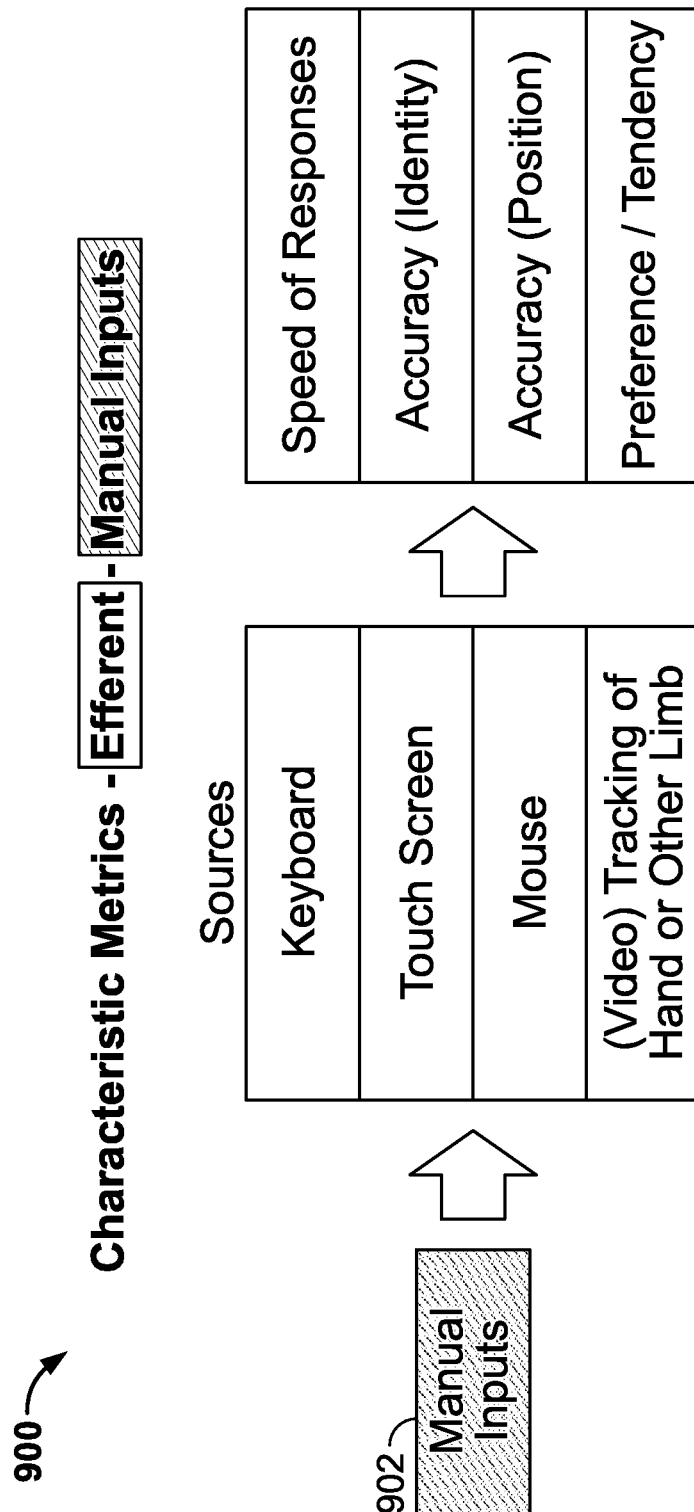
FIG. 9 illustrates characteristic metrics for manual input, in accordance with an embodiment of the present specification.

Referring back to FIG. 3, another efferent data source 306 may be manual input 314. Which have been a traditional tool of computer interaction and may be available in many forms. Exemplary manual inputs 314 of interest include input identity (key pressed), any other gesture, position coordinates (x, y, z) on a touch screen or by a mouse, and/or (video) tracking of hand or other limb. FIG. 9 illustrates characteristic metrics 900 for manual inputs 902, in accordance with an embodiment of the present specification.

Sample questions concerning manual input metrics that may be answered over a period of time may include: where are the users clicking/touching the most (potentially in response to repeating events), how fast and accurate are the clicks/touches, how rapidly are users finding targets, are users correctly identifying targets, how accurate is tracking, are there preferences for certain areas/stimuli, what kind of grasping/touching motions are the users making, how is the hand/eye coordination, are there reflexive actions to virtual stimuli.

Responses made with the fingers, hands and/or arms, legs, or any other part of the body of users may generally yield timing, position, trajectory, pressure and categorical data. These responses may be discrete in time, however some sustained or state variable may be drawn from manual data as well. Following analytic response metrics may be derived from manual responses: category, identity, timing, position, and/or trajectory.

Category: In addition to categories like click, touch, drag, swipe and scroll there may be sub categories like double click, tap or push, multi-finger input, etc. Any variable that differentiates one action from another by category that is detectable by an application may be important for differentiating responses (and will likely be used for that purpose by developers).

Identity: Whenever multiple input modalities exist for the same type of response event, most notably the keys on a computer keyboard, or any other gesture that may be possible in a media environment, the identity of the input may be recorded. This also includes directions indicated on a direction pad, mouse buttons clicked and, when possible, the area of a touchpad touched (independent of cursor position), or any other gesture.

Timing: The initiation and ending time of all responses may be recorded (e.g. a button press will log both the button-down event and the button-up event), and from that response durations can be derived. This timing information will be key to connecting responses to the stimuli that elicited them and correlating events in time.

Position: For visual interfaces, the position may be in display coordinates. Positions may be singular for discrete events like clicks or continuously recorded at some reasonable rate for tracing, dragging, etc. When possible these may also be converted to retinal coordinates (with the combination of eye gaze tracking). By understanding position, a topography of the retina may be done, and areas of the retina may be mapped in relationship to their specific functions further in relationship to the brain, body, endocrine, and autonomic systems. For gestures recorded by video/motion capture the body-centric position will be recorded along with the location of any cursor or other object being controlled by the user.

Trajectory: For swipe, scroll and other dynamic gestures it may be possible to record the trajectory of the response (i.e. the direction and speed as a vector) in addition to any explicit position changes that occur. This will, in fact, likely be derived from an analysis of rapid changes in position data, unless the device also provides event types for these actions.

Head Tracking

Head tracking measures are largely associated with virtual, augmented, and mixed reality displays. They can provide measures of synchrony with displayed visual environments, but also of users' reactions to those environments. Orienting towards or away from stimuli, compensatory movements in line or not in line with the displayed visual environments and other motion behavior can be used to derive similar, though less precise, measures similar to those from eye tracking. Those derived measures associated with arousal, fatigue and engagement can be modified as previously stated.

If head movements, particularly saccadic head movements, prove to be a source of mismatch and discomfort for users it may be desirable to modify displays to reduce the number of such head movements. Keeping display elements within a region near head-center and/or encouraging slower changes in head-facing may reduce large head movements. With regards to individual differences: some users will move their heads more than others for the same scenario. It may be possible to train head movers to reduce their movements.

Figure 10:
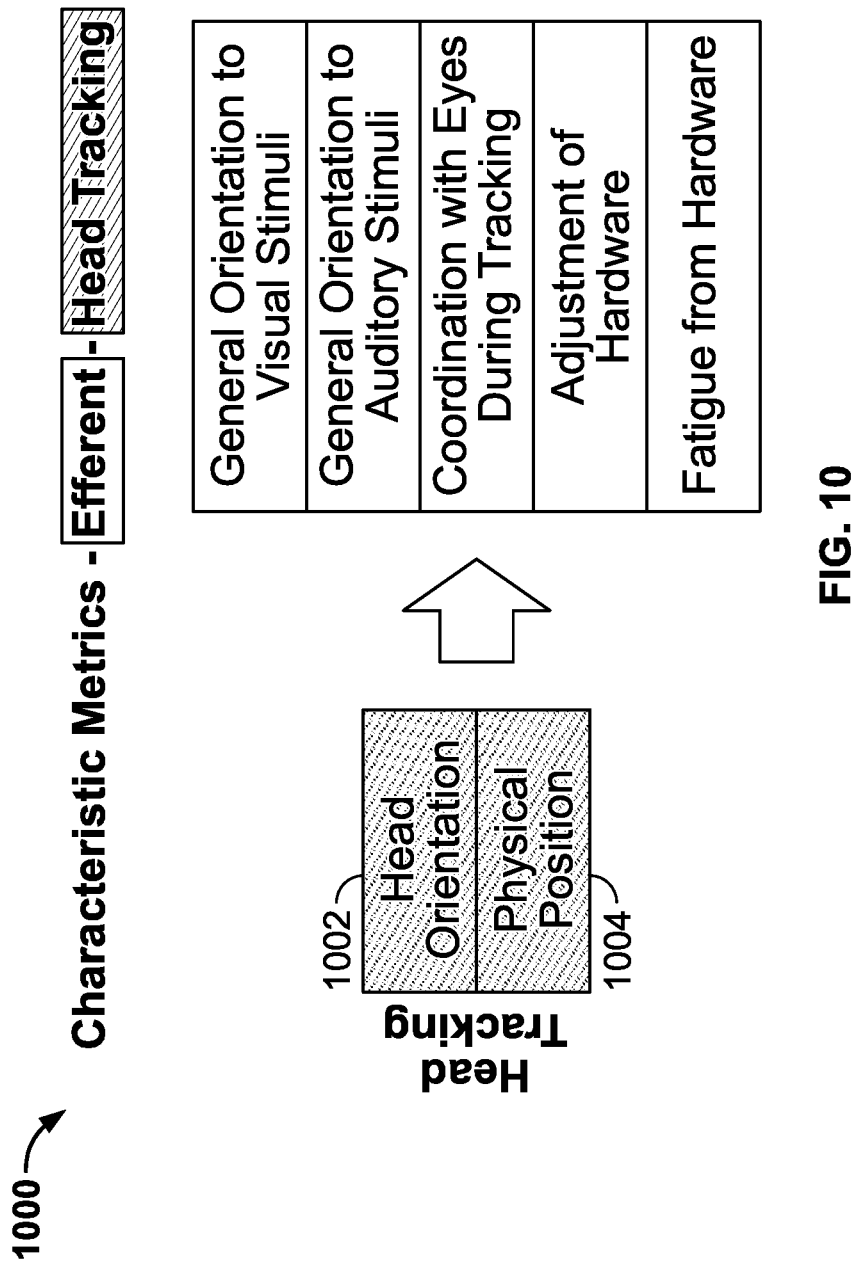
FIG. 10 illustrates characteristic metrics for head tracking, in accordance with an embodiment of the present specification.

Referring back to FIG. 3, head tracking data 316 may be another form of efferent data 306 source. Head tracking data 316 may track user's 302 head orientation and physical position from either video tracking (VET or otherwise) or position sensors located on HMDs, headsets, or other worn devices. In addition to tracking user's 302 head, their body may be tracked. The position of users' 302 bodies and parts thereof may be recorded, likely from video based motion capture or accelerometers in wearable devices. This position data would commonly be used to encode manual response data (coming from finger, hand or arm tracking) and/or head orientation relative to the environment to aid in eye gaze measurements and updating of the user's visual environment. Head position data may also be used to model the effect of head shadow on sounds coming from the environment. FIG. 10 illustrates characteristic metrics 1000 for head tracking, which may include head orientation 1002 and/or physical position 1004, in accordance with an embodiment of the present specification.

Sample questions concerning head tracking metrics that may be answered over a period of time may include: where are the users looking most (potentially in response to repeating events), how fast and accurate are head movements, how accurate is pursuit/tracking, is there preference for certain areas/stimuli, are users accurately coordinating head and eye movements to direct gaze and/or track objects, are head movements reduced due to the hardware, are users making many adjustments to the hardware, are users measurably fatigued by the hardware.

Head movements may be specifically important in the realms of virtual, augmented, and mixed reality, and may generally be correlated with eye movements, depending upon the task. There is large individual variability in propensity for head movements accompanying eye movements. During tasks like reading, head movement can account for 5% to 40% of shifting gaze (combined with eye movements). The degree to which a user normally moves their head may prove a key indicator of susceptibility to sickness from mismatch of visual and vestibular sensation.

It is likely that saccadic and pursuit head movements may be qualitatively different in those two modalities. For example, a mismatch may be less jarring if users follow an object from body front, 90 degrees to the right, to body side using a pursuit movement as opposed to freely directing gaze from forward to the right. If the velocity of a pursuit object is relatively steady then the mismatch would be imperceptible through most of the motion.

Referring back to FIG. 3, a user's 302 vocal responses may also be tracked via microphone. Speech recognition algorithms would extract semantic meaning from recorded sound and mark the time of responses (potentially of individual words or syllables). In less sophisticated scenarios the intensity of vocal responses may be sufficient to mark the time of response. In embodiments, voice and speech data is correlated with several other forms of data such as and not limited to head tracking, eye-tracking, manual inputs, in order to determine levels of perception.

Electrophysiology/Autonomous Recording

Electrophysiological and autonomic measures fall largely outside the realm of conscious influence and, therefore, performance. These measures pertain largely to states of arousal and may therefore be used to guide stimulus selection. Recounted for convenience here, the measures of interest would come from electroencephalography (EEG—specifically the activity of various frequency bands associated with arousal states), galvanic skin response (GSR—also associated with arousal and reaction to emotional stimuli), heart rate, respiratory rate, blood oxygenation, and potentially measures of skeletal muscle responses.

Reference is again made to WO2015003097A1 titled "A Non-Invasive Method for Assessing and Monitoring Brain". In an example, brain wave activity is assessed by performing an active brain wave test. The active brain wave test may be conducted using EEG (electroencephalography) equipment and following methods known in the art. The active brain wave test may be performed while the individual is presented with a variety of visual stimuli. In some embodiments, the active brain wave test is conducted while presenting a standardized set of visual stimuli that is appropriate for assessing active brain wave activity. In some embodiments, the active brain wave test may be conducted multiple times, using the same or different visual stimuli, to obtain an average result. The results of the active brain wave test may comprise, for example, temporal and spatial measurements of alpha waves, beta waves, delta waves, and theta waves. In some embodiments, the results of the active brain wave test may comprise a ratio of two types of brain waves; for example, the results may include a ratio of alpha/theta waves.

Similarly, a passive brain wave test may be performed. The passive brain wave test may be conducted using EEG (electroencephalography) equipment to record brain wave data while the individual has closed eyes; i.e., in the absence of visual stimuli. The results of the passive wave brain wave test may comprise, for example, temporal and spatial measurements of alpha waves, beta waves, delta waves, and theta waves, for example. In some embodiments, the results of the passive brain wave test may comprise a ratio of two types of brain waves; for example, the results may include a ratio of alpha/theta waves. In some embodiments, the passive brain wave test may be conducted multiple times to obtain an average result.

When possible, and reliant upon precise timing information for both electric potentials and stimulus displays/speakers, time-averaged responses can be generated from repeated trials. Characteristic waveforms associated with visual or auditory processing (Event Related Potentials, ERP) can be measured and manipulated in various ways. As these do not require volitional behavior from users they represent a lower-level, arguably more pure measure of perception.

Referring back to FIG. 3, electrophysiological data 318 may be yet another efferent data source 306, which may generally be available in the form of voltage potentials recorded at a rate on the order of kHz. This may include any and all measurements of voltage potentials among electrodes placed on the skin or other exposed tissue (notably the cornea of the eye). Most use cases would presumably involve noninvasive recording, however opportunities may arise to analyze data from implanted electrodes placed for other medically valid purposes. Data may generally be collected at rates in the hundreds or thousands of samples per second. Analyses may focus on either time-locked averages of responses to stimulus events to generate waveforms or on various filtered representations of the data over time from which various states of activity may be inferred. For example, Electroencephalogram (EEG) may be used to gather electrode recording from the scalp/head, to reveal electrical activity of the brain and other neural activity. Recording may focus on areas of primary sensory processing, secondary and later sensory processing, cognitive processing or response generation (motor processing, language processing). An Electrooculogram (EOG) may be utilized to gather electrode recording from near the eye to measure changes in field potential due to relative eye position (gaze direction) and can also measure properties of retinal function and muscle activity. EOG may provide a low spatial resolution substitute for video eye tracking. An Electroretinogram (ERG) may be used to gather electrode recording from the cornea (minimally invasive) to capture neural activity from the retina. Correlation with chromatic and spatial properties of stimuli may allow for the characterization of responses from different cone types and locations on the retina (this is also the case with visual evoked potentials recorded via EEG). An Electrocardiogram (ECG) may be used to gather neuromuscular activity corresponding to cardiac function and provide measures of autonomic states, potentially in response to stimuli. Measurement of neuromuscular potentials may involve electrodes placed anywhere to record neuromuscular activity from skeletal muscle flex and/or movement of body and limb (including electromyogram, or EMG). Measurement of Galvanic Skin Response (GSR) may involve electrodes that can measure potential differences across the skin which are subject to conductance variations due to sweat and other state changes of the skin. These changes are involuntary and may reveal autonomic responses to stimuli or scenarios.

Figure 11:
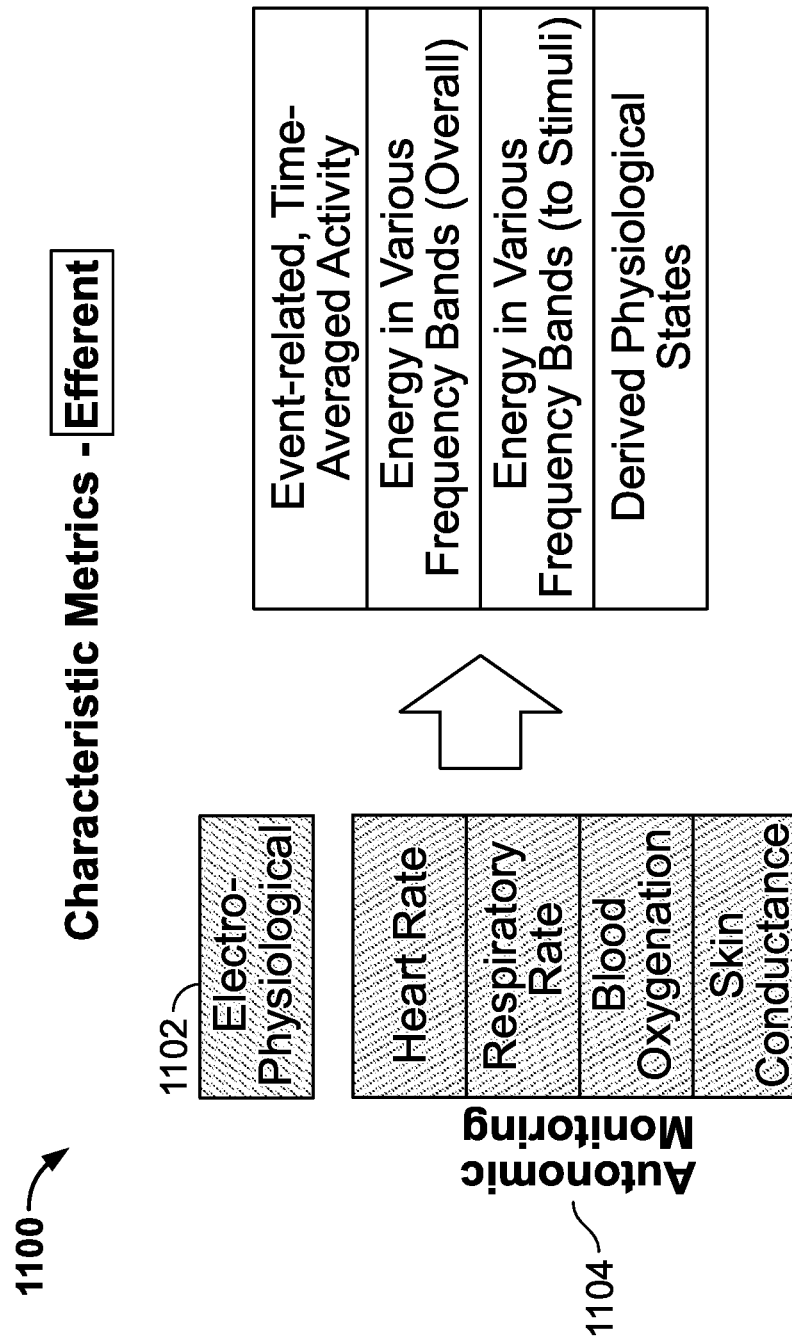
FIG. 11 illustrates characteristic metrics for electrophysiological and autonomic monitoring data, in accordance with an embodiment of the present specification.

Another source of efferent data 306 may be autonomic monitoring data 320, including information about heart rate, respiratory rate, blood oxygenation, skin conductance, and other autonomic (unconscious) response data from user 302 in forms similar to those for electrophysiological data 318. Pressure transducers or other sensors may relay data about respiration rate. Pulse oximetry can measure blood oxygenation. Pressure transducers or other sensors can also measure blood pressure. Any and all unconscious, autonomic measures may reveal responses to stimuli or general states for categorization of other data. FIG. 11 illustrates characteristic metrics 1100 for electrophysiological monitoring data 1102 and autonomic monitoring data 1104, in accordance with an embodiment of the present specification.

Sample questions concerning electrophysiological metrics 1102 and autonomic metrics 1104 that may be answered over a period of time may include: what are the characteristics of time-averaged responses to events, how do various frequency bands or other derived states change over time or in response to stimuli.

Sensors for collecting data may be a part of hardware 106, described above in context of FIG. 1. Some sensors can be integrated into an HMD (for example, sensors for electroencephalography, electrooculography, electroretinography, cardiovascular monitoring, galvanic skin response, and others). Referring back to FIG. 3, some data may require sensors elsewhere on the body of user 302. Non-contact sensors (even video) may be able to monitor some electrophysiological data 318 and autonomic monitoring data 320. In embodiments, these sensors could be smart clothing and other apparel. It may be possible to use imaging data for users, to categorize users or their present state. Functional imaging may also provide data relating to unconscious responses to stimuli. Imaging modalities include X-Ray/Computed Tomography (CT), Magnetic Resonance Imaging (MRI), Ophthalmic Imaging, Ultrasound, and Magnetoencephalography (MEG). Structural data derived from imaging may be used to localize sources of electrophysiological data (e.g. combining one or more of structural, MRI EEG, and MEG data).

Metrics may be broken into direct measures that can be inferred from these stimulus/response feature pairs, and indirect measures that can be inferred from the direct measures. It should be understood that in most cases individual occurrences of stimulus/response feature pairings may be combined statistically to estimate central tendency and variability. There is potential value in data from a single trial, from descriptive statistics derived from multiple repeated trials of a particular description and from exploring stimulus and/or response features as continuous variables for modelling and prediction.

Facial Pattern Recognition Machine Learning

The SDEP may utilize its models and predictive components in combination with a product to enable development of a customized predictive component for the product. The SDEP predictive components may be built through a collection process by which a large dataset of vision data from naturalistic or unconstrained settings from both primary and secondary sources may be curated and labeled. The dataset may include photographs, YouTube videos, Twitch, Instagram, and facial datasets that are available through secondary research, such as through the Internet. The curated and labeled data may be utilized for further engagement, and to build a custom-platform for the product.

Figure 12B:
FIG. 12B illustrates an exemplary process of image analysis of building curated data, in accordance with an embodiment of the present specification.
Figure 12A:
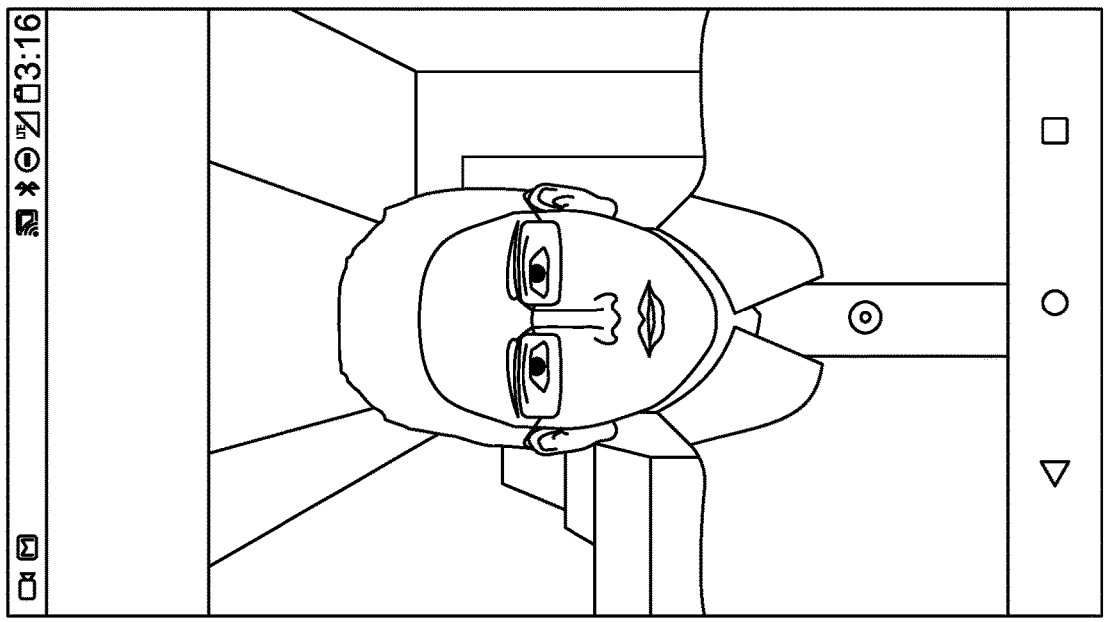
FIG. 12A illustrates an exemplary process of image analysis of building curated data, in accordance with an embodiment of the present specification.

FIGS. 12A to 12D illustrate an exemplary process of image analysis of building curated data. The illustrations describe an exemplary mobile-based version of the model. In other embodiments, the model may be executed on the cloud. FIG. 12A illustrates an exemplary image of a subject for whom a customized predictive component may be developed. FIG. 12B illustrates an image of the subject where the SDEP identifies the eyes for eye tracking, blink detection, gaze direction, and other parameters and/or facial attributes. In embodiments, the eyes are continually identified for tracking purposes through a series of images or through a video of the subject.

Figure 12D:
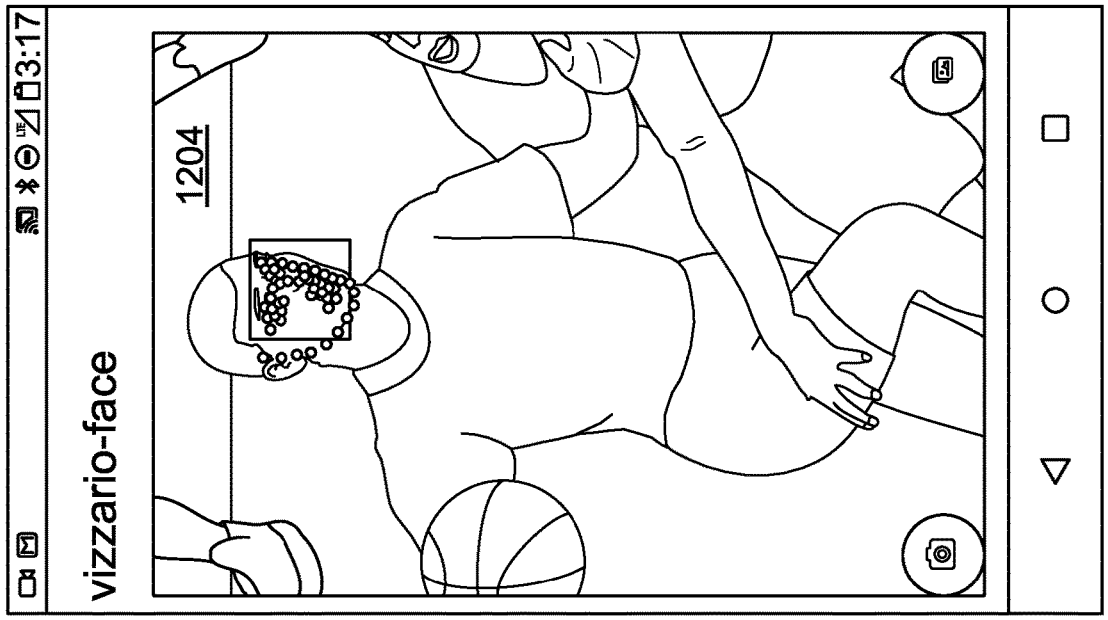
FIG. 12D illustrates an exemplary process of image analysis of building curated data, in accordance with an embodiment of the present specification.
Figure 12C:
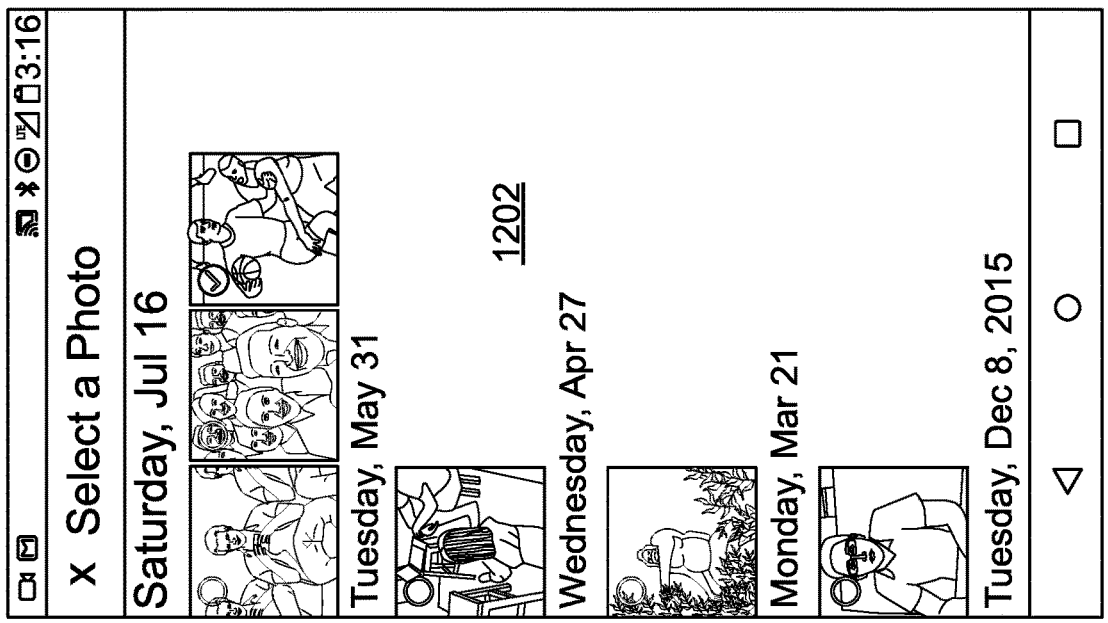
FIG. 12C illustrates an exemplary process of image analysis of building curated data, in accordance with an embodiment of the present specification.

FIG. 12C illustrates a dataset 1202 of vision data from naturalistic or unconstrained settings, which may be used for extracting face attributes in the context of eye tracking, blink, and gaze direction. In embodiments, the SDEP system is trained with a large data set 1202 under different conditions where the frames are extracted from videos. Different conditions may include among other, complex face variations, lighting conditions, occlusions, and general hardware used. In embodiments, various computer vision techniques and Deep Learning are used to train the system. Referring to FIGS. 12C and 12D, image 1204 is selected to extract its face attributes for analyzing emotions of the subject. In embodiments, images from the dataset, including image 1204, are curated and labelled.

The following steps outline an exemplary data curation and labelling process:
1. Identify desirable data sources
2. Concurrently, develop a pipeline to perform facial key point detection from video and still images. This may be achieved by leveraging facial key point localization to segment and select the ocular region from faces. Further key point features may be used to determine rotation, pitch, and lighting of images, as possible dimensions to marginalize over in downstream analysis. Facial expressions may be identified to analyze emotions. Blinks, eye movements, and microsaccades may also be identified as part of the key point detection system.
3. Scrapes of data sources may be identified and fed through the SDEP (see FIG. 2B) to obtain a normalized set of ocular region images. Final images may be segmented/cropped to include only the ocular region, such that information on pitch, rotation, and lighting is available upon return.
4. Output from the above processing may be combined with a product to label blink, coloration, strabismus, and other metrics of interest to the product.

The above-mentioned collected and labelled data may be leveraged to develop custom predictive models of the ocular region. Customized machine learning algorithms may be created to predict key parameters ranging from blink rate, fatigue, emotions, gaze direction, attention, phorias, convergence, divergence, fixation, gaze direction, pupil size, and others. In addition, multimodal approaches may leverage the SDEP in order to benefit from pixel level information in digital stimuli and jointly learn relationships with ocular response. The pixel level information may be broken down to RGB, luminance to fuse the same with existing visual modeling algorithms.

In embodiments, eye tracking parameters are extracted from eye tracking algorithms. In an embodiment, pupil position, relative to the face, provides one measure from which to classify eye movements as fixations, pursuits and saccades. In an embodiment, pupil size is also measured, independently for both eyes. In an embodiment, gaze direction is estimated from relative pupil position. Gaze position may be measured in 3D space using data from both eyes and other measures (i.e. relative position of the face and screen), including estimates of vergence. Gaze Position provides another measure from which to classify eye movements.

Figure 13A:
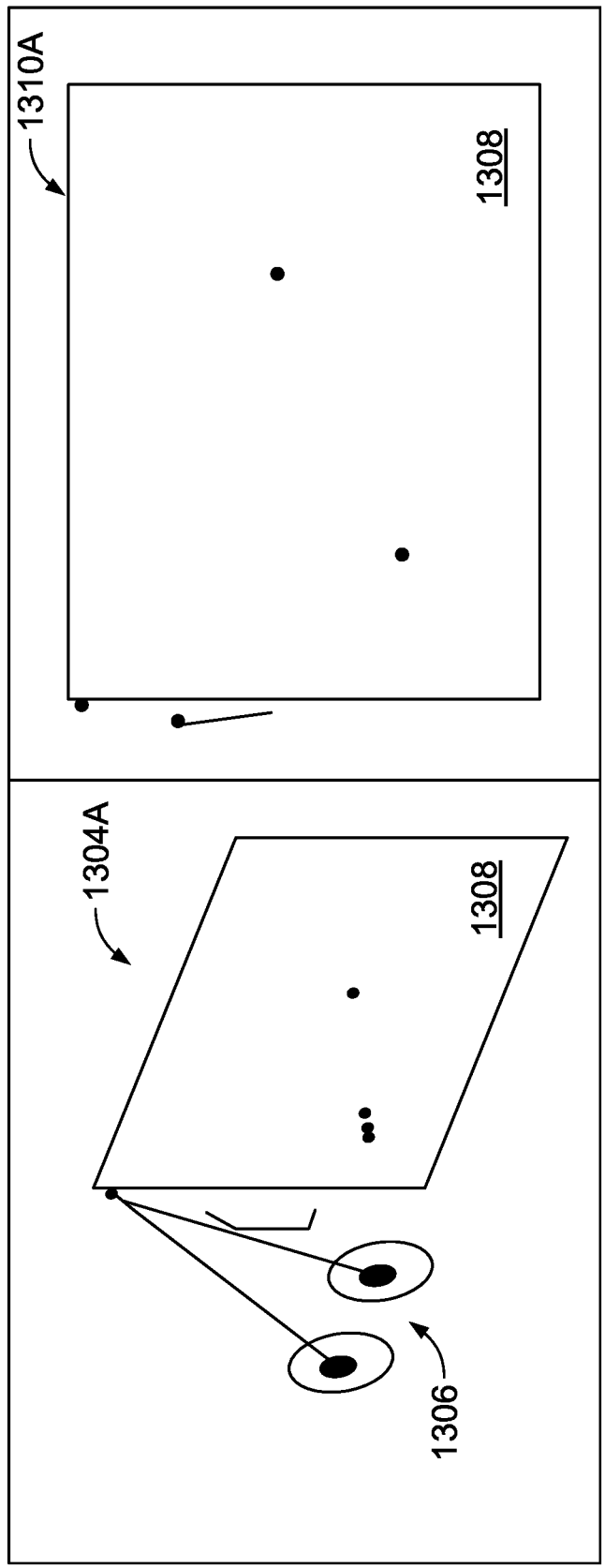
FIG. 13A illustrates pupil position and size and gaze position over time.
Figure 13B:
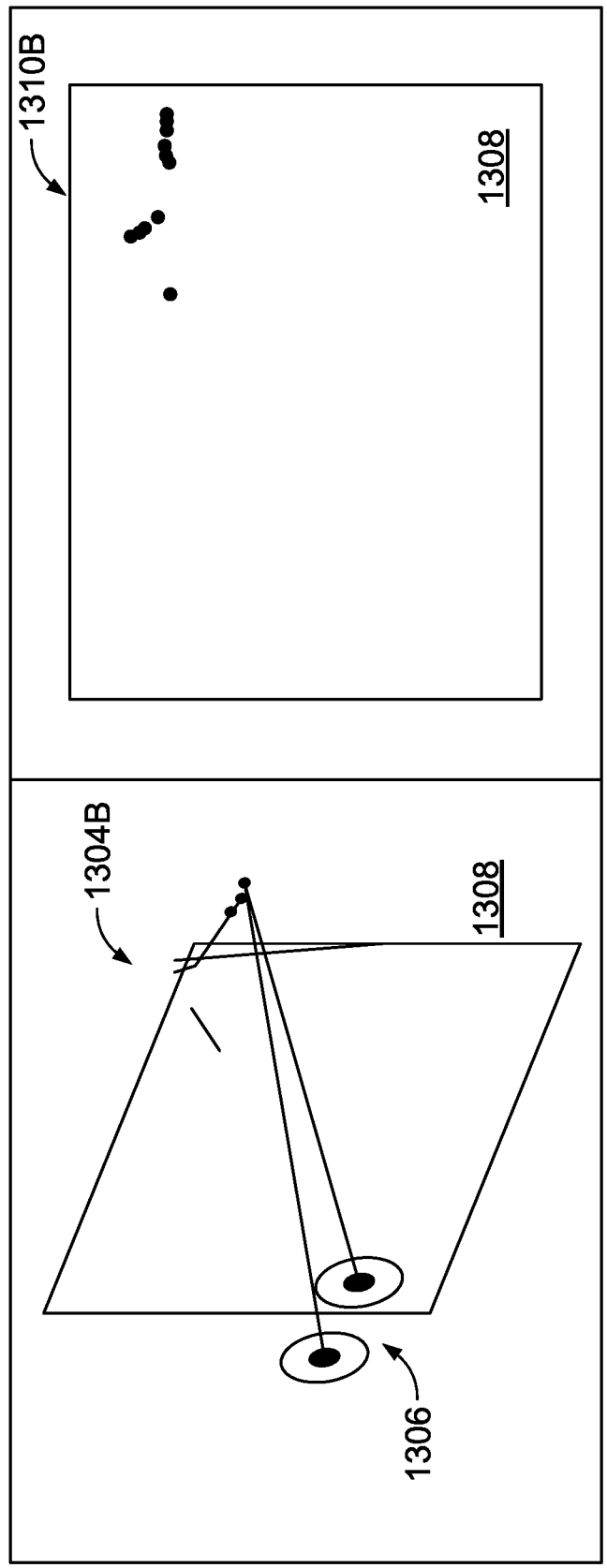
FIG. 13B illustrates pupil position and size and gaze position over time.

FIGS. 13A and 13B illustrate pupil position and size and gaze position over time. While FIG. 13A illustrates pupil position and size and gaze position in 3D 1304A and 2D 1310A, at a first time; FIG. 13B illustrates pupil position and size and gaze position in 3D 1304B and 2D 1310A, at a second time. In an embodiment the second time is later than the first time. At any given point in the image there is (up to) 1 second of data being shown, with older data shown in a different color, such as blue. The light blue square represents the display at which the observer was looking. Physical dimensions are not to scale (e.g. the viewing distance was greater than it appears to be in the left panel). The left panel 1304A and 1304B shows a 3D isometric view of space with user's eyes 1306 to the left and the display 1308 to the right.

On the left side, gaze position is shown in 3D 1304A and 1304B. A line is drawn from the surface of the observer's display 1308 to the gaze position; red indicates gaze position behind the display 1308 and green indicates gaze position in front of the display 1308. Three circles convey information about the eyes 1306:
1. The largest, dark grey outline circle represents the average position of the eyes and face, relatively fixed in space.
2. The light grey outline within represents the average pupil size and pupil position relative to the face (moves but doesn't change size).
3. The black filled circle shows relative pupil size as well as pupil position relative to the face (moves and changes size).

When the pupil information is missing it may be assumed that the eyes are closed (or otherwise obscured).

Gaze position in 3D 1304A and 1304A is shown by a black dot (connected by black lines), with gaze direction emanating from both eyes. Depth of gaze from the display is further indicated by a green (front) or red (behind) line from the display to the current gaze position.

On the right side, gaze position 1310B and 1310B is shown in 2D. Here information about the pupils is absent. Also, information classifying eye movements is added:
1. Black indicates fixation during which a grey outline grows indicating relative duration of the fixation.
2. Blue indicates pursuit.
3. Green (with connecting lines) indicates saccades with lines connecting points during the saccade.

Vision Performance Index

An important class of metrics may be those relating to performance. The performance of a user may be determined in the form of Vision Performance Index (VPI), which is described in detail subsequently in embodiments of the present specification.

Referring back to FIG. 1, in an embodiment, data collected from user 102, such as by the media system 104, may be processed to identify a Vision Performance Index (VPI) for user 102 (also referring to 240 of FIG. 2B). The VPI may indicate a level of vision performance of user 102 assessed during user's 102 interaction with the media system 104. The VPI may be used to identify a group of users for user 102 that have a similar VPI.

VPI may be measured and manipulated in various ways. In general, the goal may be to improve user's vision performance, however manipulations may also be aimed at increasing challenge (e.g. for the sake of engagement) which may, at least temporarily, decrease performance. In alternate embodiments, performance indices other than or in addition to that related to vision may be measured and manipulated. For example, other areas such as design, engagement, and the like, may be measured and manipulated through performance indices.

Referring again to FIG. 2B, an exemplary outline of a data analysis chain is illustrated. The data analysis begins at the lowest level at 232 where data level may not be simplified further. At 232, parameters of a single stimulus can be used for multiple measures based on different independent variables, which correspond to direct features of a stimulus. Parameters of a single response can be used for multiple measures based on different dependent variables. At 234 independent and dependent variables may be paired to extract a measure of a user's vision performance, or combined with others and fit to a model to generate measures of the user's vision performance. In embodiments, pairing may involve combining a response event to one or more stimulus events through correlation or other statistical/non-statistical methods. Individual pairs may be filtered to arrive at 236, where, for a given type of interaction, many pairs of independent and dependent variables can be used to either estimate the parameters of a model distribution or estimate descriptive statistics. In embodiments, a model distribution is an expectation of how often a measure will be a specific value. In some instances a normal distribution, which has the classic shape of a 'Bell curve', may be used. Once the process of descriptive statistics or model fitting is completed, at 238, an individual estimate of a physical measure of a property of user's vision may be generated. The individual user estimate may be based on a single interaction or a summary measure from multiple interactions. The measures of at least one physical property may be normalized to contribute to sub-components of VPI, at 240. At 242, multiple VPI sub-components scores may be combined (for example, averaged) to generate component scores. In embodiments, component scores may be further combined to generate overall VPI. VPI, its subcomponents, and components are discussed in greater detail in subsequent sections of the present specification.

In embodiments, measures of vision performance may be presented as a normalized "score" with relative, but not absolute, meaning, to the users. This is also illustrated at 240 and 242 in context of FIG. 2B. Users may be able to gauge their level of performance against the general population, or specific subsets thereof. Due to the presumed high degree of measurement noise associated with data recording from non-specialized hardware (i.e. mobile devices used outside of a controlled experimental setting), precise measures of efferent phenomena (e.g. pupil size, gaze direction, blink detection) and afferent parameters (e.g. display chromoluminance, viewing distance, audio intensity) are unavailable. It may therefore be required to rely on estimates of central tendency (i.e. mean) and variability (i.e. standard deviation)

from the accumulated data of all users to define "typical" ranges for each measure and to set reasonable goals for increasing or decreasing those measures.

Scores may be normalized independently for each type of measure, for each of a variety of types of tasks and generally for each unique scenario or context. This may enable easy comparison and averaging across measures taken in different units, to different stimuli, and from different kinds of user responses. Additionally, for any and all scores, performance may be categorized as being marginally or significantly above or below average. Set descriptive criteria may be decided based on percentiles (assuming a given measure will be distributed normally among the general population). The examples in the following sections use 10% and 90%, however the percentiles may be arbitrarily chosen and can be modified for specific contexts. It may be assumed that 10% of users' scores will fall in the bottom or top 10% of scores, and therefore be 'abnormally' low or high, respectively.

In an embodiment, VPI may be a combination of one or more of the following parameters and sub-parameters, which may be both afferent and efferent in nature. In some embodiments, the VPI may be a function of psychometric data, without efferent data. Direct measures generally relate a single response feature to a single stimulus feature. Whenever possible a psychometric function may be built up from the pattern of responses (average response, probability of response or proportion of a category of responses) as the stimulus feature value changes. Direct measure may include the following: detection, discrimination, response time, and/ or error.

Indirect measures may be the higher level interpretations of the direct measures and/or combinations of direct measures. These may also generally include descriptions of direct measures within or across specific contexts and the interactions among variables. Indirect measures may include the following: multi-tracking, fatigue/endurance, adaptation/learning, preference, memory, and/or states.

In embodiments, other vision-related parameters may be used to calculate the VPI, and may include, but are not limited to field of view (F), accuracy (A), multi-tracking (M), endurance (E), and/or detection/discrimination (D), together abbreviated as FAMED, all described in greater detail below.

Field of View (F)

Referring back to FIG. 1, the Field of View (F) may be described as the extent of visual world seen by user 102 at any given moment. Central vision represents a central part of the field of view of user 102, where user 102 has the greatest acuity which is important for things like reading. Peripheral Vision is the external part of the field of view of user 102, which is important for guiding future behavior and catching important events outside of user's 102 focus.

Field of View measures the relative performance of users when interacting with stimuli that are in their Central or Peripheral fields of view based on measures of Accuracy and Detection. It is assumed that performance should generally be worse in the periphery due to decreased sensitivity to most stimulus features as visual eccentricity increases. The ratio of performance with Central and Peripheral stimuli will have some mean and standard deviation among the general population; as with other measures, the normalized scores will be used to determine if users have abnormally low or high Field of View ability.

If a user's Field of View score is abnormally low it may be improved by increasing the Accuracy and Detection scores for stimuli presented in the periphery. This generally would entail increasing consistency of timing and position, increasing chromaticity and luminance differences (between and within objects), increasing the size of objects and slowing any moving targets when presented in the periphery.

Accuracy (A)

Referring back to FIG. 1, accuracy (A) may be a combination of making the right choices and being precise in actions performed by user 102. Measures of accuracy may be divided into two subcomponents: Reaction and Targeting. Reaction relates to the time it takes to process and act upon incoming information. Reaction may refer to ability of the user 102 to make speedy responses during the media experience. Reaction may be measured as the span of time between the point when enough information is available in the stimulus to make a decision (i.e. the appearance of a stimulus) and the time when the user's response is recorded. For a speeded response this will usually be less than one second.

If a user's Reaction is abnormally slow (abnormally low score) it may be that the task is too difficult and requires modification of stimulus parameters discussed later in the context of Targeting and Detection. In an embodiment, a model distribution for any given measure (for example, a log-normal distribution for reaction times) is estimated. A cut-off may be determined from the estimate, above which 5% (or any other percentage) slowest time spans are found. Any incoming measure of reaction time that is equal or greater to the cut-off is considered 'slow' (or 'significantly slow'). However, if reaction alone is abnormally low, when other scores are normal, it may be a sign of poor engagement with the task or a distraction. It may be helpful to reduce the number of items presented simultaneously or add additional, congruent cues to hold attention (e.g. add a sound to accompany the appearance of visual stimuli). If the user is required to respond to the location of a moving object, it may be that they require longer to estimate trajectories and plan an intercepting response; slowing of the target may improve reaction.

Response Time may be important for detection related measures, but is relevant to any response to a stimulus. Response time is generally the time span between a stimulus event and the response to that event. Response time may be used to measure the time necessary for the brain to process information. As an example, the appearance of a pattern on a display may lead to a certain pattern of responding from the retina measurable by ERG. At some point after the stimulus processing is evident from an averaged ERG waveform, the processing of that same stimulus will become evident in an average visual evoked potential (VEP) waveform recorded from the back of the head. At some point after that the average time to a button press response from the user indicates that the stimulus was fully processed to the point of generating a motor response. Though multiple timestamps may be generated by stimulus and response events, the response time should generally be taken as the time between the earliest detectable change in the stimulus necessary to choose the appropriate response to the earliest indication that a response has been chosen. For example, if an object begins moving in a straight line towards some key point on the display, that initial bit of motion in a particular direction may be enough for the user to know where the object will end up. They need not wait for it to get there. Likewise the initiation of moving of the mouse cursor (or any other gesture acceptable in a VR/AR/MxR environment) towards a target to be clicked may indicate that a response has been chosen, well before the click event actually occurs.

In embodiments, other changes in patterns of responding, including improvements, decrements and general shifts, may occur as the result of perceptual adaptation, perceptual learning and training (higher order learning). Considering adaptation and learning by the user may account for any variability in responses that can be explained, and thereby reduce measures of statistical noise and improve inferential power.

Patterns in responding, and changes thereof, may also be related to high order processes within the system. Users have an occasional tendency to change their minds about how they perform a task while they're doing it. Therefore, in embodiments, every choice made by users is analyzed for preferences, regardless of whether it informs models of visual processing.

In embodiments, responses are used by the system to measure recall or recognition by a user. Recall is the accurate generation of information previously recorded. Recognition is the correct differentiation between information previously recorded and new information.

Derived from measures over time and in specific contexts, measures of memory recall and recognition and memory capacity can be made. These may generally fall under the performance category and users may improve memory performance with targeted practice. Recall and recognition are often improved by semantic similarity among stimuli. Memory span may, likewise, be improved by learning to associate items with one another. The span of time over which items must be remembered may also be manipulated to alter performance on memory tasks. Distracting tasks, or lack thereof, during the retention span may also heavily influence performance.

For long term memory there may be exercises to enhance storage and retrieval, both of specific items and more generally. It may also be possible to derive measures associated with muscle memory within the context of certain physical interactions. Perceptual adaptation and perceptual learning are also candidates for measurement and manipulation.

Targeting relates to measures of temporal and positional precision in the user's actions. Referring back to FIG. 1, targeting may relate to the precision of the responses of user 102 relative to the position of objects in the VE. Targeting is measured as the error between the user's responses and an optimal value, in relation to stimuli. The response could be a click, touch, gesture, eye movement, pupil response, blink, head movement, body/limb movement, or any other. If the user is expected to respond precisely in time with some event (as opposed to acting in response to that event, leading to a Reaction measure), they may respond too early or too late. The variability in the precision of their response yields a Targeting time error measure (usually on the order of one second or less). Additionally the position of the user's responses may have either a consistent bias (mean error) and/or level of variability (standard deviation of error) measured in pixels on the screen or some other physical unit of distance.

In embodiments, the system analyzes data related to user errors, including incorrect choices and deviations made by the user from the ideal or an optimum response. Most commonly these may be misidentification of stimuli, responding at inappropriate times (false positive responses), failing to respond at appropriate times (false negatives) and inaccuracy of timing or position of responses. Variability in responses or measures of response features may also be indications of error or general inaccuracy or inconsistency.

If a user's targeting score is abnormally low it may be that targets are too small or variability of location is too great. For timing of responses, more consistent timing of events makes synchronizing responses easier. This may be in the form of a recurring rhythm or a cue that occurs at some fixed time before the target event. For position, errors can be reduced by restricting the possible locations of targets or, in the case of moving targets, using slower speeds. Particularly for touch interfaces or other contexts where responses may themselves obscure the target (i.e. finger covering the display), making the target larger may improve targeting scores.

Multi-Tracking (M)

Multi-tracking (M) may generally refer to instances in which users are making multiple, simultaneous responses and/or are responding to multiple, simultaneous stimuli. They also include cases where users are performing more than one concurrent task, and responses to stimulus events that occur in the periphery (presumably while attention is focused elsewhere). Combination measures of peripheral detection (detection as a function of eccentricity) and other performance measures in the context of divided attention may be included.

Multi-tracking (M) may represent the ability of the user to sense multiple objects at the same time. Divided attention tasks may require user to act upon multiple things happening at once. Multi-Tracking measures the relative performance of users when interacting with stimuli that are presented in the context of Focused or Divided Attention. With focused attention, users generally need to pay attention to one part of a scene or a limited number of objects or features. In situations requiring divided attention, users must monitor multiple areas and run the risk of missing important events despite vigilance. As with Field of View, measures of Accuracy and Detection are used to determine a user's performance in the different Multi-Tracking contexts.

If a user's Multi-Tracking score is abnormally low it may indicate that they are performing poorly with tasks requiring Divided Attention, or exceptionally well with tasks requiring Focused Attention. Therefore, making Divided Attention tasks easier or Focused Attention tasks more difficult may improve the Multi-Tracking score. In the context of Divided Attention, reducing the perceptual load by decreasing the number of objects or areas the user needs to monitor may help. Increasing durations (object persistence) and slowing speeds in Divided Attention may also improve scores.

Fatigue/Endurance (E)

Performance measures may become worse over time due to fatigue. This may become evident in reductions in sensitivity (detection), correct discrimination, increase in response time and worsening rates or magnitudes of error. The rate of fatigue (change over time) and magnitude of fatigue (maximum reduction in performance measures) may be tracked for any and all measures. The delay before fatigue onset, as well as rates of recovery with rest or change in activity, may characterize endurance.

Endurance (E) may be related to the ability of user to maintain a high level of performance over time. Endurance measures relate to trends of Accuracy and Detection scores over time. Two measures for Endurance are Fatigue and Recovery.

Fatigue is a measure of how much performance decreases within a span of time. Fatigue is the point at which the performance of user may begin to decline, with measures of a rate of decline and how poor the performance gets. The basic measure of fatigue may be based on the ratio of scores in the latter half of a span of time compared to the earlier half. We assume that, given a long enough span of time, scores will decrease over time as users become fatigued and therefore the ratio will be less than 1. A ratio of 1 may indicate no fatigue, and a ratio greater than 1 may suggest learning or training effects are improving performance along with a lack of fatigue. If a user's Fatigue score is abnormally low then they may want to decrease the length of uninterrupted time in which they engage with the task. Taking longer and/or more frequent breaks may improve Fatigue scores. Generally decreasing the difficulty of tasks should help as well.

Recovery is a measure of performance returning to baseline levels between spans of time, with an assumed period of rest in the intervening interval. Recovery may relate to using breaks provided to user effectively to return to optimum performance. The basic measure of recovery currently implemented is to compare the ratio of scores in the latter half of the first of two spans of time to the scores in the earlier half of the second span of time. The spans of time may be chosen with the intention of the user having had a bit of rest between them. We assume that, given long enough spans of time to ensure some fatigue is occurring, scores will be lower before a break compared to after and therefore the ratio will be less than 1. A ratio of 1 indicates no effect of taking a break, and a ratio greater than 1 may indicate a decrease in engagement after the break or the presence of fatigue across, and despite, the break.

If a user's Recovery score is abnormally low, they may want to take longer breaks. It's possible they are not experiencing sufficient fatigue in order for there to be measurable recovery. Challenging the user to engage for longer, uninterrupted spans of time may improve recovery scores. Likewise an increase in task difficulty may result in greater fatigue and more room for recovery.

Detection/Discrimination (D)

Detection/Discrimination (D) may refer to the ability of the user to detect the presence of an object, or to differentiate among multiple objects. This parameter may depend on the sensitivity of user to various attributes of the object. Whenever a response event signals awareness of a stimulus event it may be determined that a user detected that stimulus. Unconscious processing, perhaps not quite to the level of awareness, may also be revealed from electrophysiological or other responses. Detection can be revealed by responding to the location of the stimulus or by a category of response that is congruent with the presence of that stimulus (e.g. correctly identifying some physical aspect of the stimulus). The magnitude of a stimulus feature parameter/value necessary for detection may define the user's detection threshold. Any feature of a stimulus may be presumed to be used for detection, however it will only be possible to exclusively attribute detection to a feature if that feature was the only substantial defining characteristic of the stimulus or if that stimulus feature appears in a great variety of stimuli to which users have made responses.

Whenever users correctly identify a stimulus feature parameter/value or make some choice among multiple alternatives based on one or more stimulus features that interaction may contribute towards a measure of discrimination. In many cases the measure of interest may be how different two things need to be before a user can tell they are different (discrimination threshold). Discrimination measures may indicate a threshold for sensitivity to certain features, but they may also be used to identify category boundaries (e.g. the border between two named colors). Unlike detection measures, discrimination measures need not necessarily depend upon responses being correct/incorrect. Discrimination measures may indicate subjective experience instead of ability.

Measures of Detection/Discrimination may be divided into three subcomponents: measures related to detecting and/or discriminating Color (chromoluminance), Contrast (chromoluminant contrast), and Acuity measures based on the smallest features of a stimulus. These afferent properties, in combination with efferent measures from manual or vocal responses, eye tracking measures (initiation of pro-saccade, decrease in anti-saccade, sustained fixation and decreased blink response), gaze direction, pupil size, blinks, head tracking measures, electrophysiological and/or autonomously recorded measures, measures from facial pattern recognition and machine learning, and others, as discussed above, are used to determine sensitivity. All measures may be based on a user's ability to detect faintly visible stimuli or discriminate nearly identical stimuli. These measures are tied to the different subcomponents based on differences (between detected objects and their surroundings or between discriminated objects) in their features. Stimulus objects can differ in more than one feature and therefore contribute to measures of more than one subcomponent at a time.

Color differences may refer specifically to differences in chromaticity and/or luminance. If a user's Color score is abnormally low, tasks can be made easier by increasing differences in color. Specific color deficiencies may lead to poor color scores for specific directions of color differences. Using a greater variety of hues will generally allow specific deficiencies to have a smaller impact and stabilize scores.

Contrast differs from Color in that contrast refers to the variability of chromaticity and/or luminance within some visually defined area, whereas measures relating to Color in this context refer to the mean chromaticity and luminance. If a user's Contrast score is abnormally low it may be improved by increasing the range of contrast that is shown. Contrast sensitivity varies with spatial frequency, and so increasing or decreasing spatial frequency (making patterns more fine or coarse, respectively) may also help. Manipulations that improve Color scores will also generally improve Contrast scores.

Acuity measures derive from the smallest features users can use to detect and discriminate stimuli. It is related to contrast in that spatial frequency is also a relevant physical feature for measures of acuity. If a user's Acuity score is abnormally low it may be that objects are generally too small and should be enlarged overall. It may also help to increase differences in size, increase contrast and decrease spatial frequency. More so with Acuity than Color or Contrast, the speed of moving stimuli can be a factor and slowing moving targets may help improve Acuity scores.

The above parameters are all based on measuring features. In embodiments, their patterns may be noted over time. Trends and patterns may enable predictive analytics and also help personalize the user experience based on detection capabilities and other VPI/FAMED capabilities of the end user.

A great many general states of being may be inferred from the direct measures discussed. States may be estimated once per session, for certain segments of time or on a continuous basis, and in response to stimulus events. These may commonly relate to rates of responding or changes in behavior. FIG. 14 provides a table containing a list of exemplary metrics for afferent and efferent sources, in accordance with some embodiments of the present specification. The table illustrates that an afferent source may result in a stimulus event and feature. The combination of afferent source, stimulus events and feature, when combined further with a response (efferent source), may indicate a response event and feature. These combinations may hint at a psychometric measure. In the last column, the table provides a description for each psychometric measure derived from the various combinations.

Figure 15:
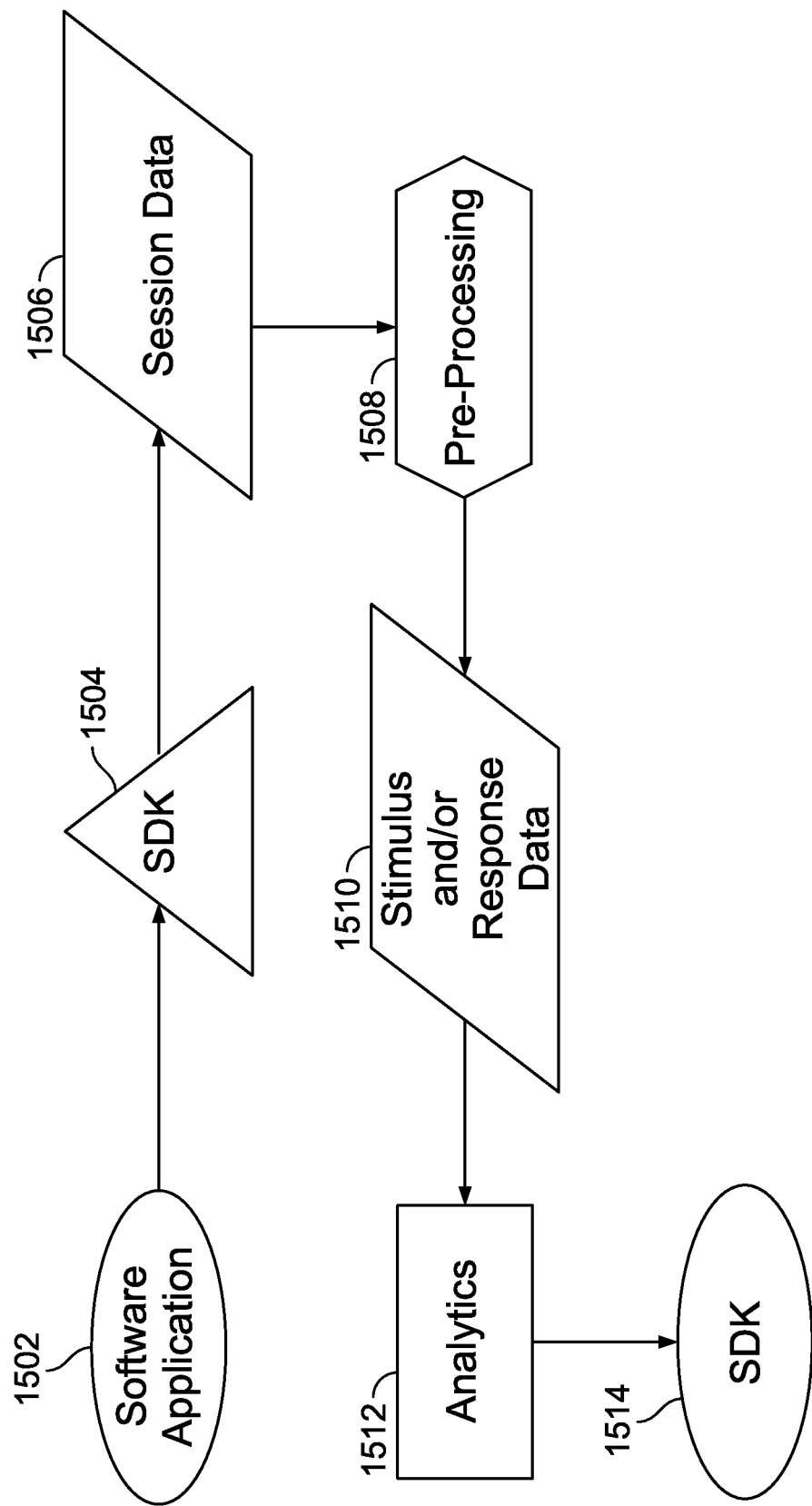
FIG. 15 is an exemplary flow chart illustrating an overview of the flow of data from a software application to the SDEP.

FIG. 15 is an exemplary flow diagram illustrating an overview of the flow of data from a software application to the SDEP. At 1502, a software application that may provide an interface to a user for interaction. The app may be designed to run on an HMD, or any other device capable of providing a VR/AR/MxR environment for user interaction. Information collected by the application software may be provided to a Software Development Kit (SDK) at 1504. The SDK works with a group of software development tools to generate analytics and data about use of the application software. At 1506 the data is provided as session data from the SDK to the SDEP. At 1508, session data is pre-processed at the SDEP, which may include organizing and sorting the data in preparation for analysis. At 1510, stimulus and response data that has been pre-processed is generated and passed further for analysis and processing. At 1512, data is analyzed and converted to performance indices or scores or other measures of perceivable information, such as VPI scores. At 1514, the analyzed data is sent back to the SDK and/or application software in order to modify, personalize, or customize the user experience. In embodiments data is passed from 1502, from application software through the chain of analysis, and back to the application software non-intrusively, in real time.

Figure 16:
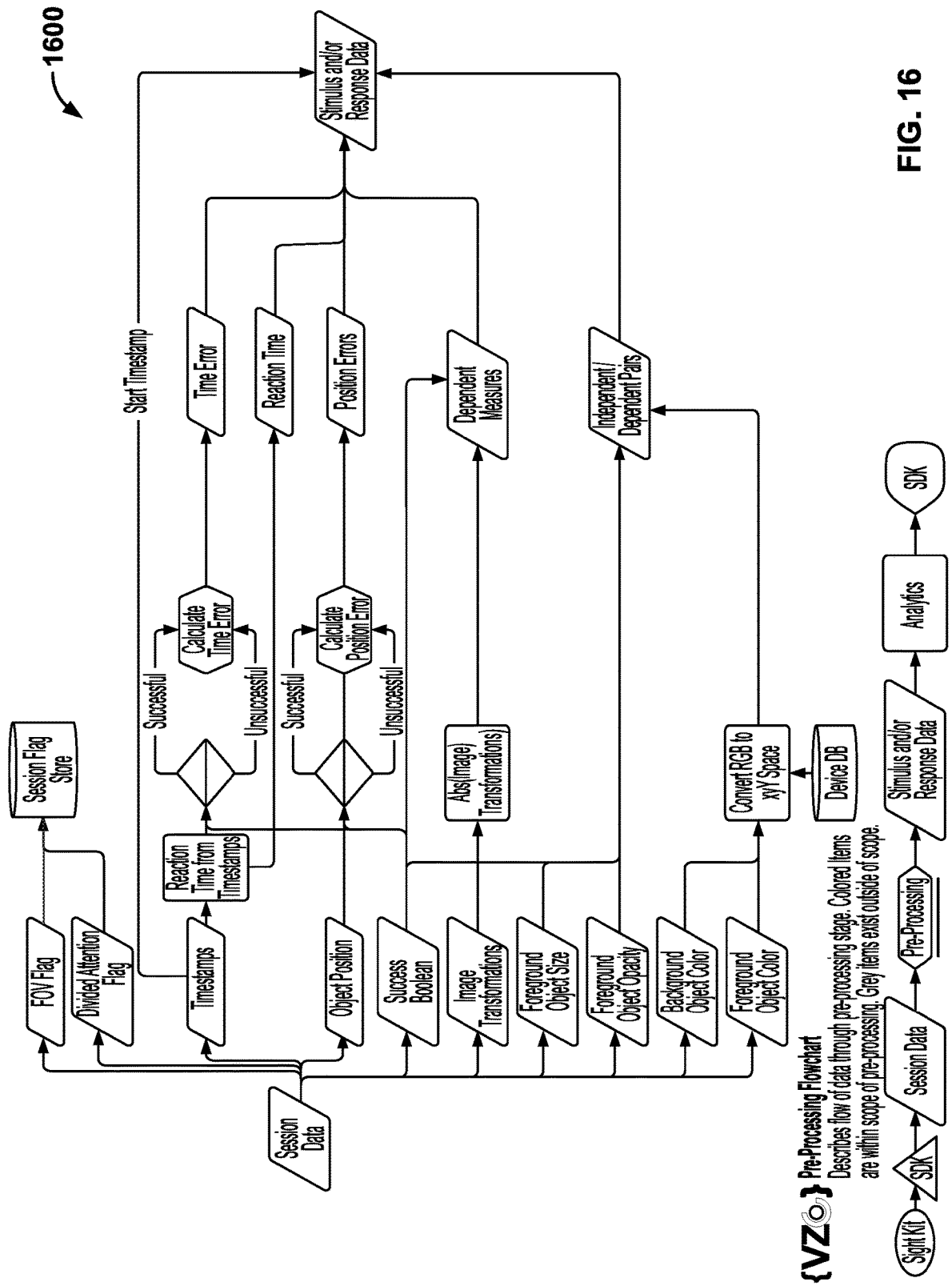
FIG. 16 is an exemplary outline of a pre-processing portion of a process flow, in accordance with an embodiment of the present specification.

FIG. 16 illustrates an exemplary outline 1600 of a pre-processing part of the process flow (1508, FIG. 15).

Figure 17:
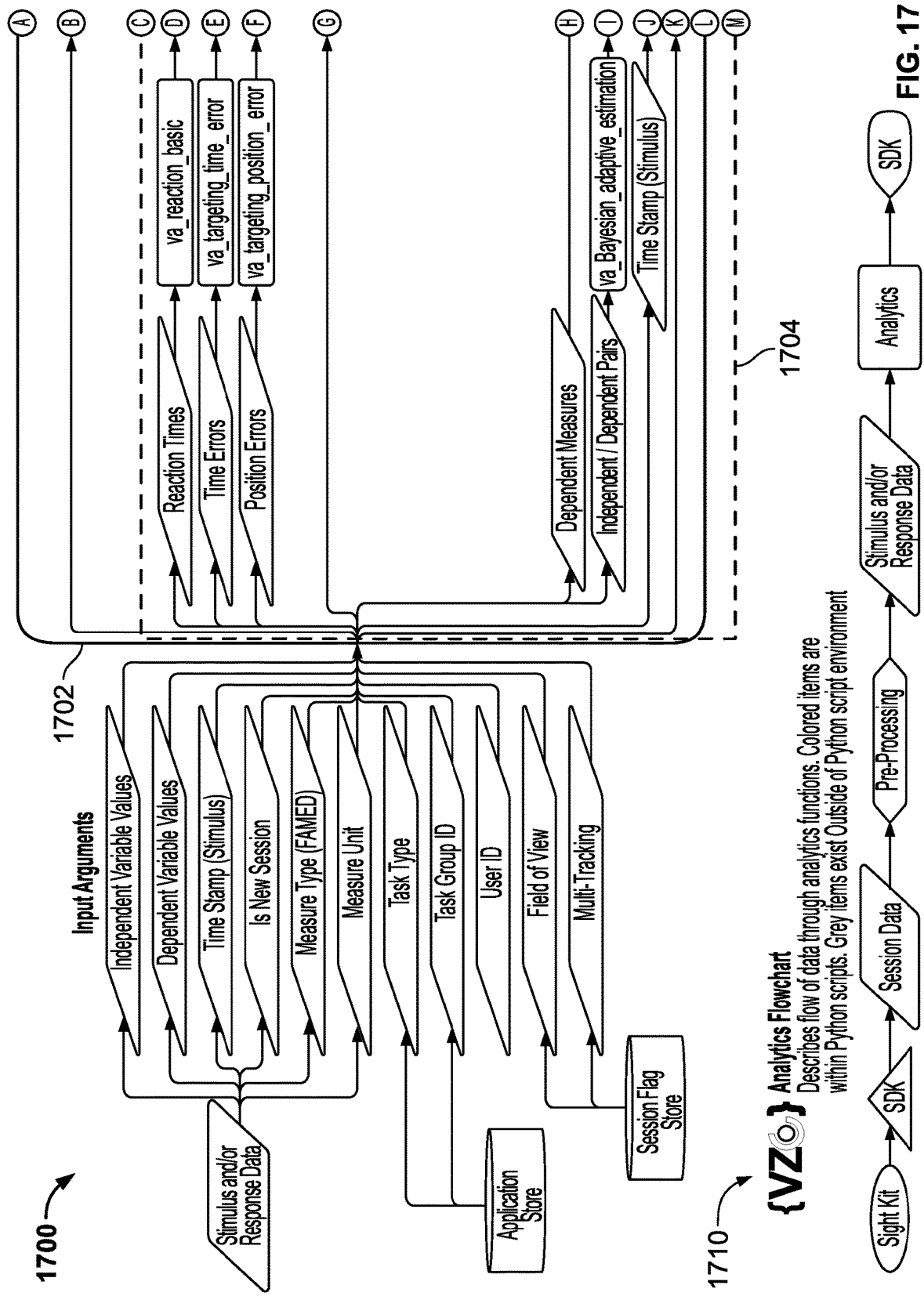
FIG. 17 is an exemplary outline of a python scripting portion of the analysis chain.
Figure 17:
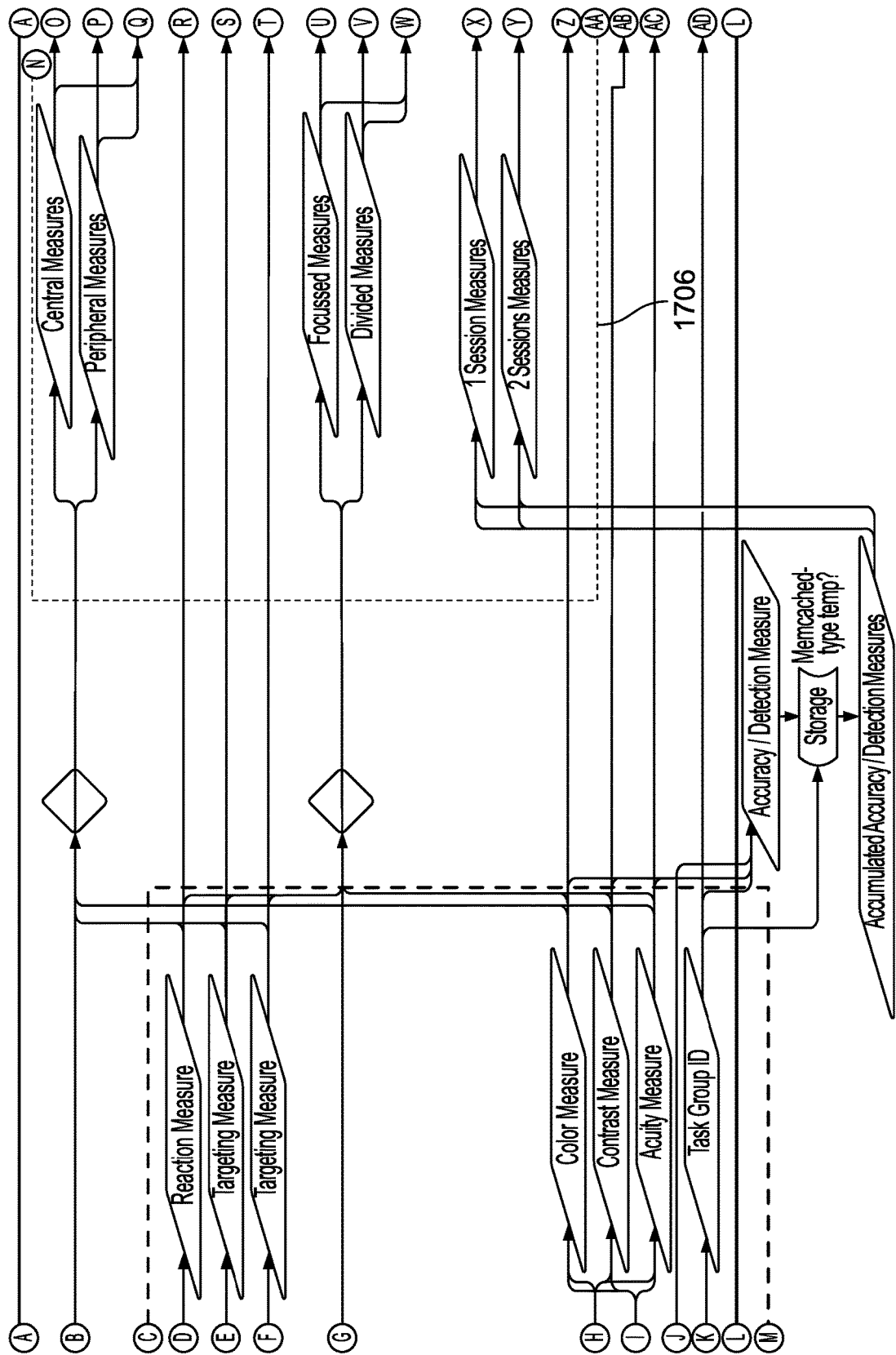
Figure 17:
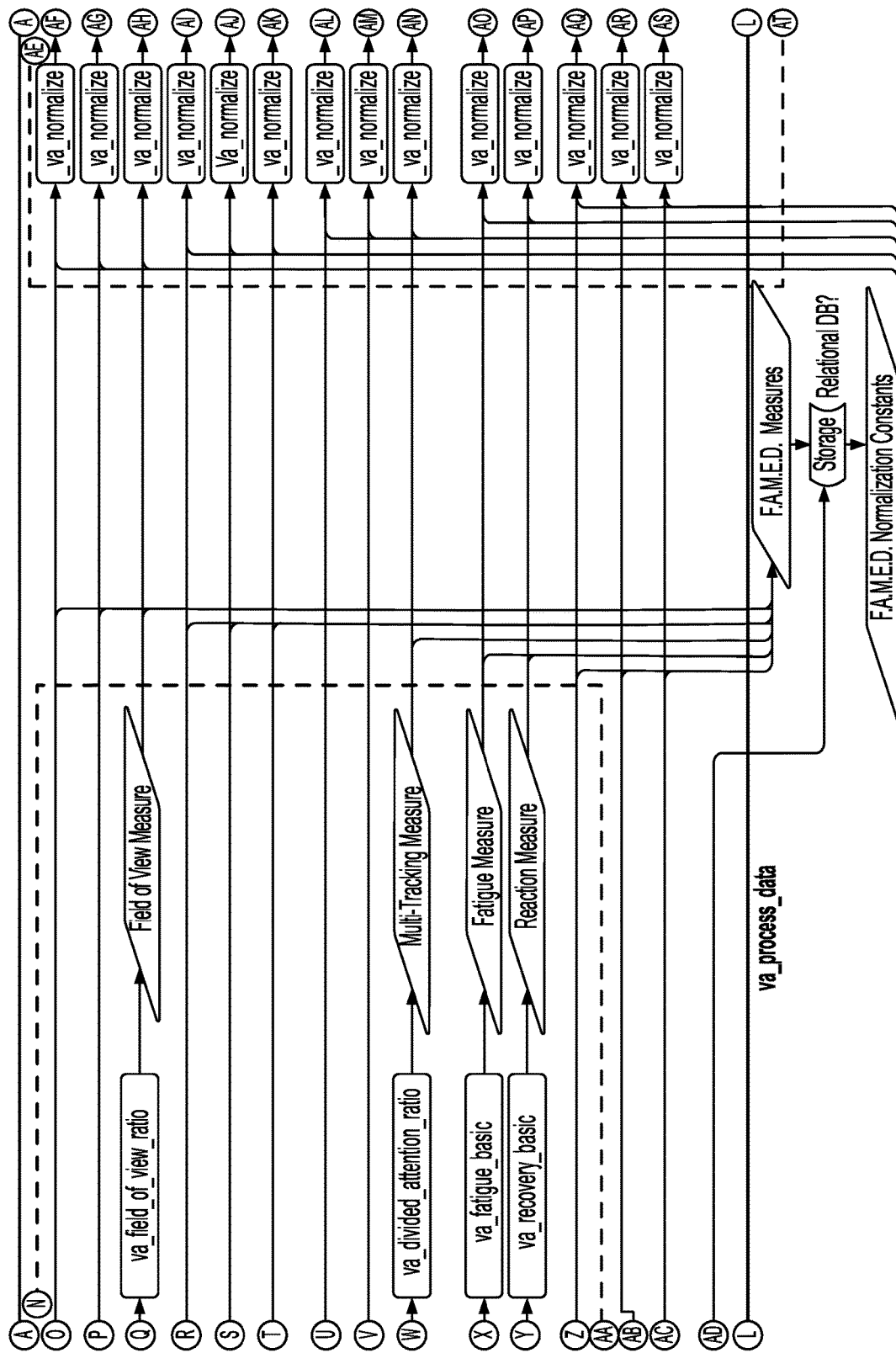
Figure 17:
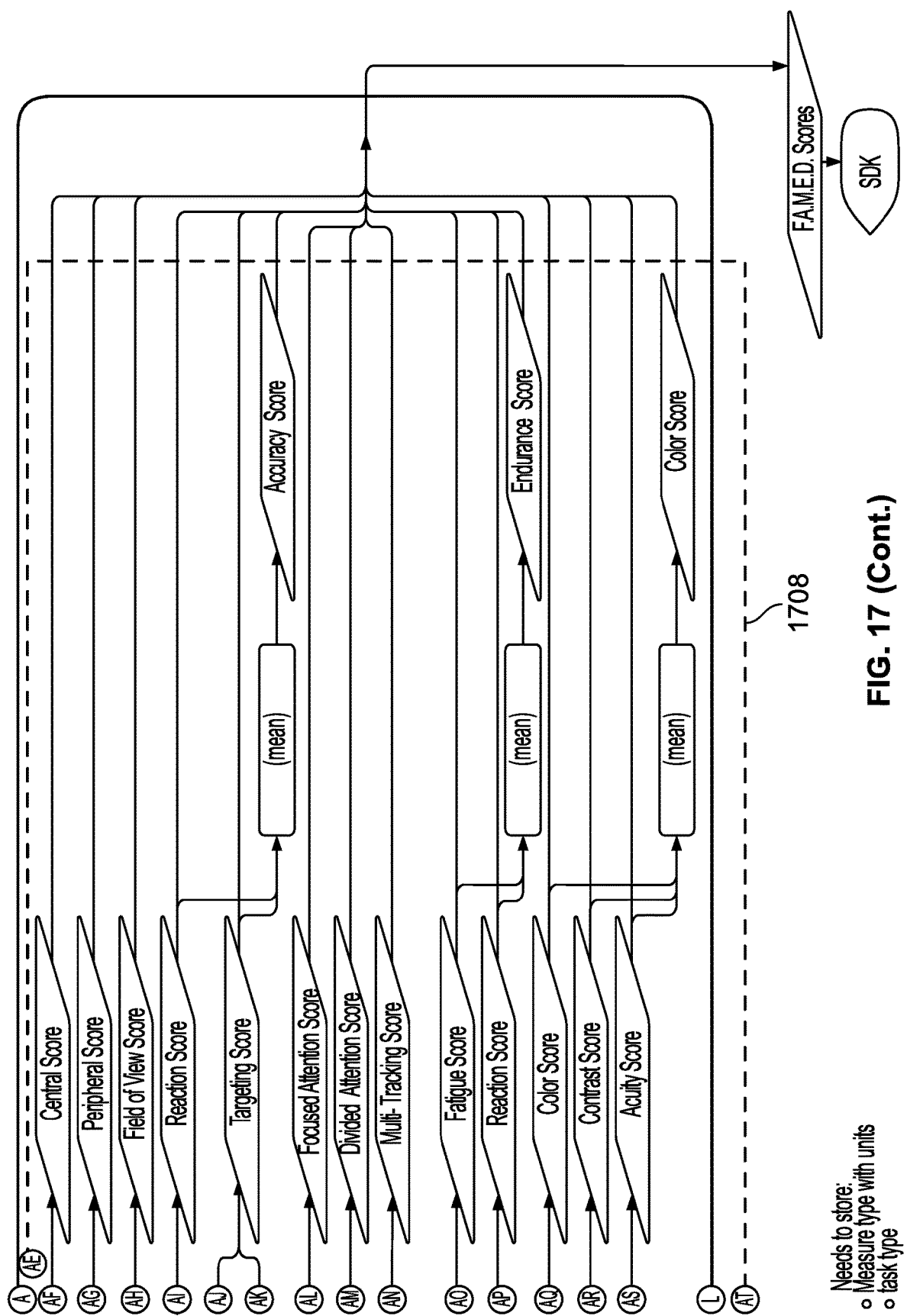

FIG. 17 is an exemplary representation 1700 of the programming language implementation of a data processing function responsible for taking in raw data (pre-processed), choosing and implementing the appropriate analysis, sending and receiving summary measures based on the analysis to temporary and long-term stores for estimates of 'endurance' measures and score normalization, respectively, and computing scores to be sent back to the application for display to the end user. In embodiments, the programming language used is Python. The figure shows application of several Python functions to FAMED data in order to derive VPI scores. The figure illustrates color-coded processes for each FAMED function. In an embodiment, FOV functions are in Red, Accuracy in Green, Multi-Tracking in Purple, Endurance in Orange, and Detection in Blue. In an embodiment, parallelograms represent variables; rounded rectangles represent functions; elements are color coded for user/session data, which are shown in yellow.

Referring to the figure, contents of a large red outline 1702 represent the processing function (va_process_data), which includes three main sections—a left section 1704, a middle section 1706 and a right section 1708. In an embodiment, left section 1704 takes in raw data and applies either Accuracy or Detection/Discrimination analysis functions to the data yielding a single measure summarizing the incoming data. That is sent to middle-level functions 1706 for measures of Field of View and Multi-Tracking as well as to an external store. That first external store, or cache, returns similar measures from the recent past to be used for measures of Endurance. The output from the middle-level functions 1706 are sent to another external store that accumulates measures in order to estimate central tendency (i.e. arithmetic mean) and variability (i.e. standard deviation) for normalization. Data from this second, external store are combined with the present measurements to be converted into Scores in the right-level section 1708. The figure also illustrates a small sub-chart 1710 in the lower left of the figure to show the place Visual Data Packages: Examples of Use Data generated by the SDEP in accordance with various embodiments of the present specification may be used in different forms. In embodiments, data output by the SDEP may be packaged differently for medical use (visual acuity, eye strain, traumatic brain injury, and sports vision performance), for athletes/sports, and others. For example, applications include the ability to track the effects of digital eye strain over a period of time or to screen for traumatic brain injury in contact sports such as football by measuring key areas of the eye-brain connection.

In embodiments, the SDEP allows for advantageously using data generated from technologies such as smart devices, wearables, eye-tracking tools, EEG systems, and virtual reality and augmented reality HMDs.

Performance indices, including VPI, may be different for different applications. In an example, detection and accuracy metrics are different for a gaming media vs. media for an advertisement. Some exemplary embodiments of a few applications are described below.

Figure 18:
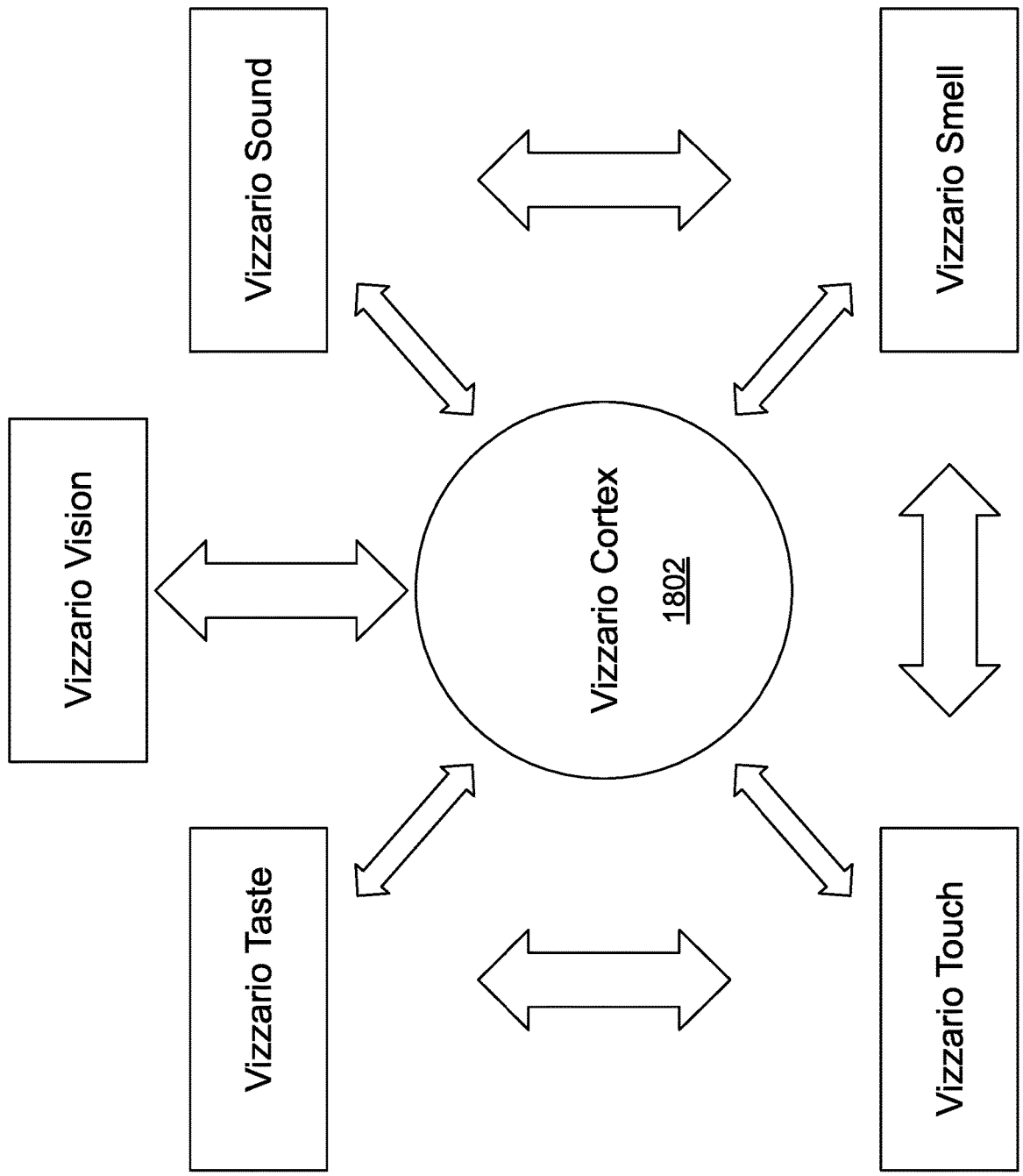
FIG. 18 illustrates an exemplary environment for implementing a central system that utilizes the SDEP to process psychometric functions and to model visual behavior and perception based on biomimicry of user interaction.

FIG. 18 illustrates an exemplary environment for implementing a central system 1802 that utilizes the SDEP to process psychometric functions and model visual behavior and perception based on biomimicry of the user interaction. In an example, as described below, a user may be presented with an interactive electronic media, similar to a game, in which they are required to 'pop' balloons that appear at different locations on a screen. In this example, system 1802 may utilize psychometric functions to measure vision psychometrics that are subsequently presented to the user as FAMED insights. Similarly, there may be other forms of interactive media that enables collection of psychometric information in relationship to visual perception and spatial orientation. FIG. 18 illustrates various sensory psychometric data interacting with system 1802 and each other to enable processing through SDEP and subsequent modeling and thereafter support artificial intelligence systems.

More specifically, the present specification describes methods, systems and software that are provided to train and develop deep learning systems in order to mimic the human sensory system. In some embodiments, the system may also train and develop deep learning systems that mimic human facial expressions. In an embodiment, a central system communicates with one or more SDEP systems, and a plurality of autonomic and somatic sensors to collect data that can be used to train learning routines.

Gaming Applications to Measure User's Vision Performance

In an embodiment, the present specification describes methods, systems and software that are provided to vision service providers in order to gather more detailed data about the function and anatomy of human eyes in response to various stimuli. The detailed data may relate to different aspects of a user's vision, and may be compared with corresponding standard vision parameters, to generate vision performance scores. The scores may be for each different aspect of vision, and/or may be combined to present an overall vision performance score. The score is also presented to the user as a measure of the user's vision performance. In embodiments, various stimuli is provided to the user through a mobile or any other gaming application that may be accessed by the user.

An exemplary application (hereinafter, referred to as "Sight Kit"), may be designed to measure the performance of a visual system through a series of interactive games.

While the specification describes features of the Sight Kit gaming application, they should be considered as exemplary embodiments only. Alternative embodiments are possible and will be apparent to those skilled in the art. Alternative embodiment may include variations and/or improvements in one or more of context, sequence, gaming levels, graphical representations, scoring systems, reporting methods, user-interface, and other aspects, in the gaming application. The gaming application may report a set of scores to the user in various categories. These scores can be an indication of how the individual user performs relative to all users. A weighted average of a user's scores may yield the Vision Performance Index (VPI) which, just like the component scores, may represent the user's vision performance relative to a baseline, such as the broader population.

In an embodiment, a user engages with a gaming application in accordance with embodiments of the present specification. In an example, the gaming application is referred to as the Sight Kit application. In an embodiment, the Sight Kit application is presented to the user through a mobile platform, such as a smartphone or any other portable electronic device including HMDs. In an embodiment, the user is presented with a series of views through the electronic device, which sequentially enable access to a type of stimulation, which could be in the form of one or more interactive games. In an embodiment, the user is able to securely access the Sight Kit application. In embodiments, a single mobile platform is used by multiple users to securely access the Sight Kit application. Secure access is enabled through a secure authentication process. Following are exemplary views and information presented to the user through the display of the electronic device, while attempting to securely access the Sight Kit application:

FIG. 19 illustrates screenshots 1900 of empty and error screens that may appear through the sight kit application, in accordance with an embodiment of the present specification.

Figure 20B:
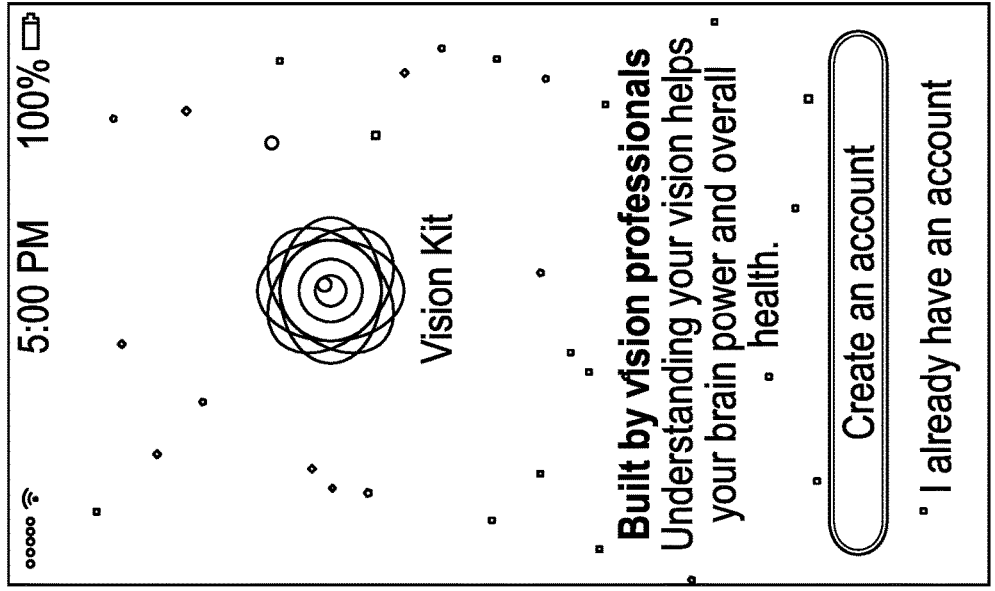
FIG. 20B illustrates a screenshot of home screen that may appear through the sight kit application, in accordance with an embodiment of the present specification.
Figure 20A:
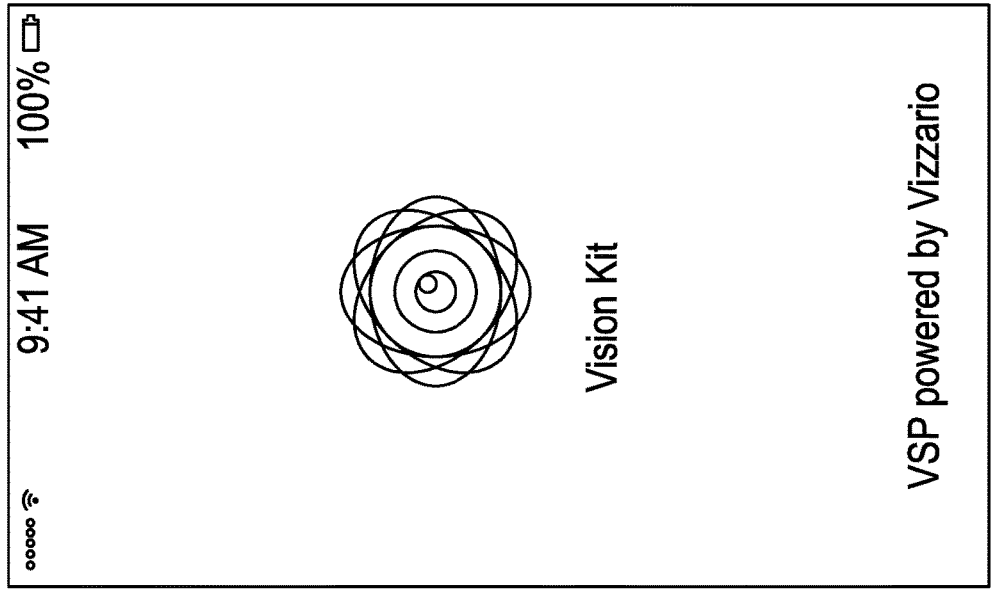
FIG. 20A illustrates a screenshot of splash screen that may appear through the sight kit application, in accordance with an embodiment of the present specification.

FIG. 20A illustrates a screenshot 2000A of splash screen that may appear through the sight kit application, in accordance with an embodiment of the present specification.

FIG. 20B illustrates a screenshot 2000B of home screen that may appear through the sight kit application, in accordance with an embodiment of the present specification.

Figure 20C:
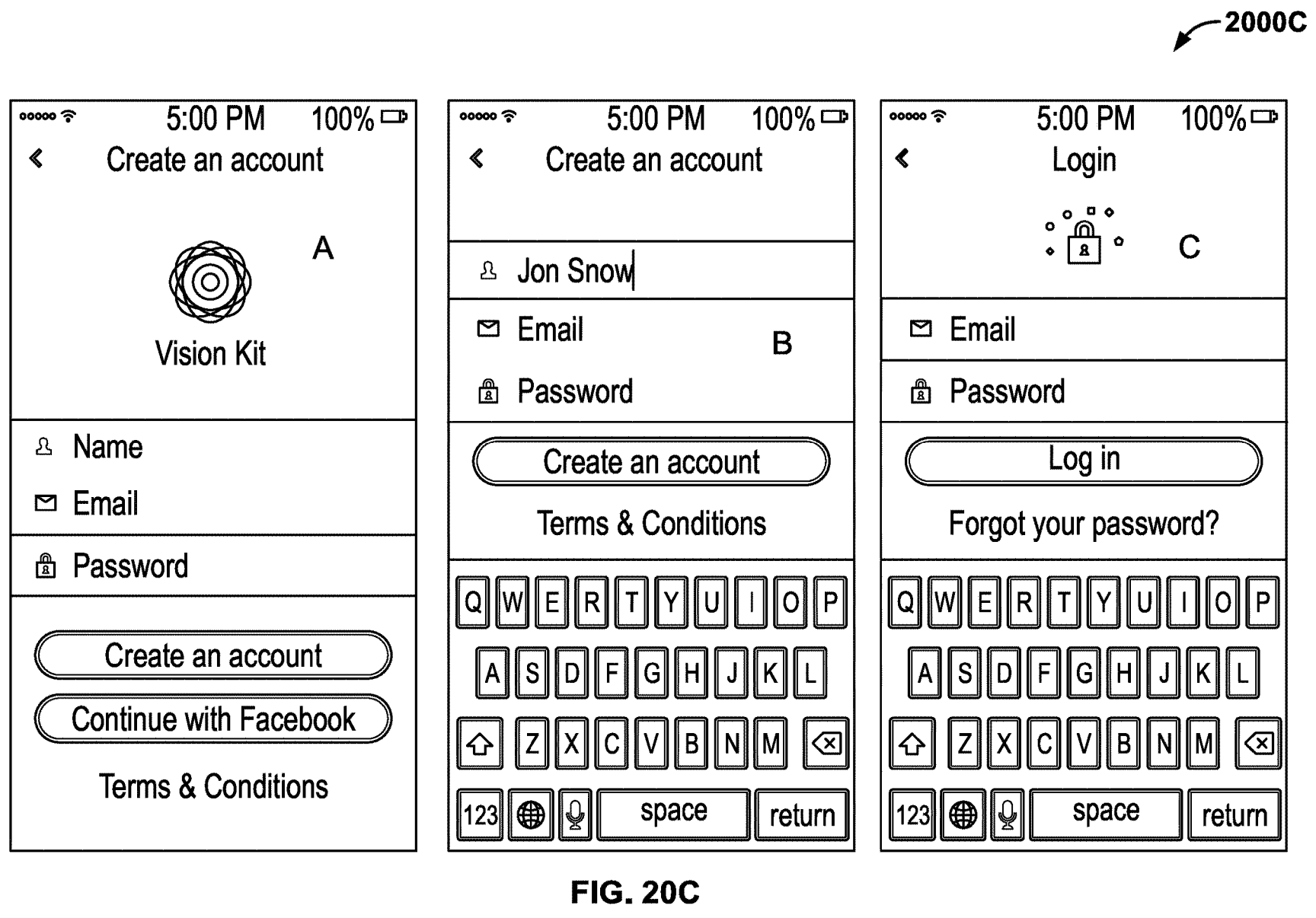
Figure 20C:
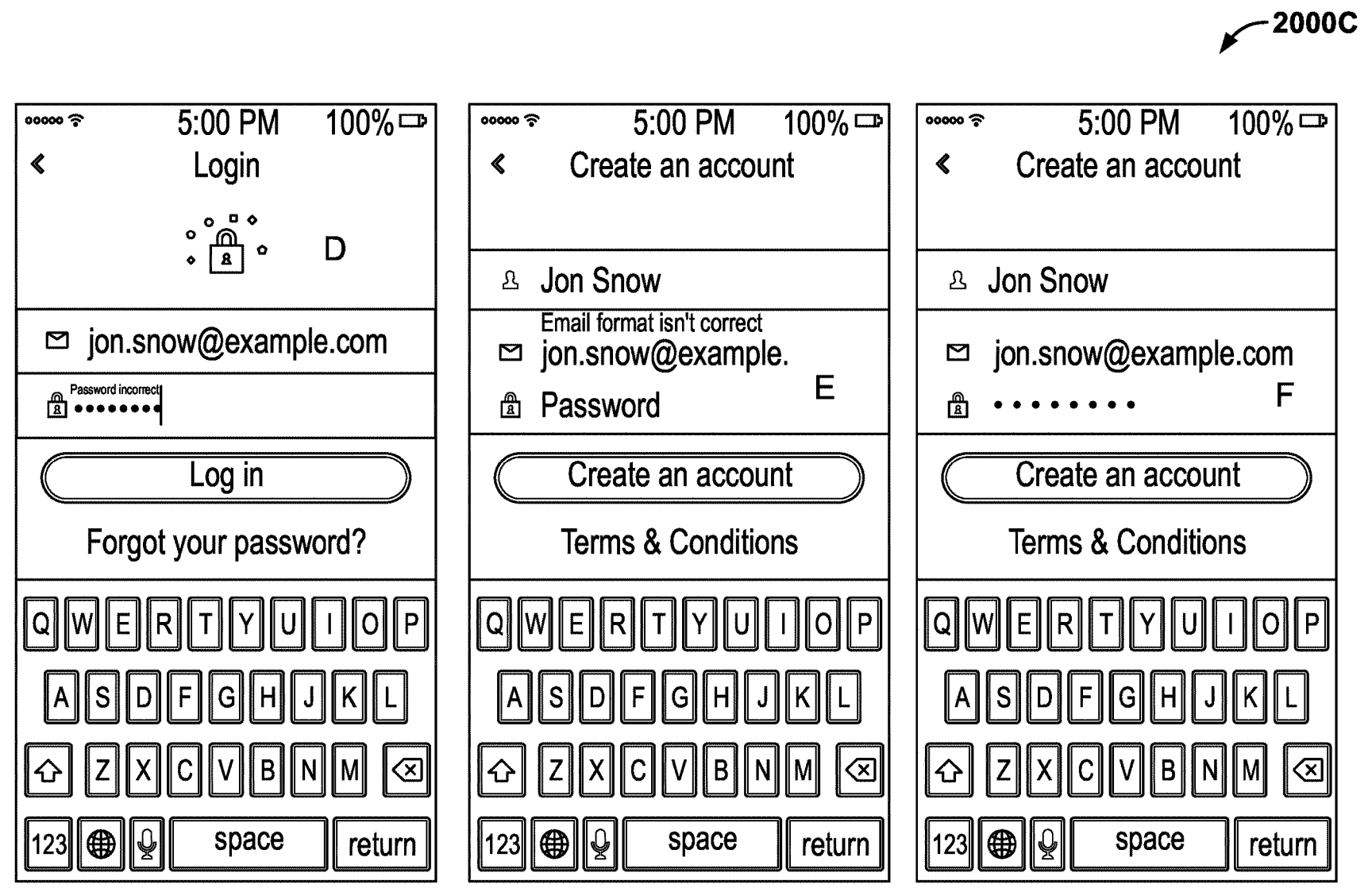

In embodiments, the application enables secure access. FIG. 20C illustrates a series of screenshots 2000C of the login (registration) process including an exemplary registration by a user named 'Jon Snow' that may appear through the sight kit application, in accordance with an embodiment of the present specification.

Figure 20E:
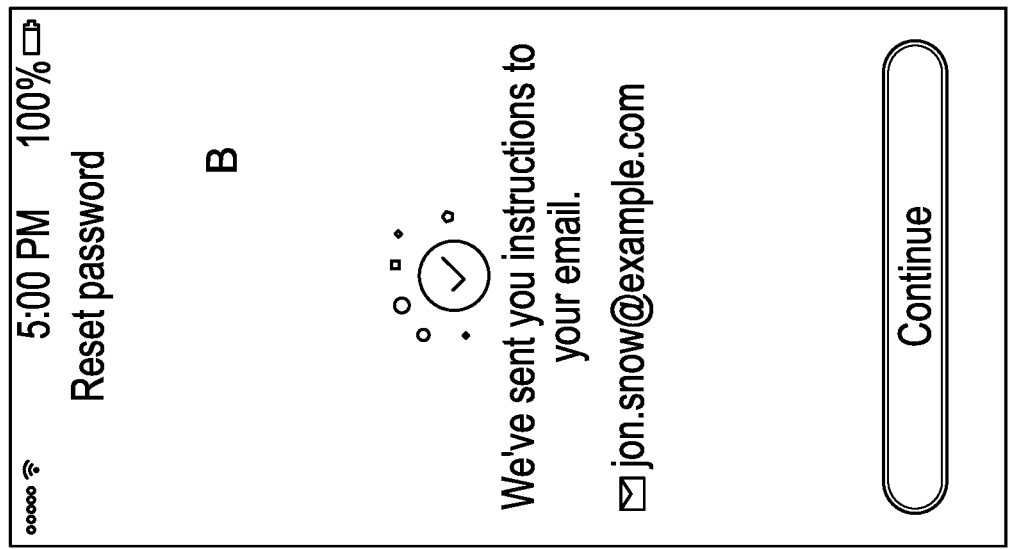
FIG. 20E illustrates a series of screenshots that may appear through the sight kit application in case a user forget their login information, in accordance with an embodiment of the present specification.
Figure 20D:
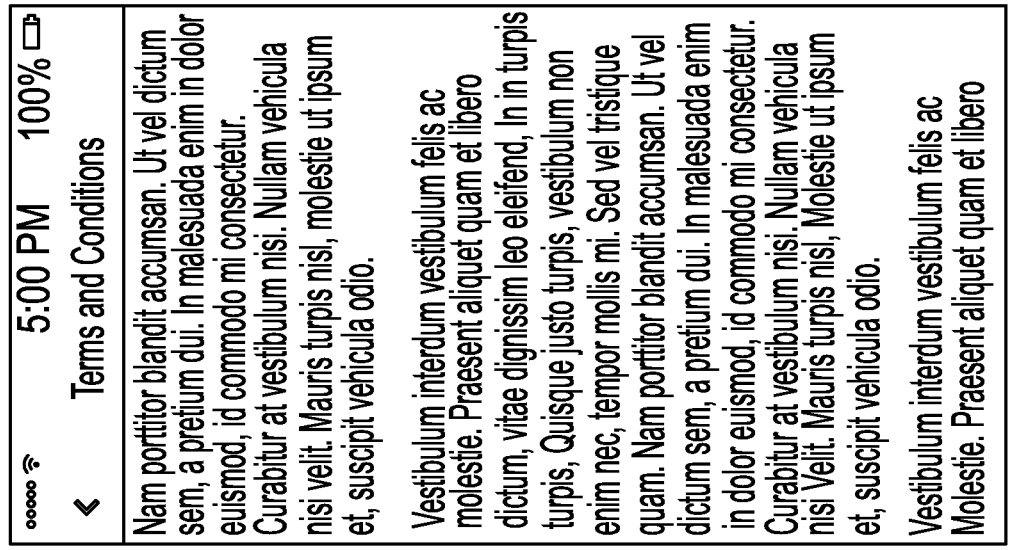
FIG. 20D illustrates a screenshot of a screen with terms and conditions that may appear through the sight kit application, in accordance with an embodiment of the present specification.

FIG. 20D illustrates a screenshot 2000D of a screen with terms and conditions that may appear through the sight kit application, in accordance with an embodiment of the present specification.

FIG. 20E illustrates a series of screenshots 2000E that may appear through the sight kit application in case a user forget their login information, in accordance with an embodiment of the present specification.

In embodiments, the user is prompted for personal information at the time of accessing the application for the first time. For example, the user is prompted for demographic information. In some embodiments, the demographic information is subsequently utilized to determine a standard or average score for similar demographics, which may be used for comparison of the user's score.

Figure 21A:
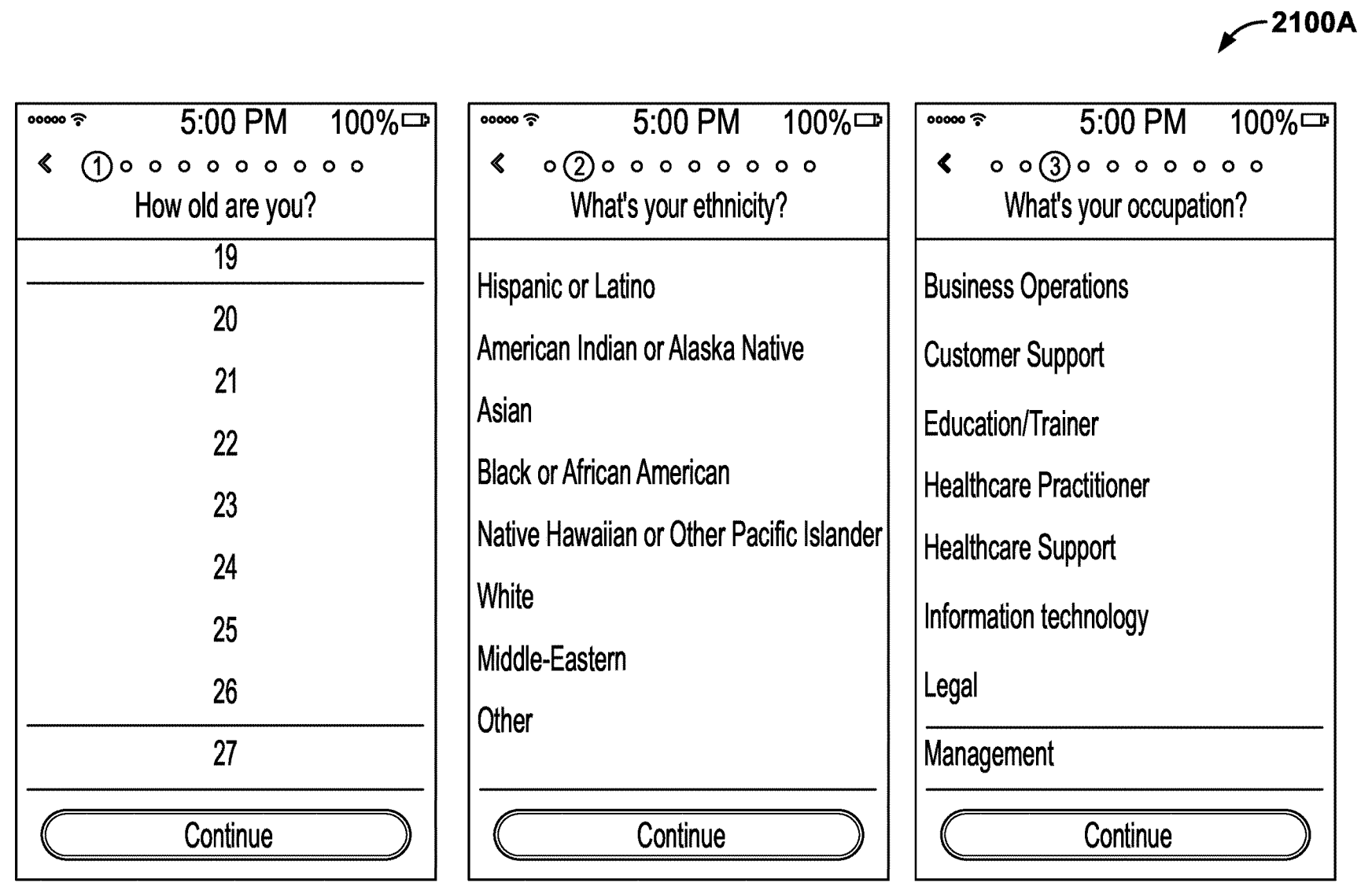
Figure 21A:
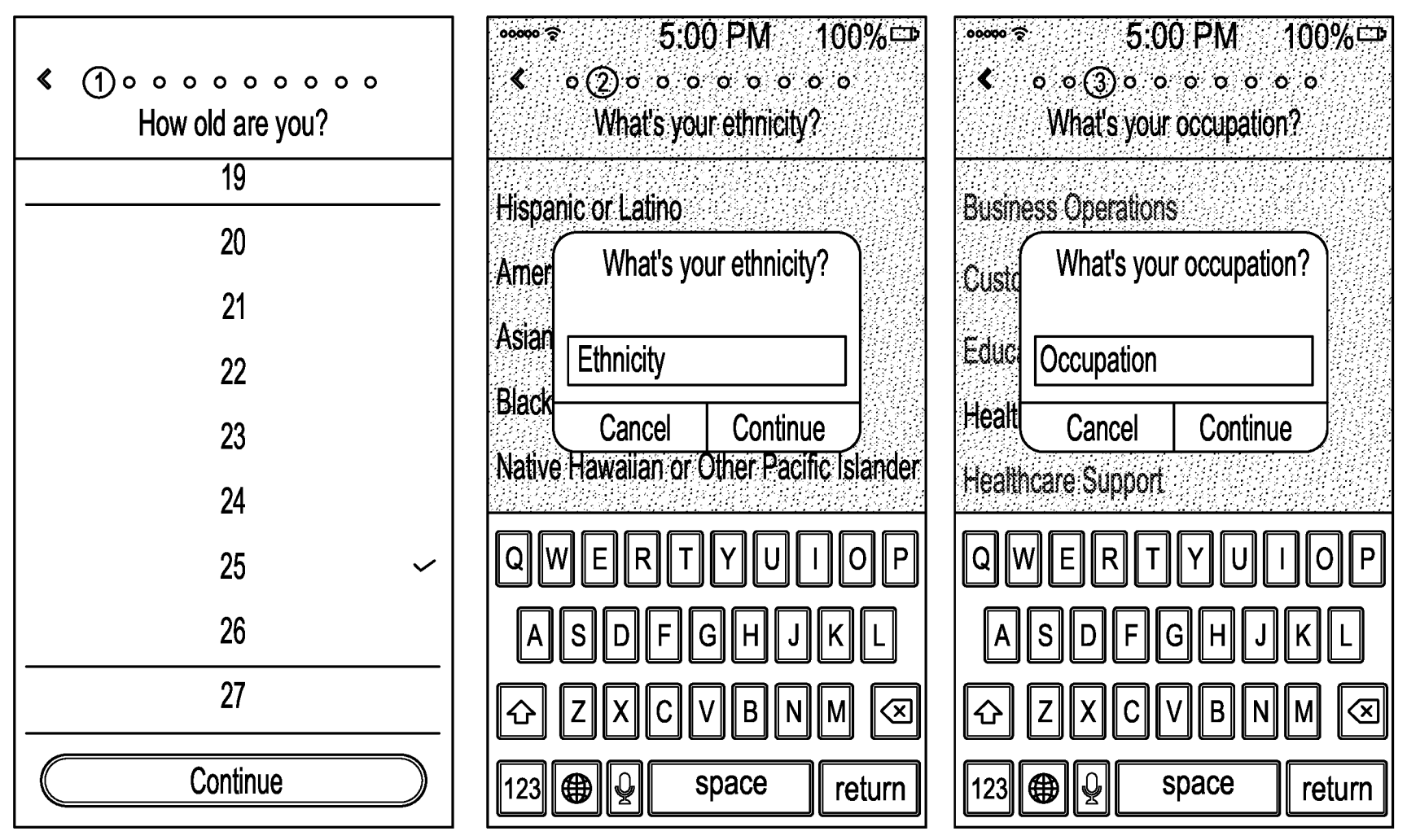

FIG. 21A illustrates a series of screenshots 2100A of screens that prompt a user with demographic questions that may appear through the sight kit application, in accordance with an embodiment of the present specification.

Figure 21B:
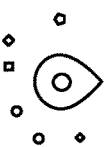
FIG. 21B illustrates a further series of screenshots of screens that prompt a user with demographic questions that may appear through the sight kit application, in accordance with an embodiment of the present specification.
Figure 21B:
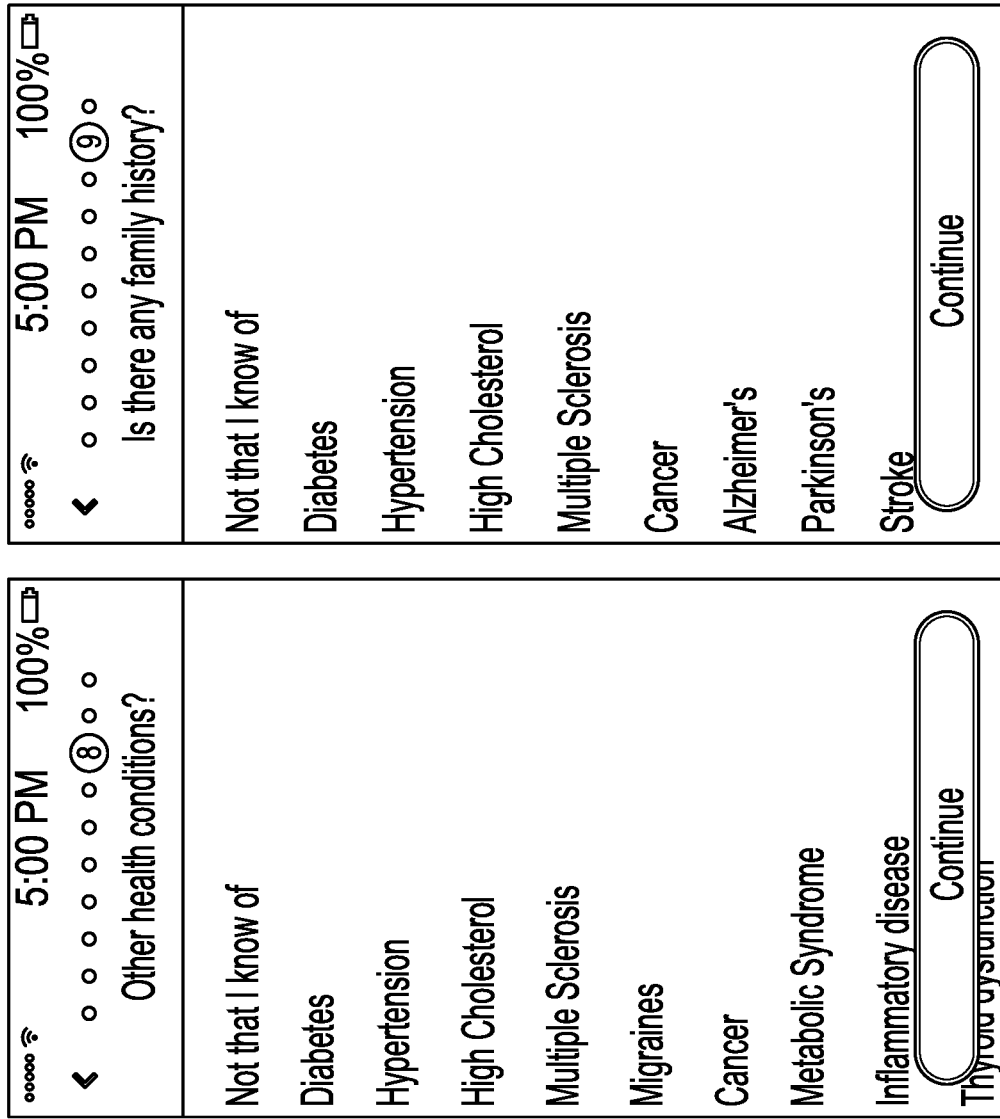

FIG. 21B illustrates a further series of screenshots 2100B of screens that prompt a user with demographic questions that may appear through the sight kit application, in accordance with an embodiment of the present specification.

FIG. 21C illustrates still further series of screenshots 2100C of screens that prompt a user with demographic questions that may appear through the sight kit application, in accordance with an embodiment of the present specification.

Figure 22:
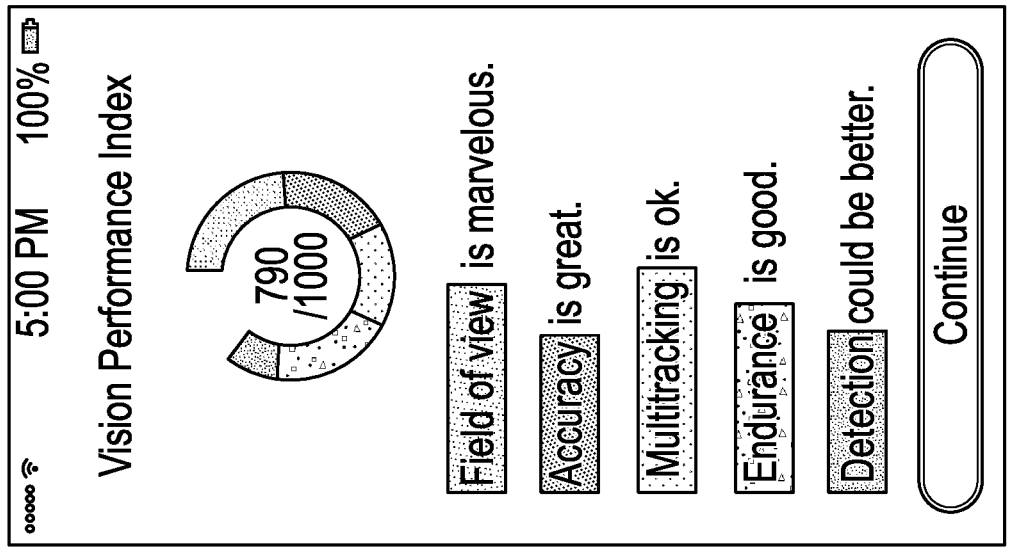
FIG. 22 illustrates a series of screenshots of screens that present a user with an initial VPI report that may appear through the sight kit application, in accordance with an embodiment of the present specification.

FIG. 22 illustrates a series of screenshots 2200 of screens that present a user with an initial VPI report that may appear through the sight kit application, in accordance with an embodiment of the present specification. In an embodiment, the initial VPI report is an example of a set of scores for other users with demographics similar to the actual user. In another embodiment, the initial VPI report is present to a returning user, and includes previous scores achieved by the user.

Figure 23:
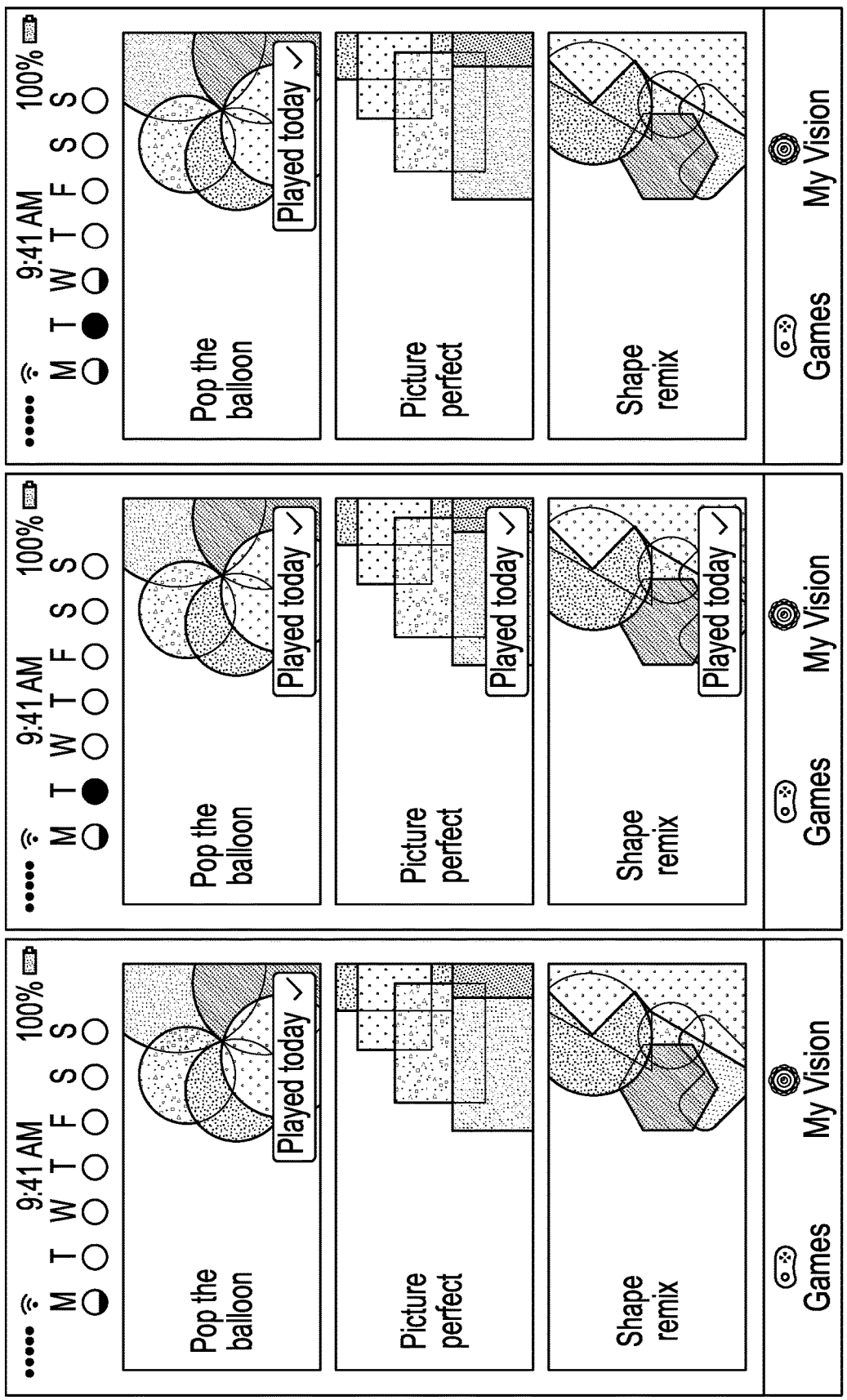
FIG. 23 illustrates screenshots of different screens that may appear at separate times, prompting a user to select a game to play that may appear through the sight kit application, in accordance with an embodiment of the present specification.

FIG. 23 illustrates screenshots 2300 of different screens that may appear at separate times, prompting a user to select a game to play that may appear through the sight kit application, in accordance with an embodiment of the present specification. In embodiments, the user interface differs based on the past interaction of the user. The user may be presented with information about the games they have played previously.

In an embodiment, the Sight Kit application is divided into three games. Within games are successive rounds with more or less altered experiences.

Game 1: Pop the Balloons

In this round, users may be required to tap in response to the appearance of some visual stimuli (targets) and not others (distractors). This provides data suitable to psychometric curve fitting where the proportion of correct discriminations (tapping targets vs. not tapping targets) as a function of color, contrast or acuity differences can be used to estimate discrimination thresholds (i.e. detection measures, as described above). The game may encourage speedy responses to specific areas of the display which provides data for Reaction time and Targeting precision (i.e. Accuracy measures, as described above). The game may have multiple rounds, which may be presented to the user in a sequence. Alternatively, the user may choose to interact with any round. FIGS. 24A to 24F illustrate various interfaces seen for the game of 'Pop the Balloon'.

Round 1

FIG. 24A illustrates a screenshot 2400A of Pop the Balloons Round 1 instructions, which may be presented through the sight kit application in accordance with an embodiment of the present specification.

FIG. 24B illustrates a screenshot 2400B of Pop the Balloons Round 1 game, which may be presented through the sight kit application in accordance with an embodiment of the present specification.

The first round of Pop the Balloons features balloons rising from the bottom of the screen to the top ('floating' into and out of view at the display edges). Some balloons feature a striped pattern while others are solid, and users may tap the striped balloons while ignoring the solid ones (contrast discrimination). The colors used for each balloon may be random (although alternating stripes in the striped balloons are white). The size of balloons may decrease over time. The changing size may reflect acuity influence, both in balloon size and spatial frequency of stripes within balloons. In embodiments, the speed of movement may increase over time and the contrast of the striped patterns may decrease over time. At the beginning of the round, balloons may appear one at a time. Such an appearance may provide and measure focused attention of the user. Gradually, more balloons may be presented on the display at a time, requiring tracking of multiple objects at once. Presenting multiple balloons at the same time may probe divided attention of the user. An optimal strategy early on might be to look to the middle of the bottom edge of the display to catch balloons as they first appear; therefore the horizontal position of the appearing balloons might be more or less distant from fixation. This may help determine the user parameters corresponding to field of view.
Round 2

FIG. 24C illustrates a screenshot 2400C of Pop the Balloons Round 2 instructions, which may be presented through the sight kit application in accordance with an embodiment of the present specification.

FIG. 24D illustrates a screenshot 2400D of Pop the Balloons Round 2 game, which may be presented through the sight kit application in accordance with an embodiment of the present specification.

In this round, balloons do not move, but rather appear very briefly. There is no color or contrast variety, and acuity may be the primary mechanism for discrimination. Users may pop the balloon shapes while ignoring other, similar shapes. The more similar the shape is to a balloon, the harder it may be to discriminate leading to false positive responses. Variation in color differences from the background may be added as an additional source of color discrimination measures.

In this game, Reaction times and Targeting precision are may be a major component for measuring Accuracy. An optimal strategy might be to fixate on the center of the display giving rise to a Field of View component. Objects may appear one at a time, with gaps of time in between, negating the possibility of a Multi-Tracking measure.
Round 3

Figure 24F:
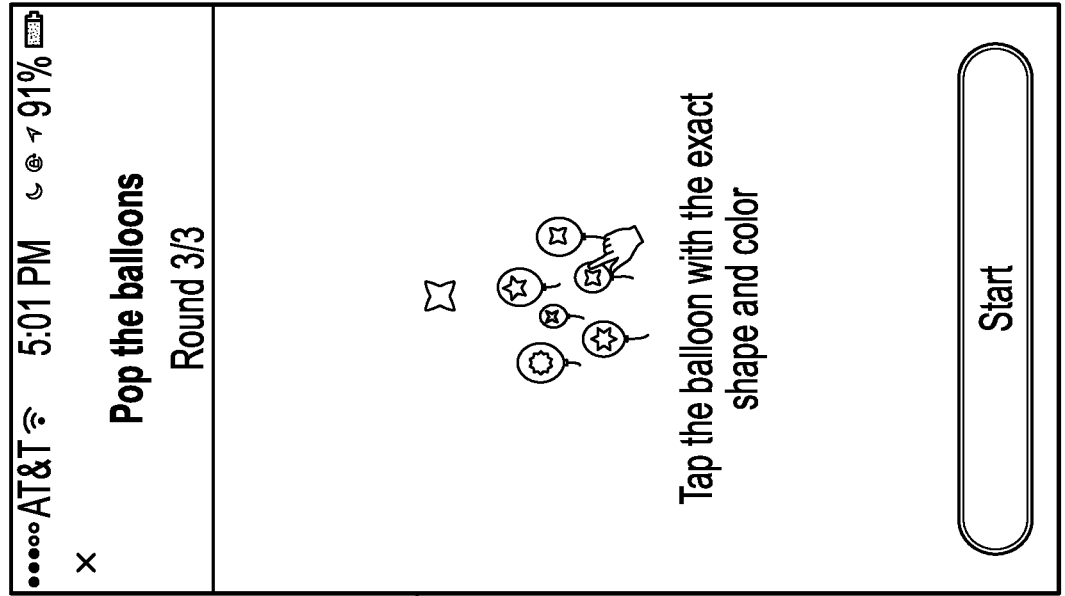
FIG. 24F illustrates a screenshot of Pop the Balloons Round 3 game, which may be presented through the sight kit application in accordance with an embodiment of the present specification.
Figure 24E:
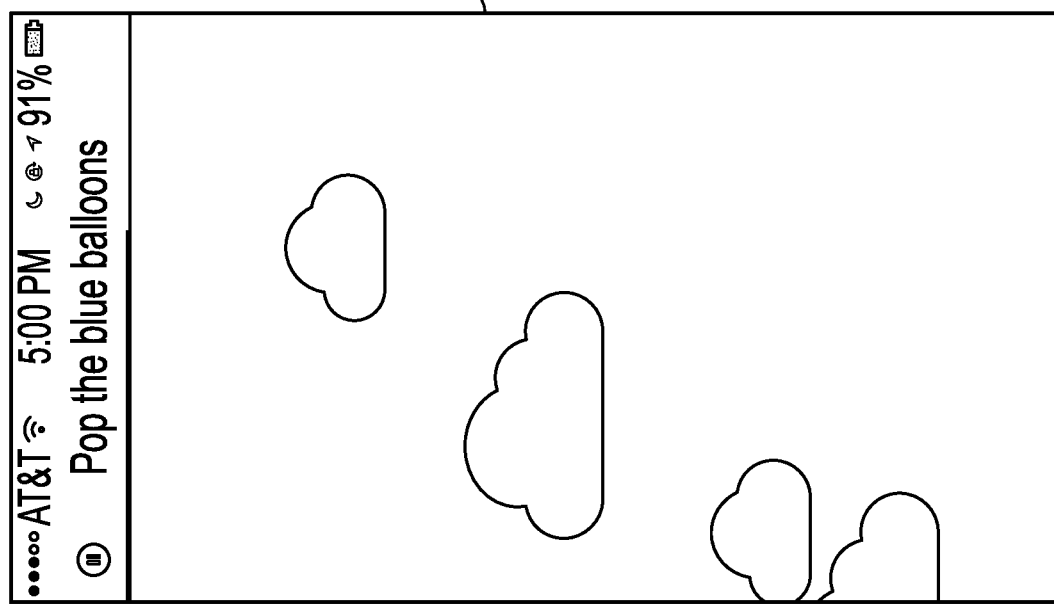
FIG. 24E illustrates a screenshot of Pop the Balloons Round 3 instructions, which may be presented through the sight kit application in accordance with an embodiment of the present specification.

FIG. 24E illustrates a screenshot 2400E of Pop the Balloons Round 3 instructions, which may be presented through the sight kit application in accordance with an embodiment of the present specification.

FIG. 24F illustrates a screenshot 2400F of Pop the Balloons Round 3 game, which may be presented through the sight kit application in accordance with an embodiment of the present specification.

Figure 25B:
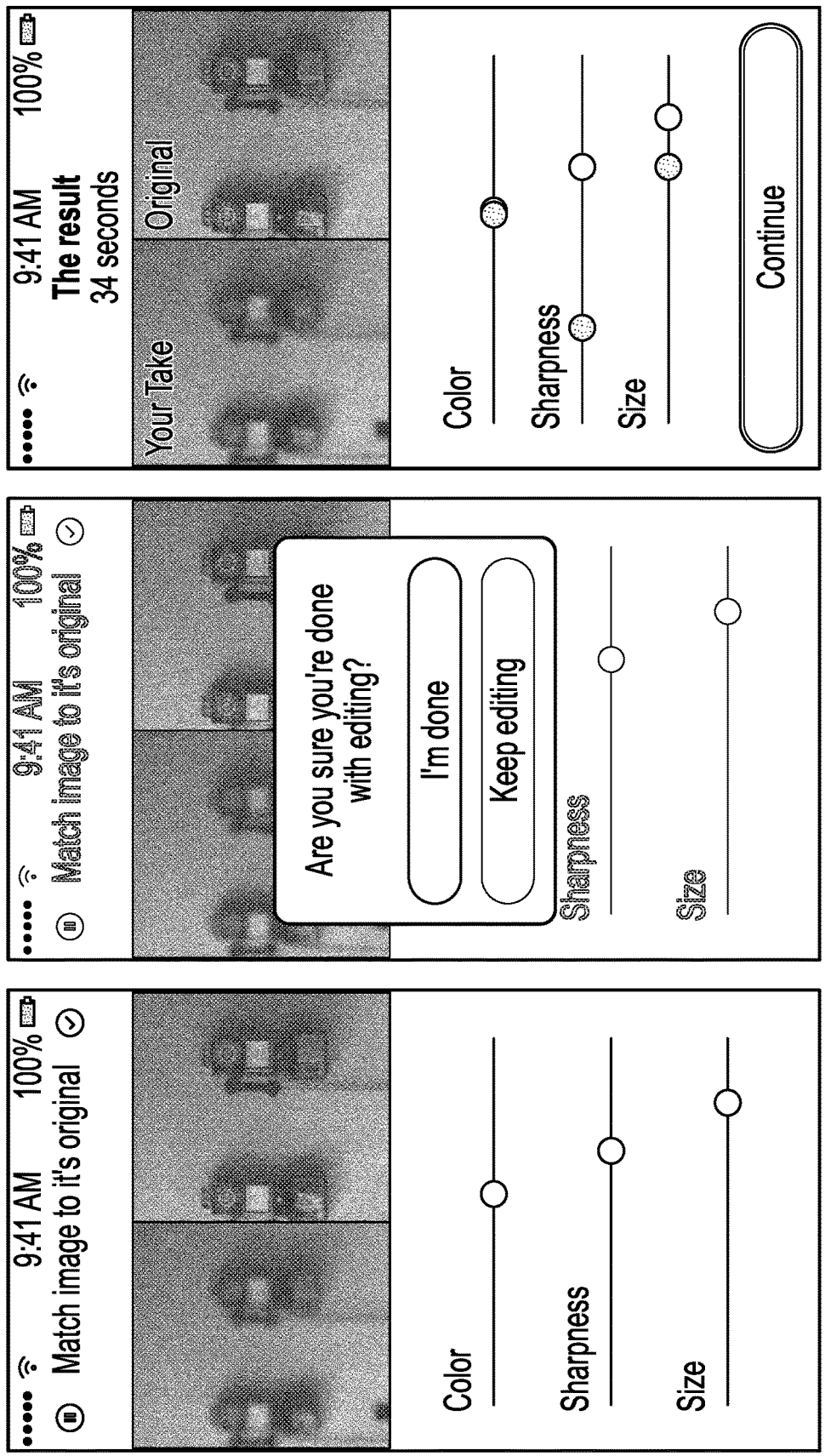
FIG. 25B illustrates a series of screenshots of Picture Perfect Round 1 game, which may be presented through the sight kit application in accordance with an embodiment of the present specification.

In the third round, which may also be a final round, balloons may neither move nor appear briefly; instead difficulty may be increased by introducing a feature conjunction search task with increasing set size. Users may find the matching color/shape combination requiring color and acuity discrimination (an indication of Detection). Reaction time may be an important characteristic, with Targeting precision of reduced interest given the static and persistent nature of the stimuli (an indication of Accuracy). Field of View may also be somewhat indicated, although targets randomly placed towards the center may be found faster on average than when targets are towards the edges of the balloon clusters. Multi-Tracking may have a significant impact here, depending upon whether users employ serial or parallel processing of visual stimuli; this may be revealed later by the dependency, or lack thereof, of set size on reaction time (Hick's law).
Game 2: Picture Perfect In this game, an image may be displayed to the user along with its distorted version. The user may be provided with tools to vary display parameters of the distorted image in order to match it to the original image. In an embodiment, the display parameters may include a combination of one or more of color, sharpness, and size, among other. Once the user confirms completing the task, results may be presented to the user by comparing the user's selections and the correct selections. In an embodiment, greater the proximity of the user's selection to the correct selection, the greater is the vision performance of the user. The Picture Perfect game may not require a fast reaction, although users may be encouraged to work fast (for example, the number of settings made in a fixed period of time may be used to generate a Reaction score). In an embodiment, the game consists of multiple rounds. FIGS. 25A and 25B illustrate a series of screenshots 2500A and 2500B respectively, of Picture Perfect Round 1 game, which may be presented through the sight kit application in accordance with an embodiment of the present specification. In some embodiment, sliders are provided to the user to vary different parameters in order to correct a distorted image. In other embodiments, other graphical, numerical, or any other, tools can be provided for this purpose.

Figure 25C:
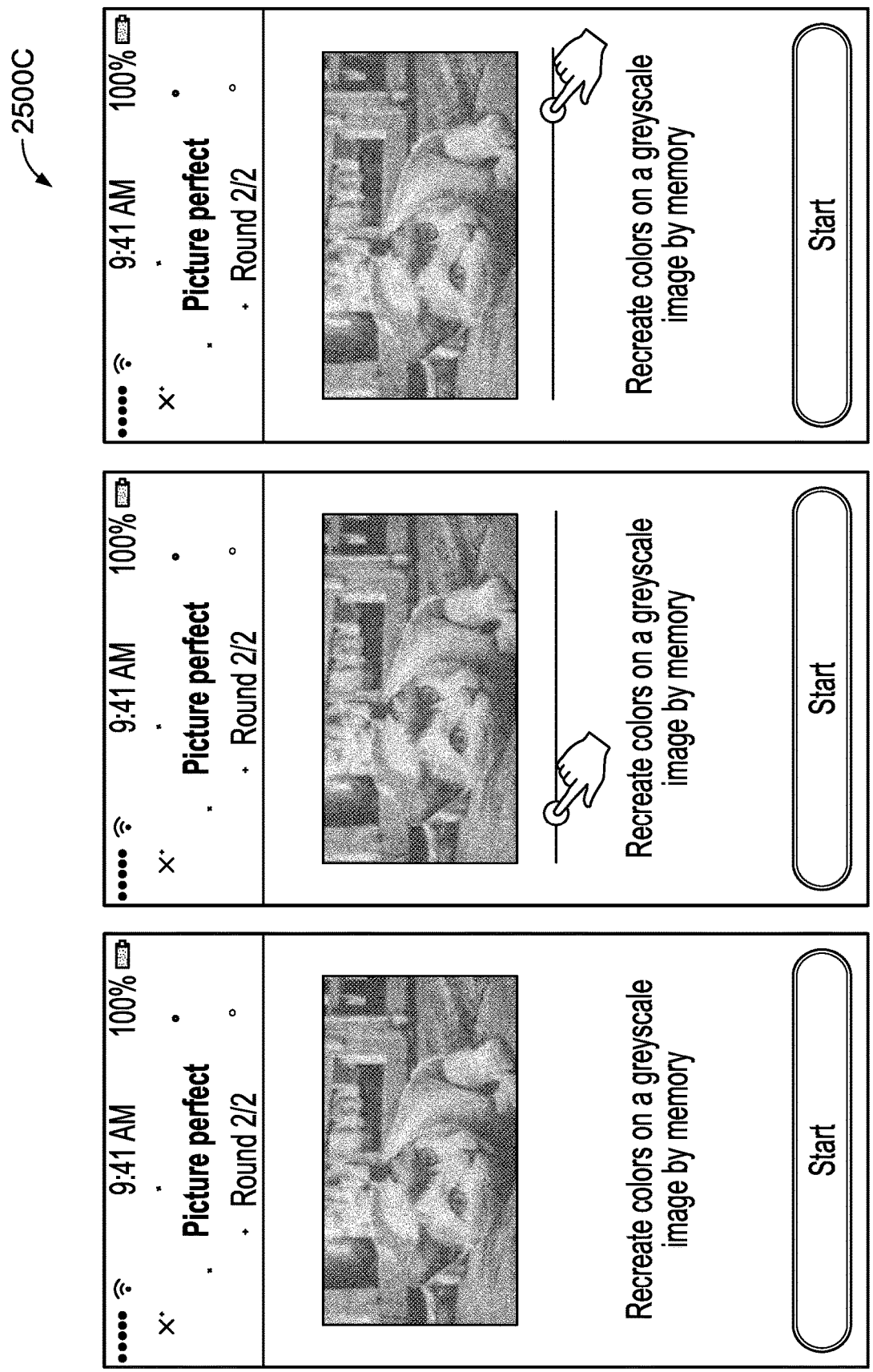
FIG. 25C illustrates a series of screenshots of Picture Perfect Round 2 game, which may be presented through the sight kit application in accordance with an embodiment of the present specification.

FIGS. 25C, 25D, and 25E illustrate a series of screenshots 2500C, 2500D, and 2500E respectively, of Picture Perfect Round 2 game, which may be presented through the sight kit application in accordance with an embodiment of the present specification. The advanced round may present the user with the original image and the distorted image at separate times, and not simultaneously. The user is then required to correct the distorted image by recalling the original image from their memory.

Figure 25F:
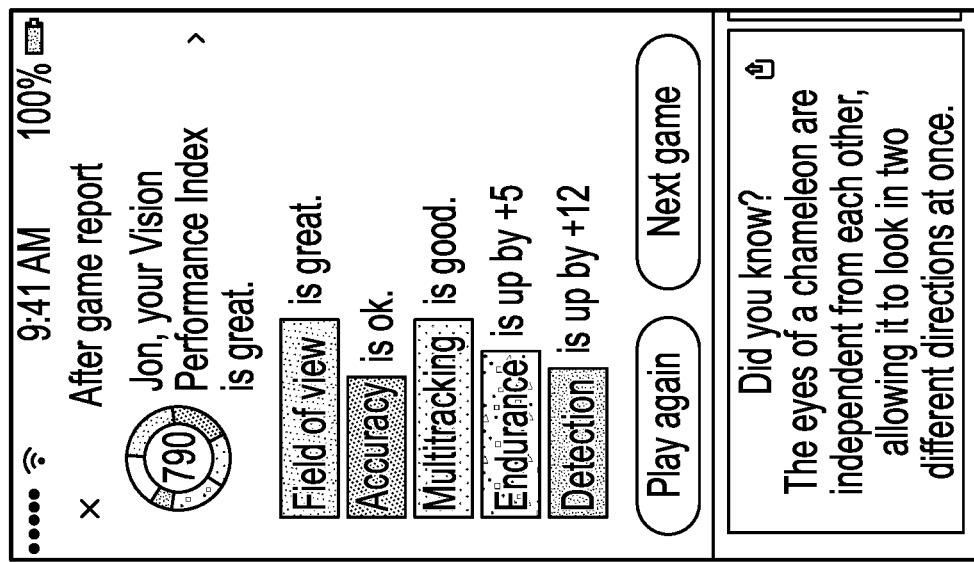
FIG. 25F illustrates a screenshot of an exemplary after game report for a user, which may be presented through the sight kit application in accordance with an embodiment of the present specification.

FIG. 25F illustrates a screenshot 2500F of an exemplary after game report for a user, which may be presented through the sight kit application in accordance with an embodiment of the present specification.

The Picture Perfect game may enable partial indication of vision parameters related to Field of View and Multi-Tracking, because users may freely sample the visual scene without restriction. Depending on which sliders are available to users in a given round, various measures of discrimination (Detection) may be made. Scores may be inversely proportional to the magnitude of error between the correct level of each adjustment slider and the user's settings. 'Color', 'Hue' and 'Saturation' adjustments may contribute to Color measurements. 'Size' and 'Sharpness' adjustments may contribute to Acuity measurements.
Game 3: Shape Remix/Memory Match Instructions to interact with the game may be optionally provided to the user before starting the game. In an embodiment, the user is presented with an original image including multiple elements. The task for the user is to edit the elements in an alternate image, in order to match the element and their layout as previously shown in the original image. In some embodiments, the user is provided with tools that enable varying different characteristics of each element. For example, the user is able to vary the hue, saturation, contrast, sharpness, size, or any other, parameter separately for each element. Once the user confirms completing the task, the result may be presented by displaying the original image adjacent to the image recreated by the user. Additionally, numerical scores and verbal reactions may be presented to the user.

Figure 26B:
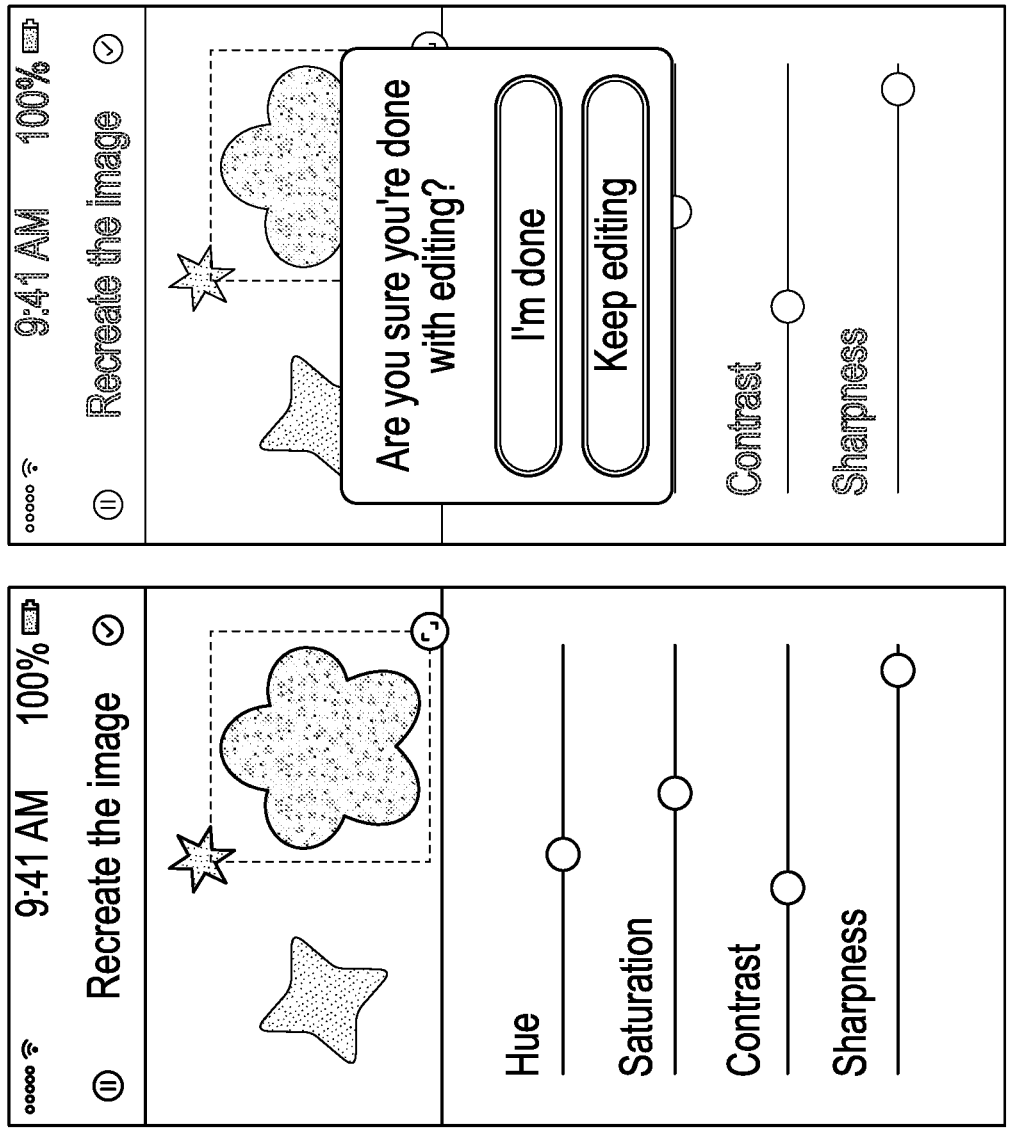
FIG. 26B illustrates a similar set of screenshots for 'Shape Remix' game, its instructions, and after game report, which may be presented through the sight kit application in accordance with an embodiment of the present specification.

FIGS. 26A, 26B, and 26C, illustrate similar set of screenshots 2600A, 2600B, and 2600C respectively, for 'Shape Remix' game, its instructions, and after game report, which may be presented through the sight kit application in accordance with an embodiment of the present specification.
Game 4: Speed Pop Instructions to interact with the game may be optionally provided to the user before starting the game. In an embodiment, the user is presented with streaming shapes and images, which includes balloons and an assortment of other shapes. The task for the user is to tap any balloon while avoiding tapping any other shape. In an embodiment, both the balloons and assortment of other shapes are colored the same. Additionally, numerical scores and verbal reactions may be presented to the user.

Game 5: Match Pop

Instructions to interact with the game may be optionally provided to the user before starting the game. In an embodiment, the user is presented with an example object having a shape and a color. The objective of the game is for the user to tap the balloon that includes an object that matches the example object provided, with respect to both shape and color. Additionally, numerical scores and verbal reactions may be presented to the user.

Game 6: Star Catch

Instructions to interact with the game may be optionally provided to the user before starting the game. In an embodiment, the user is expected to navigate a ship to collect target shapes, where the target shapes may be defined for or presented to the user beforehand. Additionally, numerical scores and verbal reactions may be presented to the user.

In an embodiment, an after game report is generated after each game is played and provides a user with their overall VPI as well as how each FAMED component was affected by their performance in the game. Each report may also show how the user performed compared to their age group. In addition, each report may provide an option for the user to learn more about a VPI in depth. A fun fact may also be presented alongside the report, in addition to a directory and/or map of local eye specialists.

FIG. 27 illustrates screenshots 2700 of VPI game reports after playing different games that may appear through the sight kit application, in accordance with an embodiment of the present specification.

Figure 28:
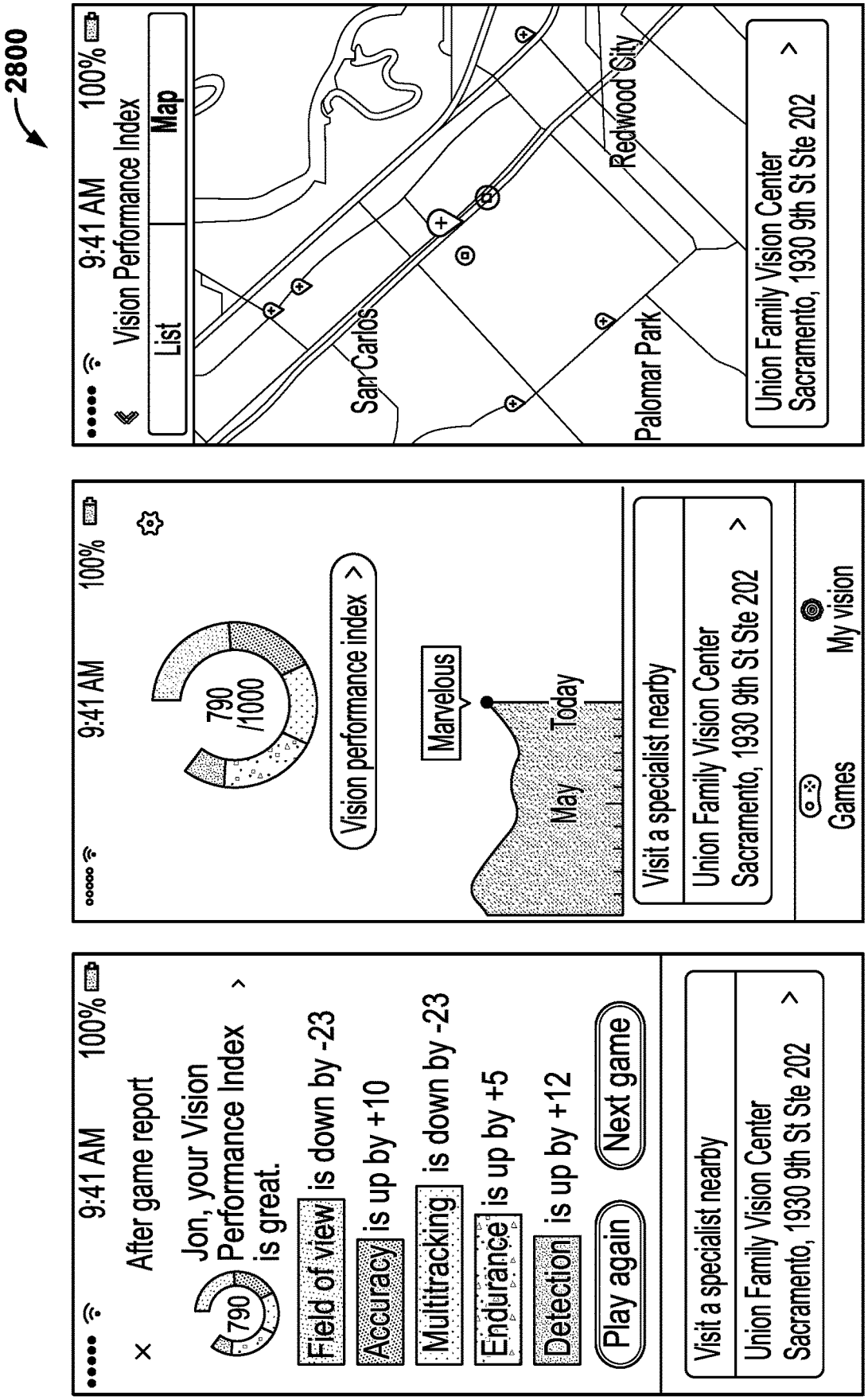
FIG. 28 illustrates some screenshots that may appear based on the user's VPI report, where the screens suggest doctors and/or eye-care practitioners, in accordance with an embodiment of the present specification.

FIG. 28 illustrates some screenshots 2800 that may appear based on the user's VPI report, where the screens suggest doctors and/or eye-care practitioners, in accordance with an embodiment of the present specification.

FIG. 29 illustrates some screenshots 2900 of the screens that present a user's profile that may appear through the sight kit application, in accordance with an embodiment of the present specification. Each screenshot present the profile of the user over a different time span and/or at different points of time. The user may select to view details of the VPI through their profile.

Figure 30A:
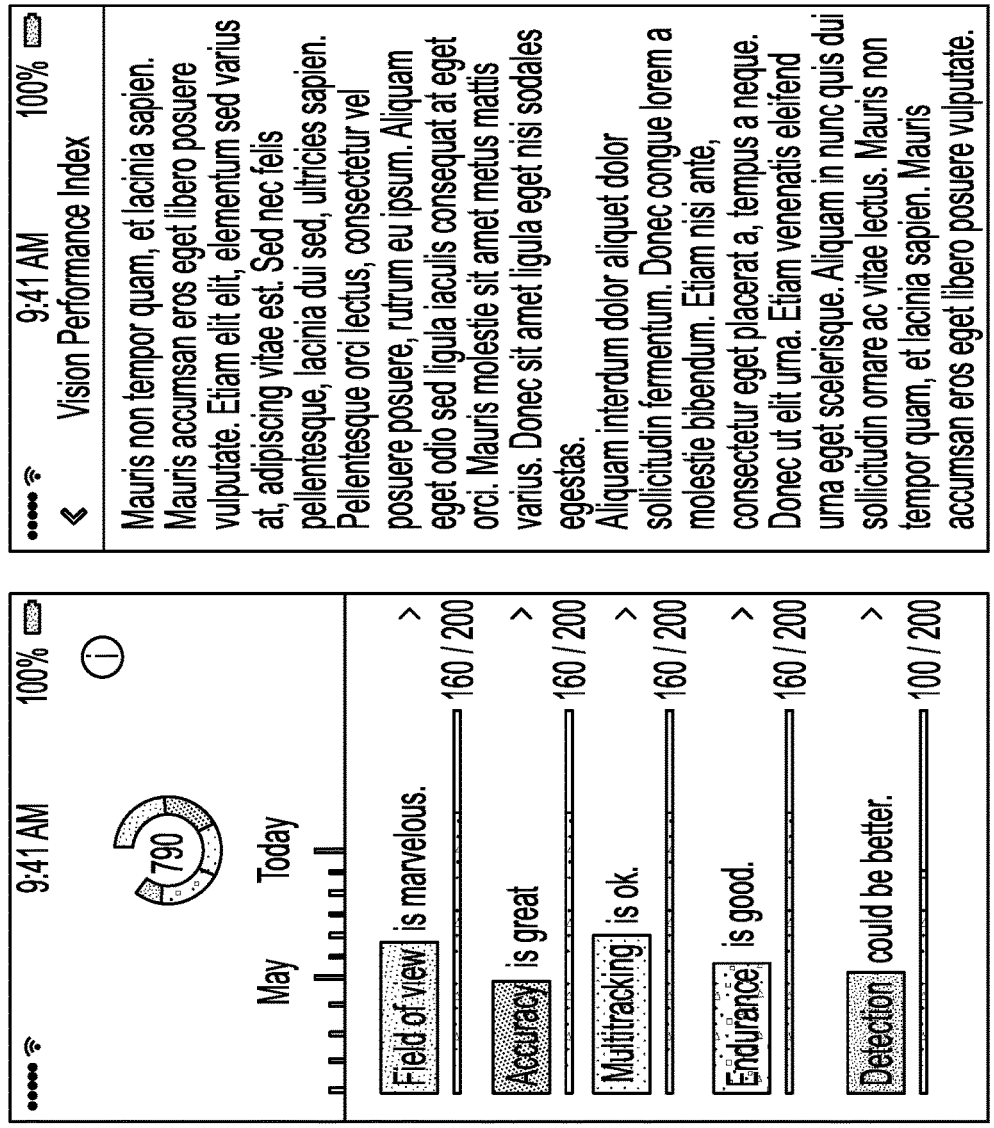
FIG. 30A illustrates some screenshots of the VPI breakdown that may appear through the sight kit application, in accordance with an embodiment of the present specification.

FIG. 30A illustrates some screenshots 3000A of the VPI breakdown that may appear through the sight kit application, in accordance with an embodiment of the present specification.

Figure 30B:
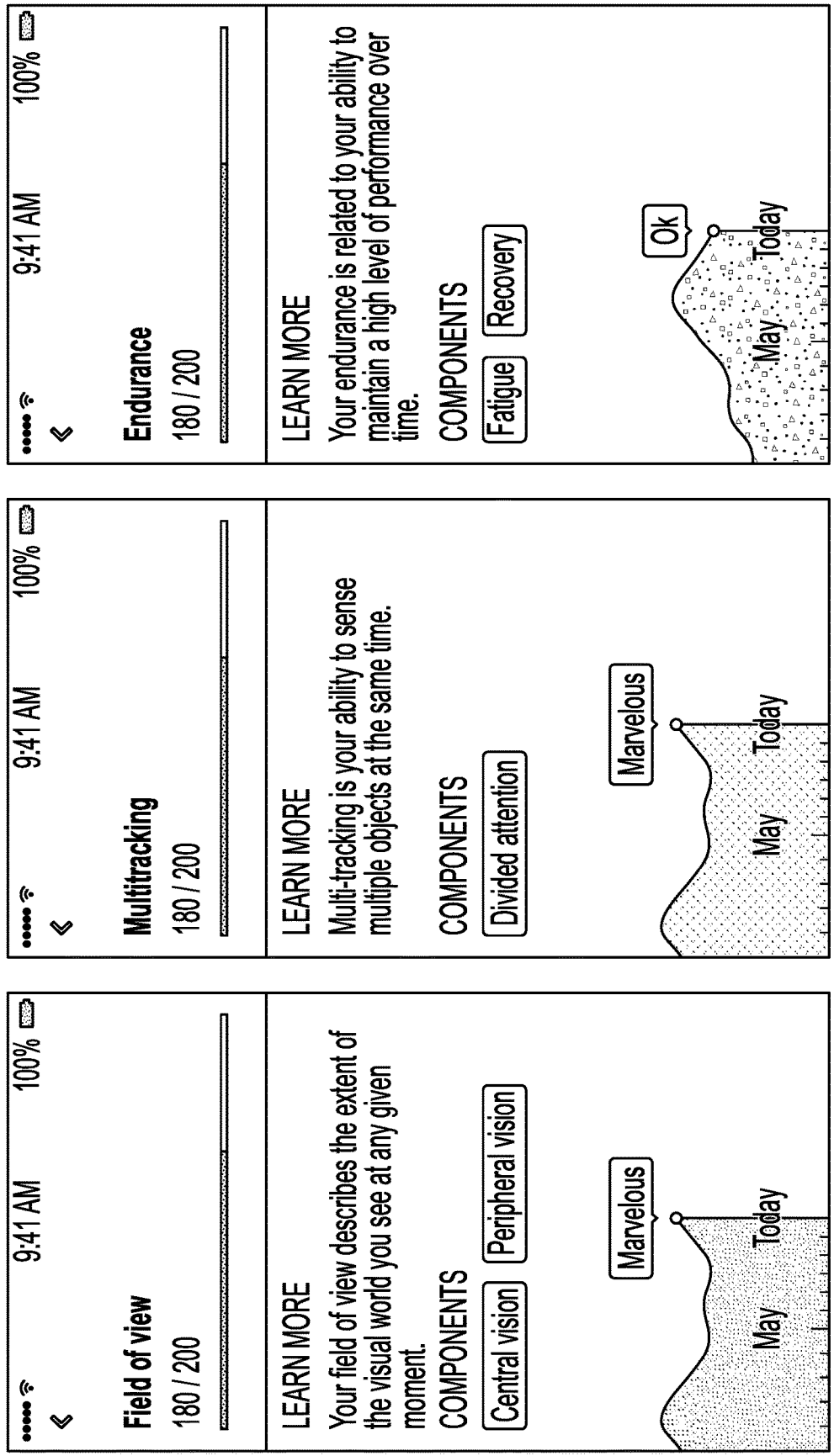
FIG. 30B illustrates some screenshots of the VPI breakdown that provide details about each FAMED parameter, through the sight kit application in accordance with an embodiment of the present specification.
Figure 30B:
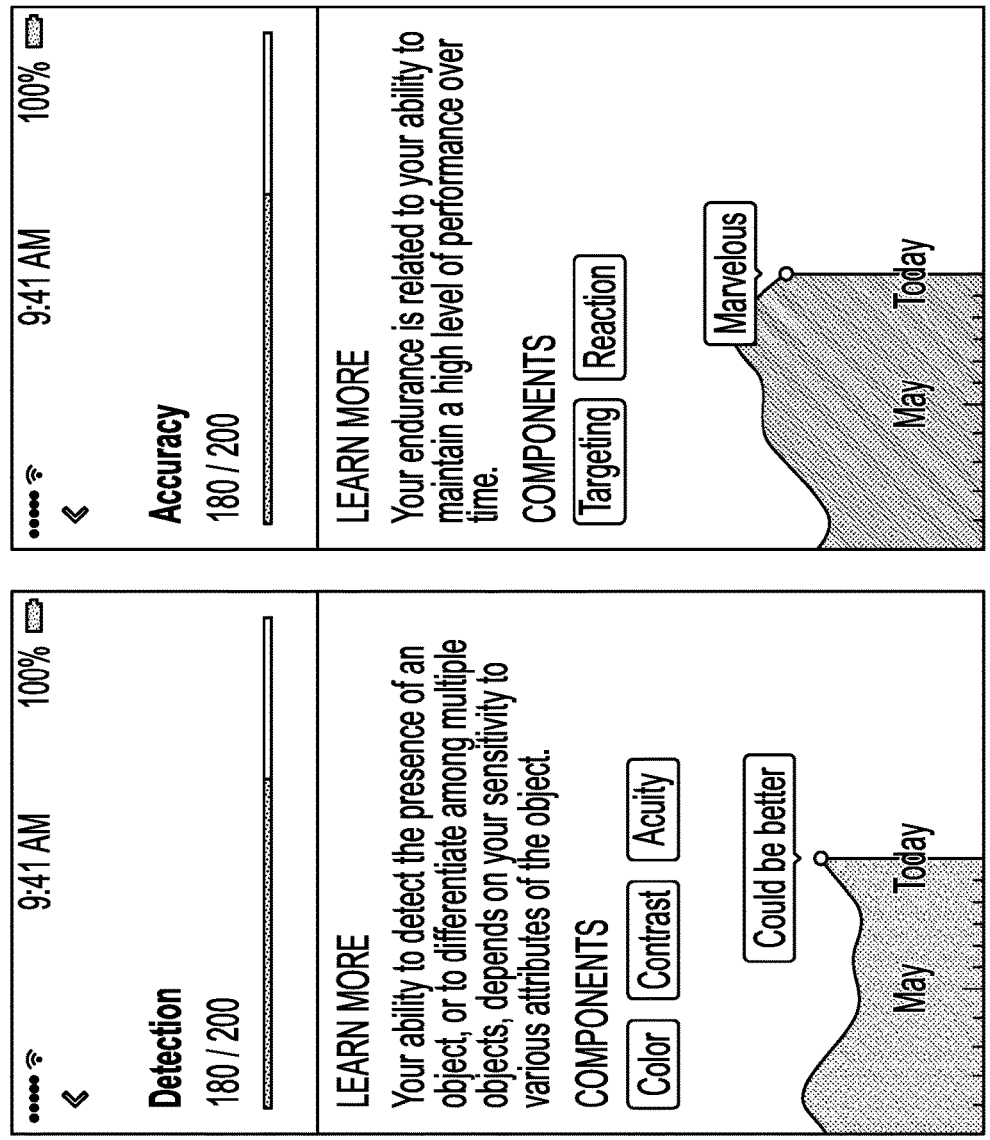

FIG. 30B illustrates some screenshots 3000B of the VPI breakdown that provide details about each FAMED parameter, through the sight kit application in accordance with an embodiment of the present specification.

Figure 30C:
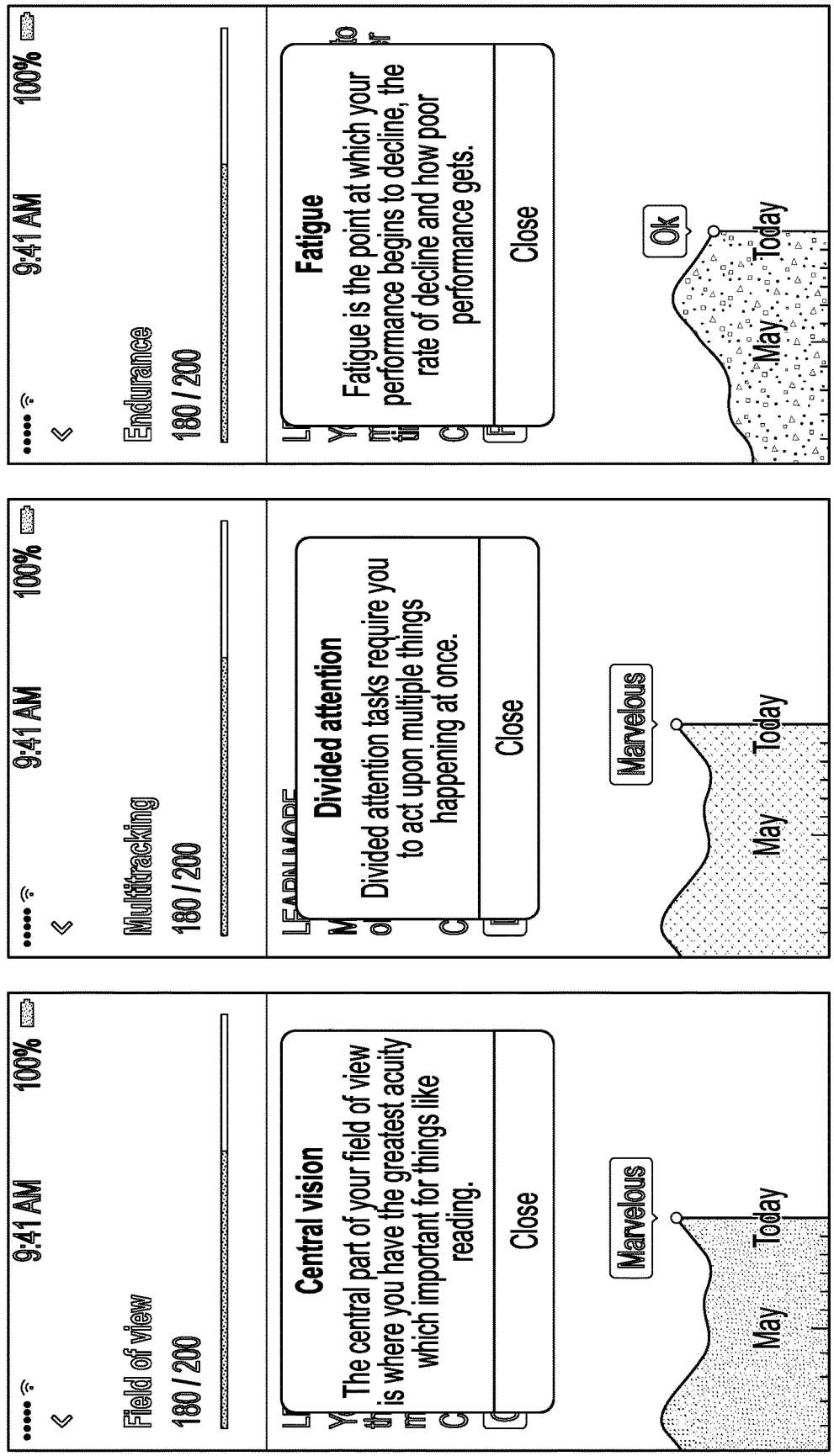
FIG. 30C illustrates some screenshots of the VPI breakdown that provide details of parameters within each FAMED parameter, through the sight kit application in accordance with an embodiment of the present specification.
Figure 30C:
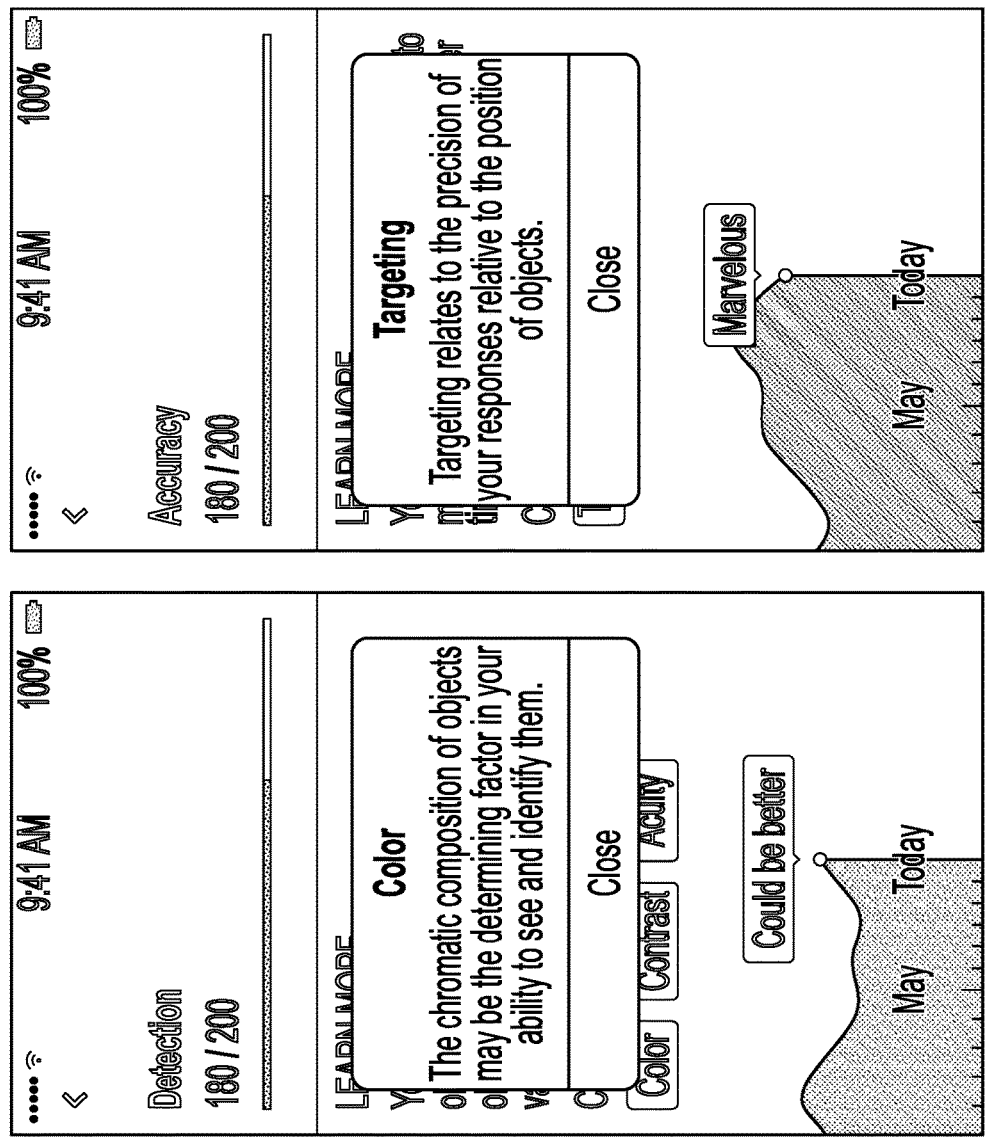

FIG. 30C illustrates some screenshots 3000C of the VPI breakdown that provide details of parameters within each FAMED parameter, through the sight kit application in accordance with an embodiment of the present specification.

FIG. 30D illustrates some screenshots 3000D of the VPI breakdown that provide further details of parameters within each FAMED parameter, through the sight kit application in accordance with an embodiment of the present specification.

Figure 31:
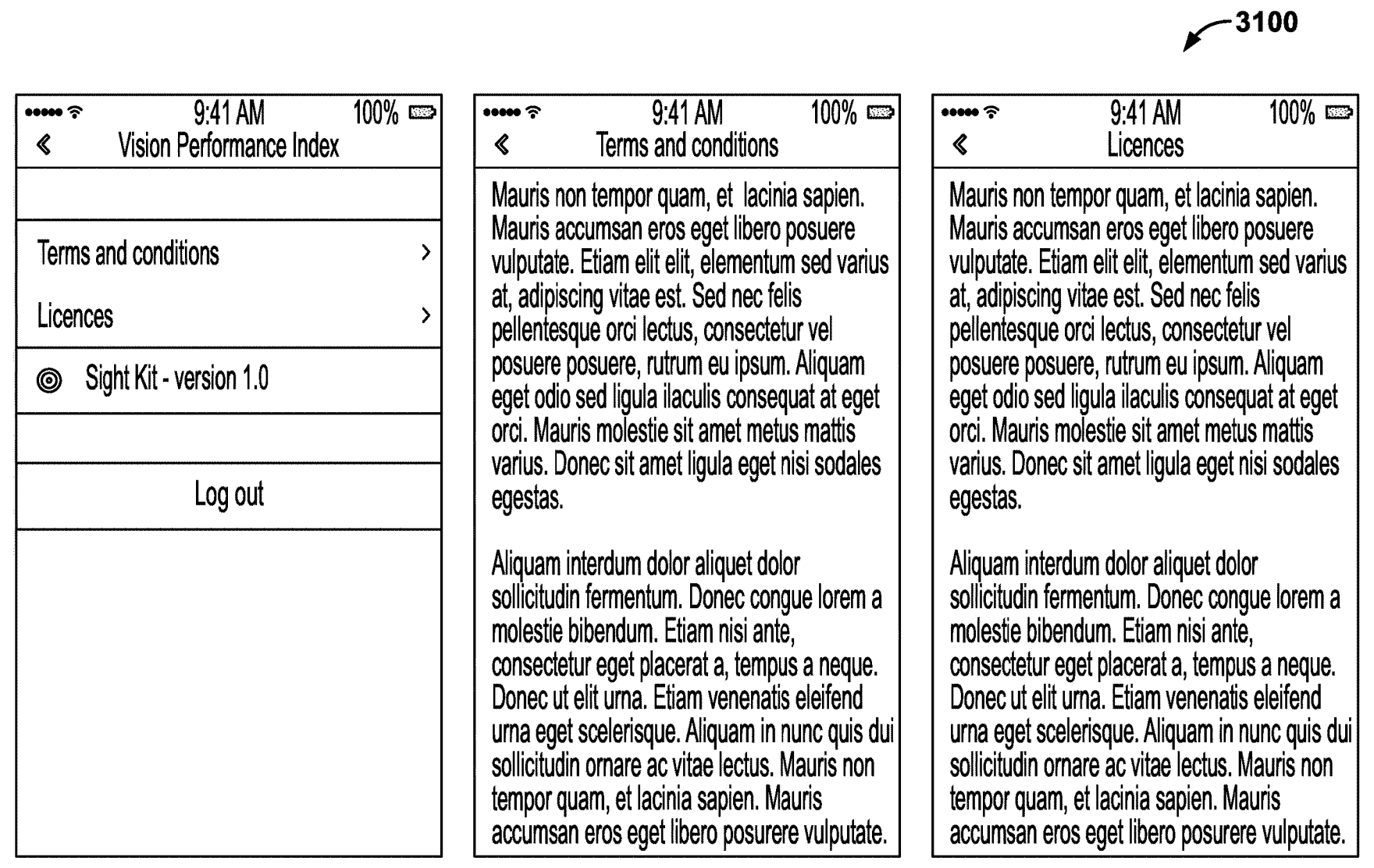

FIG. 31 illustrates screenshots 3100 for 'Settings' and related options within 'Settings', which may be presented through the sight kit application in accordance with an embodiment of the present specification.

From the perspective of the VPI and its components, the Shape Remix game may be similar in contributing data largely for Detection measures. Though there may be differences in the nature of the effect of color, size, position, and contrast on performance. User performance may or may not be equivalent on the two games (Picture Perfect and Shape Remix), while the two games may not be considered redundant. In embodiments, values from the Shape Remix game may be complimentary with that of the Picture Perfect game.

VPI may be determined for the user for each level, each game, and/or for all games played by the user. In some embodiments, a comprehensive VPI report is presented to the user. The comprehensive report may be based on data and score identified through user's interaction with all the games. In some embodiments, the report additionally takes in to consideration different score over a time period over which the user may have interacted with the games. The system may provide additional display options to view an overall VPI score, in addition to VPI scores from each game.

In some embodiments, the system offers the user to repeat interaction with one or more games, until the user is satisfied with the VPI scores. In embodiments, Sight Kit and the resultant VPI score or report may be used to increase awareness of the user's visual system, provide information and develop understanding, and to enable tracking of vision performance over time. Sight Kit may provide a general overview of vision performance and highlight areas for potential improvement.

In an embodiment, Sight Kit provides continuous feedback and uses a variety of stimuli and responses to form a comprehensive picture, thus potentially providing a vast trove of vision data. The VPI scores enable the user to be more aware of their vision and to monitor their vision performance over time. Sight Kit application may measure aspects of users overall vision, inform them of where they may be not performing at their best and provide tips to help maintain their vision at a high level. VPI is designed to give user scores related to specific areas of their vision.

The VPI comprises data measures that are indicative of five components: Field of View, Accuracy, Multi-Tracking, Endurance and Detection (F.A.M.E.D.), which were introduced and described in previous sections of the present specification. For embodiments of the sight kit application, Detection and Accuracy may be considered to be primary measures representing estimates of the user's visual system performance parameters like contrast sensitivity or reaction time. Field of View, Multi-Tracking and Endurance may be considered to be secondary measures that compare primary measures in different contexts like parts of the visual field, focused or divided attention or prolonged engagement.

Each component is further divided into subcomponents. Within the VPI system, each subcomponent is scored, a weighted average of subcomponent scores and other measures is used to generate a component score and finally a weighted average of component scores yields the Vision Performance Index (VPI). Any given experience in the Sight Kit application may only test some of these components, and only by completing all of them can a full picture of the VPI be made. Those subcomponent elements are further described below.

Field of View

Field of View may be a derived, secondary measure. In the VPI system this means that the scores are based on comparing primary measures based on where stimuli appear in the visual field. Certain experiences within the Sight Kit application imply a strategy of fixating on the center of the screen (or bottom-center) and monitoring the surrounding display area for targets (i.e. the first and second rounds of Pop the Balloons). In these contexts we can label stimuli as Central or Peripheral based on their position relative to the presumed area of fixation.

This system may be verified with eye tracking. The field of view scores from a mobile application using sight kit may be somewhat related to perimetry testing of central vision in the clinic.

Central Vision

Central vision scores are based on Detection and Accuracy measures where the stimulus is assumed to be near the central visual field (at stimulus onset). This may be specifically relevant for those occasions where users must make a speeded response (Pop the Balloons). The relevance may reduce for the final round of 'Pop the Balloons'.

Peripheral Vision

Peripheral vision scores are based on Detection and Accuracy measures where the stimulus is assumed to be at the edge of the display. For example, peripheral vision scores are determined where the stimulus is roughly within the outer left and right/top and bottom thirds of the display. Peripheral stimulus onset may be assumed in those contexts where an optimal strategy involves fixating at the center (or bottom-center) of the display, such as the first and second rounds of 'Pop the Balloons'.

Accuracy

Within the VPI system, accuracy is split into two components: one temporal and one spatial. In case of spatial accuracy, users may be rated on their ability to precisely position their responses (i.e. hitting the bullseye), and it is assumed that response positions relative to the intended target will fall in a normal distribution. In the temporal case it is the time users take to respond that is measured, and it is assumed that the time taken to respond to a stimulus after it appears will generally follow a log-normal distribution. In an alternative embodiment, Sight Kit may also include a second temporal model where the time of response is normally distributed around the stimulus onset time (with responses occurring both before and after stimulus onset) for cases where users can anticipate the appearance of a stimulus and respond in synchrony.

Reaction

Reaction times are generated by subtracting the stimulus onset time (when it appears, usually instantly in Sight Kit) from the user's response time. These time spans may be distributed in a log-normal fashion with a characteristic mode and full-width-half-maximum. Reaction scores may be generally based on the mode of a distribution fit to the data. Variations due to Hick's Law may be present, but may not directly influence a user's score as reaction times are fit without regard to set size (most relevant for the third round of Pop the Balloons). Reaction times may be most relevant for the Pop the Balloons game.

Targeting

Targeting precision of response position may be based on the distance (measured in pixels) between the position of the user's response (e.g. tapping to pop a balloon) and the center of the stimulus to which the user is responding and is a basic measure of eye-hand coordination (loosely related to the Compensatory Tracking Task). This measure is from the 'Pop the Balloons' game, although manual dexterity may minimally influence the other games. Targeting precision and reaction time may have an inverse relationship to each other in that the more careful a user is about their aim the slower their responses may be. This effect may average out when calculating a user's overall Accuracy score.

Multi-Tracking

Multi-Tracking may be based on comparing primary measures in the context of either focused or divided attention. Here, attentional demands are proportional to both the number of concurrent tasks and the number of concurrent stimuli.

Focused Attention

Focused attention may be considered to be the state associated with Detection or Accuracy measures where users have only one task to perform and one stimulus to consider at any given time. This is generally the case for the 'Picture Perfect' and 'Shape Remix' games as users are free to process stimulus features serially. This may also be applicable for the beginning of the first round of Pop the Balloons as well as for the entire second round.

Divided Attention

Divided attention is assigned to those primary measures when more than one stimulus (targets or distractors) is present at once and a speeded response requires parallel processing of stimuli. The first and third rounds of 'Pop the Balloons' fit this description in that users may make speeded responses with multiple stimuli present.

Endurance

Endurance measures may relate to how users perform on primary measures over time. Given prolonged engagement it is assumed that performance will begin to decline. After a rest, this loss may be recovered and performance may be back to normal. This assumption relies on users playing the games to the point of fatigue, which may not be reasonable. Interest may fail before performance has a chance to do so. It is possible to add a consideration for time of day, as this is of interest in the analytics dashboard. The application may also consider the current and previous play sessions to generate Endurance related scores relevant to how the user is performing in real time.

Endurance scores are relevant for all experiences within the Sight Kit application. Generating endurance scores does, however, require some minimal duration of engagement with the different games in order to compare present and past data. The relevance of endurance scores depends not on what is played but rather the accumulation of play time.

Fatigue

Fatigue relates scores based on the primary measures from the early and later halves of an ongoing gaming session. Scores are higher if users maintain their level of performance (or even improve over time as with practice) and lower if users' performance begins to slip.

Recovery

Recovery relates scores based on the primary measures from the later half of the last session to the first half of the current session. If fatigue, as described above, has resulted in lower scores at the end of the last session, and if a rest has allowed performance to return to baseline, recovery scores may be higher. If the rest was insufficient and there is little or no recovery from fatigue, recovery scores may be lower.

Detection

Detection measures broadly encompass both measures of sensitivity (whether or not a stimulus is seen) and measures of discrimination (choosing from among similar stimuli). Sight kit may enable successful discrimination of stimuli as a function of color, contrast, or acuity. In this case, a sigmoid function may be fit by Bayesian estimation to the data to derive a discrimination threshold. The games that interact with the user probe errors in matching performed by method of adjustment. In this case, the error in the user's settings may be taken as a direct measure of discrimination threshold.

Color

Color performance in Sight Kit may be based on responses with regard to the chromatic distance between stimuli being discriminated. The application may create a balanced distribution of color discrimination directions and is diagnostic of specific color deficiencies. User's color performance may be based on how fine a discrimination they can make, based on color compared to other users. Users with a marked color deficiency, such as users suffering from dichromacy, may see notably lower scores. Users with slight deficiencies, such as those suffering from anomalous trichromacy, may see lower scores but perhaps within the 'normal' range.

Color scores may be generated by the first and third rounds of 'Pop the Balloons' game and selected rounds within 'Picture Perfect' and 'Shape Remix' games where users are asked to adjust the color (hue) or saturation of images or shapes.

Contrast

Contrast performance in Sight Kit may be based on discrimination between simple patterns with little or no contrast (Pop the Balloons), simple shapes (Shape Remix) and complex photographic images (Picture Perfect). The discrimination in the first round of 'Pop the Balloons' may be, in some ways, similar to the 'Vision Contrast Test System'.

Acuity

Acuity performance in Sight Kit may be based on discriminating briefly presented shapes, speeded response to complex shapes with a mild acuity component, size/alignment (akin to Vernier acuity) and matching blur level. Acuity is relevant for all rounds of 'Pop the Balloons', to one extent or another, and to 'Picture Perfect' and 'Shape Remix' rounds with position, size or sharpness adjustments.

Scoring

The primary measures (Detection and Accuracy) may represent a variety of psychophysical measures tied to physical properties of stimuli and responses, and the secondary measures (Field of View, Multi-Tracking and Endurance) may be largely relational. In order to compare measures across very different experiences, and to combine the various components, a normalizing procedure may be adopted to generate scores. In embodiment, the normalization takes place separately for each unique context, where a context may be considered for each measure for each round of each game.

Measures may generally be distributed normally among the general population. Internally, estimates of central tendency (arithmetic mean) and variability (standard deviation) may be made for each measure in each context based on all of the accumulated data from all users. In some embodiment, these values are used to convert a user's measure under evaluation to a score based on a mean of ½ and a standard deviation of ⅙ (yielding a distribution falling largely between 0 and 1). In some embodiments, these scores are multiplied by a constant to give a larger value for the score. In an embodiment, a constant of 20 is used. In embodiments, the scoring system is designed to stay self-consistent as data are accumulated and it will tell users how they perform relative to all users.

The various VPI components may have some differences from the other conventional methods of measuring vision performance, especially in the context of the few experiences presented by the Sight Kit application.

The Field of View score may not reveal the location or size of a scotoma or field of neglect. Accuracy scores may be influenced by all aspects of vision performance as well as many factors outside of vision. There may be a level of individual variability among users in this regard especially as it will be tied to an individual's affinity for electronic games. FIG. 32 provides a table 3200 to illustrate exemplary experiences of different VPI parameters from the different games and rounds.

In some embodiments, round one of 'Pop the Balloons' game may generate data related to some of FAMED parameters. The data from this experience may inform scores for Detection based on color, contrast and acuity; Accuracy based on reaction and targeting; Field of View and Multi-Tracking with the potential for Endurance given enough play time. The value of this particular experience may primarily be in Accuracy scores, Detection scores based on contrast and acuity and Multi-Tracking scores.

The data from experience with round two of 'Pop the Balloons' game may inform scores for Detection based on acuity, Accuracy based on reaction and targeting and Field of View. The value here may be primarily in Accuracy scores and Field of View, with some value in Detection by acuity.

The data from experience with round three of 'Pop the Balloons' game may inform scores of Detection based on Acuity and Color and Accuracy based on Reaction and Targeting. The primary value is in the Detection and Reaction measures.

The data from experience with 'Picture Perfect' game may inform scores of Detection based on Color, Contrast and/or Acuity.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of assessing a vision performance of a patient using a computing device programmed to execute a plurality of programmatic instructions, comprising:

presenting, via a display on the computing device, a first set of visual stimuli, wherein the first set of visual stimuli comprises a first plurality of visual elements that move from a peripheral vision of the patient to a central vision of the patient;

monitoring a first plurality of reactions of the patient using at least one of the computing device and a separate hardware device;

presenting, via a display on the computing device, a second set of visual stimuli, wherein the second set of visual stimuli comprises a second plurality of visual elements that appear and disappear upon the patient physically touching said second plurality of visual elements, wherein the second set of visual stimuli further comprises a third plurality of visual elements that appear concurrent with said second plurality of visual elements, and wherein the third plurality of visual elements appear different than the second plurality of visual elements;

monitoring a second plurality of reactions of the patient using at least one of the computing device and said separate hardware device; and based upon said first plurality of reactions and second plurality of reactions, determining quantitative values representative of at least one of the patient's field of view, the patient's visual acuity, an ability of the patient to track multiple stimuli, the patient's visual endurance and the patient's visual detection, wherein, when the patient physically touches any of said third plurality of visual elements, the quantitative value representative of the patient's visual acuity is decreased.

2. The method of claim 1 wherein at least a portion of the first plurality of visual elements have sizes that decrease over time.

3. The method of claim 1 wherein at least a portion of the first plurality of visual elements have a speed of movement that increases over time.

4. The method of claim 1 wherein, over time, more of the first plurality of visual elements simultaneously appear concurrent with said second plurality of visual elements on said computing device.

5. The method of claim 1 further comprising presenting, via a display on the computing device, a third set of visual stimuli, wherein the third set of visual stimuli comprises a fourth plurality of visual elements; monitoring a third plurality of reactions of the patient using at least one of the computing device and said separate hardware device; and based upon said first plurality of reactions, second plurality of reactions, and third plurality of reactions determining quantitative values representative of at least one of the patient's field of view, the patient's visual acuity, the ability of the patient to track multiple stimuli, the patient's visual endurance and the patient's visual detection.

6. The method of claim 5 further comprising instructing the patient to identify one of the fourth plurality of visual elements having a specific combination of color, contrast, and/or shape.

7. A method of assessing a vision performance of a patient using a computing device programmed to execute a plurality of programmatic instructions, comprising
presenting, via a display on the computing device, a first set of visual stimuli, wherein the first set of visual stimuli comprises a first plurality of visual elements that move from a peripheral vision of the patient to a central vision of the patient;
monitoring a first plurality of reactions of the patient using at least one of the computing device and a separate hardware device;
presenting, via a display on the computing device, a second set of visual stimuli, wherein the second set of visual stimuli comprises a second plurality of visual elements that appear and disappear upon the patient physically touching said second plurality of visual elements;
monitoring a second plurality of reactions of the patient using at least one of the computing device and said separate hardware device;
presenting, via a display on the computing device, a third set of visual stimuli, wherein the third set of visual stimuli comprises a third plurality of visual elements;
monitoring a third plurality of reactions of the patient using at least one of the computing device and said separate hardware device; and
based upon said first plurality of reactions, second plurality of reactions and third plurality of reactions, determining quantitative values representative of the patient's field of view, the patient's visual acuity, an ability of the patient to track multiple stimuli, the patient's visual endurance and the patient's visual detection.

8. The method of claim 7 wherein at least a portion of the first plurality of visual elements have sizes that decrease over time.

9. The method of claim 7 wherein at least a portion of the first plurality of visual elements have a speed of movement that increases over time.

10. The method of claim 7 wherein, over time, more of the first plurality of visual elements simultaneously appear on said computing device.

11. The method of claim 7 further comprising instructing the patient to identify one of the fourth plurality of visual elements having a specific combination of color, contrast, and/or shape.

* * * * *